US006720473B1

(12) United States Patent
Erf et al.

(10) Patent No.: US 6,720,473 B1
(45) Date of Patent: Apr. 13, 2004

(54) INTRA-VASCULAR ADMINISTRATION OF PARTICLES TO INDUCE PULMONARY HYPERTENSION, PULMONARY HYPERTENSION SYNDROME, AND ASCITES IN POULTRY

(75) Inventors: Gisela F. Erf, Fayetteville, AR (US); Robert F. Wideman, Jr., Fayetteville, AR (US); Howard L. French, Stirling (CA)

(73) Assignee: University of Arkansas, Little Rock, AR (US)

( * ) Notice: Subject to any disclaimer, the term of this patent is extended or adjusted under 35 U.S.C. 154(b) by 48 days.

(21) Appl. No.: 09/913,774

(22) PCT Filed: Jan. 12, 2001

(86) PCT No.: PCT/US01/01147

§ 371 (c)(1),
(2), (4) Date: Aug. 13, 2001

(87) PCT Pub. No.: WO01/50846

PCT Pub. Date: Jul. 19, 2001

Related U.S. Application Data

(60) Provisional application No. 60/176,412, filed on Jan. 14, 2000.

(51) Int. Cl.$^7$ ............... A01K 67/027; A01K 67/00; A01K 67/033; C12N 15/00
(52) U.S. Cl. ............... 800/19; 800/8; 800/13; 800/21
(58) Field of Search ............... 800/19, 8, 22

(56) References Cited

U.S. PATENT DOCUMENTS 6,127,421 A  10/2000  Wideman, Jr. et al. ..... 514/565

OTHER PUBLICATIONS

"Electrocardiographic and Genetic Evaluation of Giant Jungle Fowl, Broilers, and Their Reciprocal Crosses Following Unilateral Bronchus Occusion". Kirby et al. *Poultry Science* 1999, vol. 78, pp. 125–134.

"Effect of Dietary dl–Alpha Tocopherol on Tissue a– and y–tocopherol and Pulmonary Hypertension Syndrome (Ascites) in Broilers". Bottje et al. *Poultry Science* 1997, vol. 76, pp. 1506–1512.

"Broiler Breeder Survivors of Chronic Unilateral Pulmonary Artery Occlusion Produce Progeny Resistant to Pulmonary Hypertension Syndrome (Ascites) Induced by Cool Temperatures". Wideman Jr. et al. *Poultry Science* 1999, vol. 78, p. 404–411.

"Lung Mass Cell Density and Distribution in Chronically Hypoxic Animals". Tucker et al. *J. Appl. Phys. Resp. Env. Exerc. Physiol.*, 1997, vol. 42, No. 2, pp. 174–178.

*Primary Examiner*—Peter Paras
(74) *Attorney, Agent, or Firm*—Head, Johnson and Kachigian

(57) ABSTRACT

A new method for identifying and eliminating chickens that are susceptible to pulmonary hypertension uses micrometer scale particles to occlude blood vessels in the lungs of the chickens. This results in the death of chickens that are pre-disposed to pulmonary hypertension. The invention effectively culls a chicken stock of the weaker animals.

2 Claims, 17 Drawing Sheets

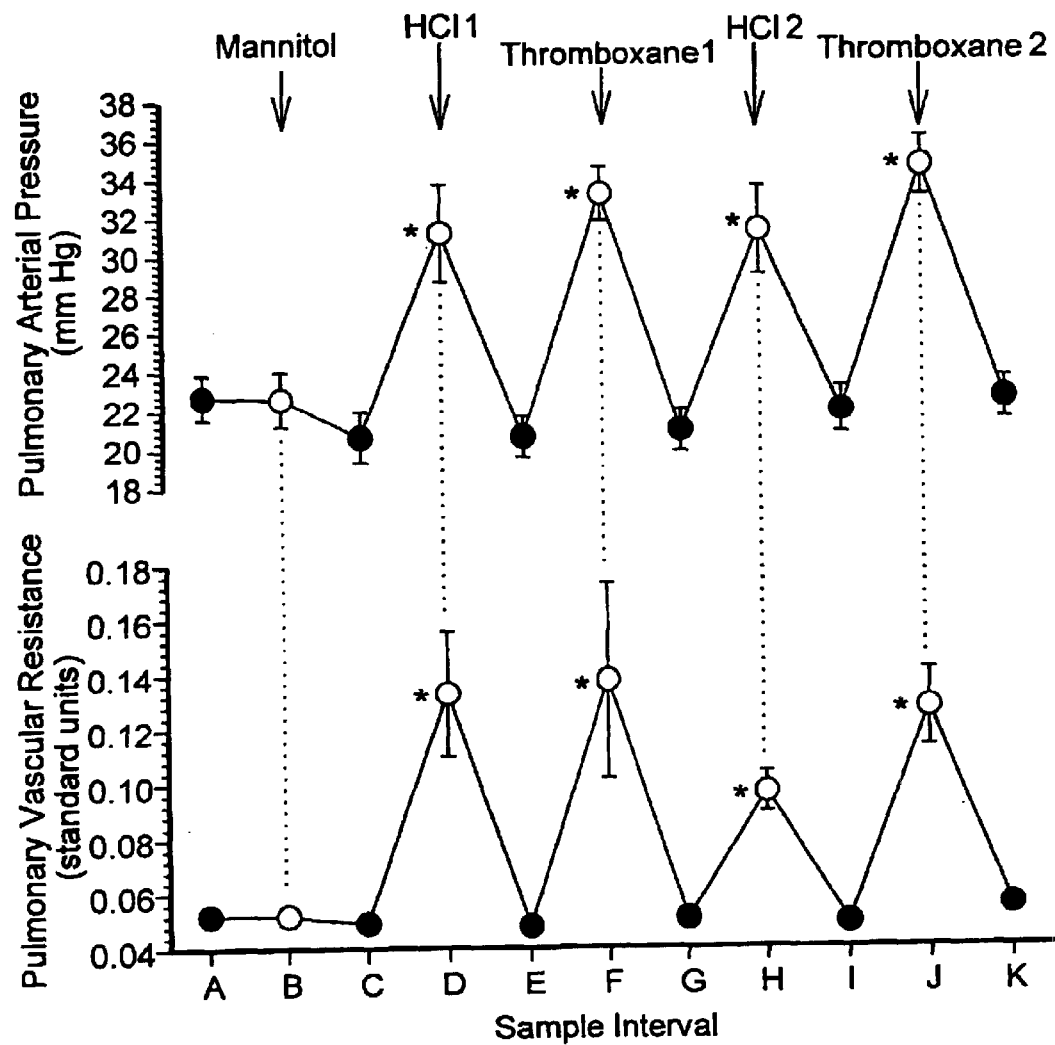

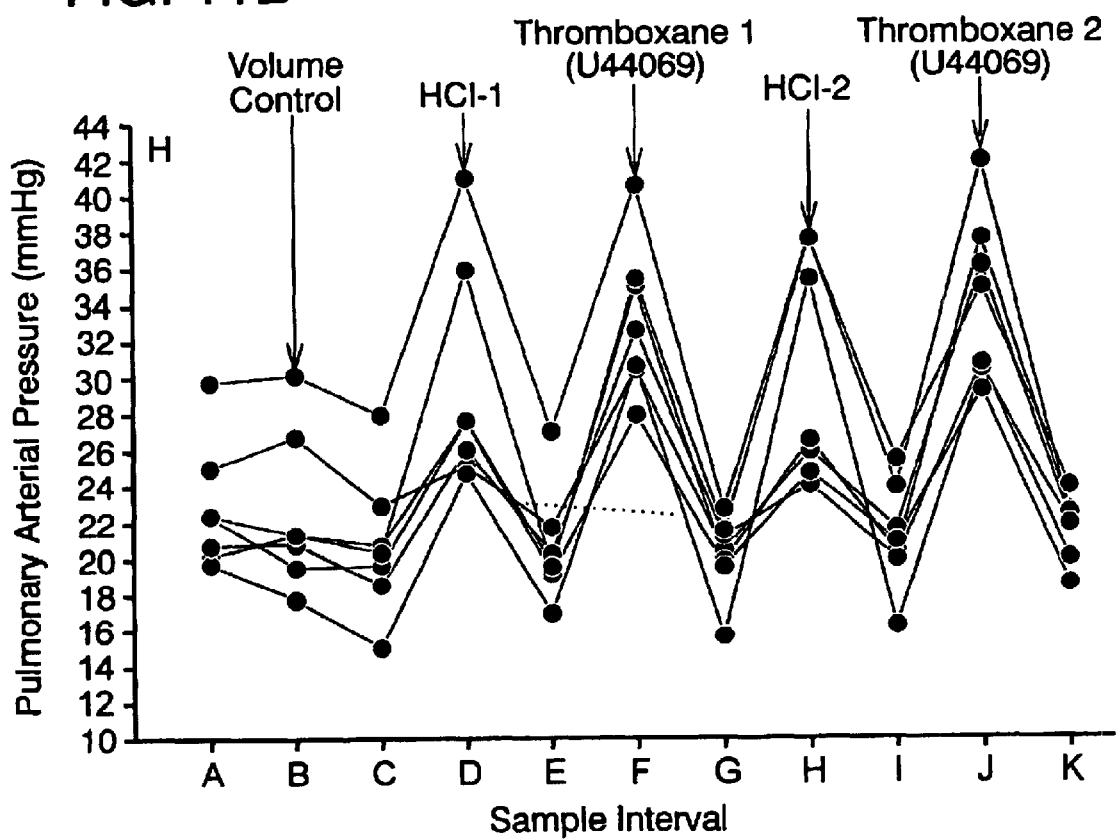

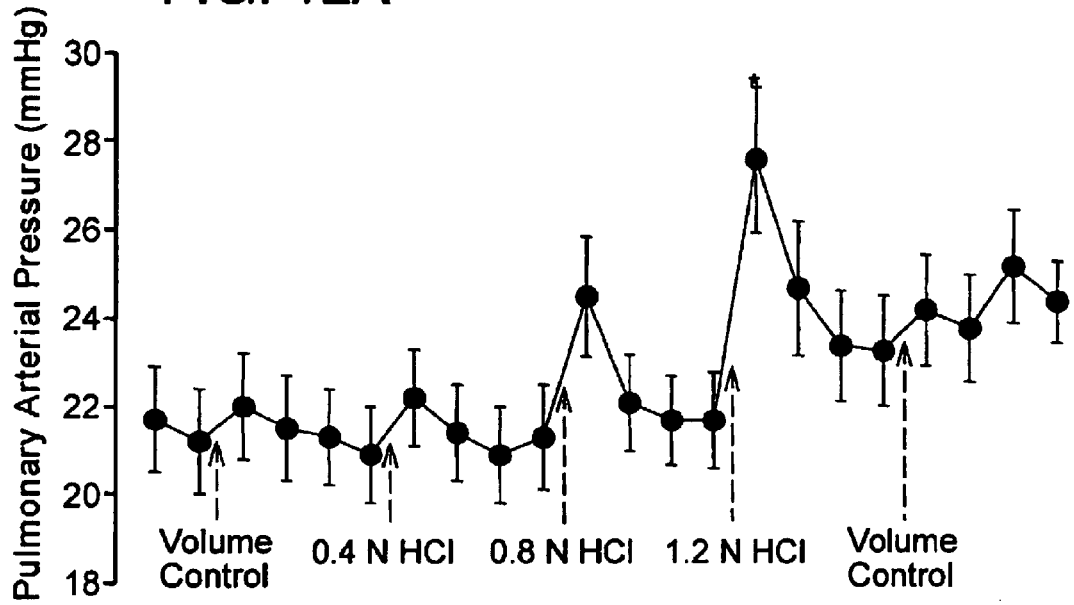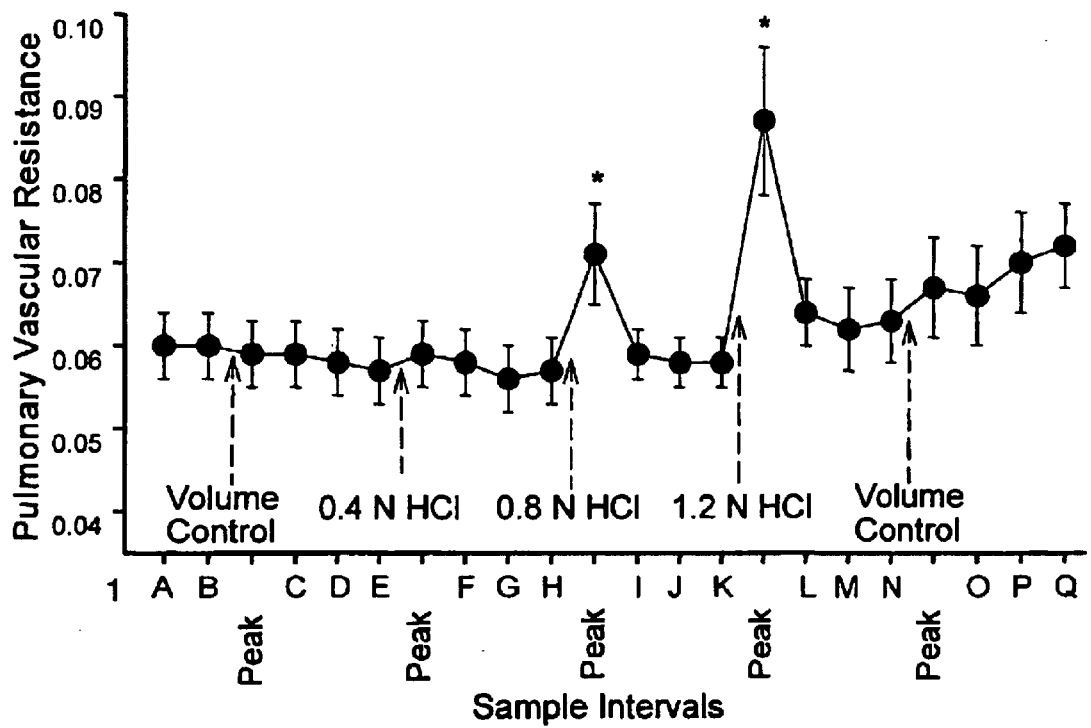
FIG. 12A

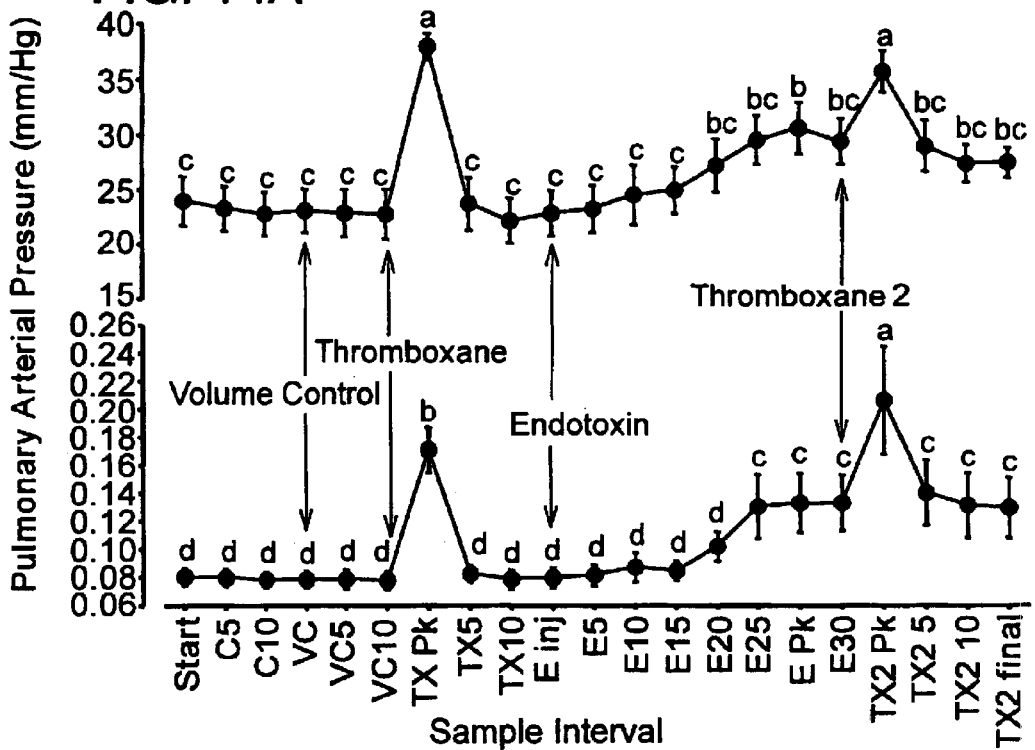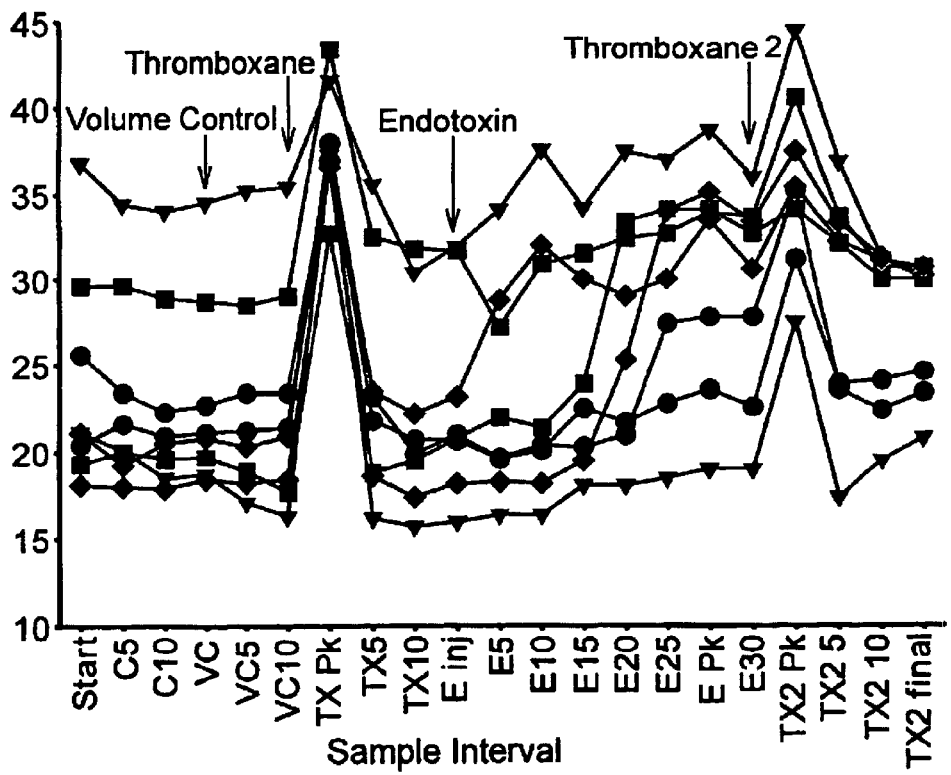

INTRA-VASCULAR ADMINISTRATION OF PARTICLES TO INDUCE PULMONARY HYPERTENSION, PULMONARY HYPERTENSION SYNDROME, AND ASCITES IN POULTRY

CROSS-REFERENCE TO RELATED APPLICATIONS

Priority is claimed from provisional application U.S. Serial No. 60/176,412 filed on Jan. 14, 2000, and incorporated by reference herein.

BACKGROUND

In order to propel the requisite cardiac output through the lungs, the right ventricle must develop a pulmonary arterial pressure sufficient to overcome the resistance to blood flow offered by the pulmonary vasculature. According to the equation, pulmonary arterial pressure=cardiac output pulmonary vascular resistance, the blood pressure within the pulmonary circulation must increase (pulmonary hypertension must develop) whenever the cardiac output cannot be accommodated by the pulmonary vascular capacity. In this context, the vascular capacity is broadly defined to encompass anatomical constraints related to the compliance and volume of the blood vessels, as well as metabolic limitations related to the tone (state of contracture) maintained by the resistance vessels (Wideman and Bottje, 1993; Wideman et al, 1996a,b, 1998a,b, 1999a,b). In broiler chickens, pulmonary hypertension initiates a distinctive pathophysiological progression that terminates as pulmonary hypertension syndrome, also commonly known as ascites (Julian, 1993; Odom, 1993; Wideman and Bottje, 1993; Wideman, 1999). Broilers exhibit a similar pathophysiological progression under a variety of environmental and management conditions, providing support for the hypothesis that increases in the cardiac output and an inadequate pulmonary vascular capacity constitute common mechanisms through which multiple factors can initiate pulmonary hypertension leading to ascites. For example, fast growth and cool temperatures elevate the cardiac output and serve as the most common triggers for ascites in broilers reared near sea level, whereas hypoxic pulmonary vasoconstriction contributes to high incidences of ascites in broilers reared at high altitudes (Cueva et al., 1974; Huchzermeyer and DeRuyck, 1986; Julian, 1993; Odom, 1993; Wideman and Bottje, 1993; Roush et al., 1996, 1997; Wideman, 1997; Wideman et al., 1996a,b, 1998a,b,c, 1999a,b).

A genetic component of ascites susceptibility has been revealed by surgically occluding one pulmonary artery in male and female broiler breeder parents. Unilateral pulmonary artery occlusion applies extremely rigorous and directly focused selection pressure, causing those individuals incapable of tolerating a direct doubling of the pulmonary vascular resistance to rapidly develop ascites. The survivors of chronic unilateral pulmonary artery occlusion apparently possess a cardio-pulmonary capacity sufficient to accommodate the combined challenges of an elevated pulmonary vascular resistance, a disproportionately high rate of blood flow through the unoccluded lung, and sustained pulmonary hypertension (Wideman and Kirby, 1995, 1996; Wideman et al., 1996a,b, 1997). First generation broiler breeder survivors of unilateral pulmonary artery occlusion, subsequently produced male and female progeny exhibiting about a 50% reduction in ascites susceptibility when grown as rapidly as possible during exposure to cool temperatures (Wideman and French, 1999a). Survivors of a second generation of selection, subsequently produced progeny exhibiting about a 90% reduction in ascites susceptibility when compared with the base population from which the ascites resistant line was developed (Wideman and French, 1999b). This rapid pace of genetic improvement confirms the central contribution of an inadequate pulmonary vascular capacity to the ascites susceptibility of broilers. Furthermore, the gene or genes involved in ascites susceptibility appear to be dominant, indicating ongoing proactive exposure and elimination of susceptible individuals will be required to achieve an overall improvement in ascites resistance (Wideman and French, 1999a,b).

The unilateral pulmonary artery occlusion technique is impractical for large-scale genetic selection programs, because considerable time and surgical expertise are required to correctly clamp the delicate and poorly accessible pulmonary artery. More efficient methodologies for triggering controlled, sustainable increases in pulmonary vascular resistance are needed before ascites susceptibility can be eliminated routinely from commercial broiler populations. Chemical mediators of pulmonary vasoconstriction are expensive, and tend to produce transient responses unsuitable for maintaining the pulmonary hypertension necessary to expose ascites susceptibility (Wideman et al., 1998a, 1999a; Wideman, 1999).

SUMMARY OF THE INVENTION

This invention relates to a new process for inducing pulmonary hypertension in animals, with an objective of identifying and/or eliminating susceptible individuals or families, as well as hypertension resistant ones to achieve genetic improvement in agriculturally important breeds of poultry (broiler chickens and turkeys), and cattle. The invention also will be useful for animal research directed toward understanding pulmonary hypertension and its sequelae in human patients as well as in animals. Sustained pulmonary hypertension leads to pulmonary hypertension syndrome which adversely impacts poultry production throughout the world, as well as cattle production when cattle are kept at altitudes sufficiently high to challenge blood oxygenation. In poultry, the pathophysiological progression of pulmonary hypertension syndrome leads to terminal ascites (fluid accumulation in the abdominal cavity) followed by death of the animal.

A basis of the invention is the novel concept that particulate substances of a size (approximately 8 to 250 $\mu$m diameter) suitable for occluding blood vessels in the lungs (pulmonary vasculature) can be suspended in an appropriate carrier vehicle, and the suspension then can be injected intravenously. The venous blood then carries the particles to the right ventricle of the heart, which in turn pumps the blood containing the particles to the lungs. The particles directly increase pulmonary vascular resistance by lodging in small blood vessels, thereby partially blocking blood blow. Proportional or variable occlusion of the pulmonary vasculature can be accomplished by adjusting the number of particles administered. By increasing the resistance to pulmonary blood flow, the right ventricle of the heart is forced to develop and maintain an elevated pressure in the pulmonary arteries (pulmonary hypertension) to propel the requisite cardiac output through the vessels remaining unoccluded. Animals that are susceptible to pulmonary hypertension subsequently will develop pulmonary hypertension syndrome. Animals that are resistant to pulmonary hypertension will not develop pulmonary hypertension syndrome. The resistant animals or their pedigreed families can be selected for breeding genetic stocks that are resistant to the onset of pulmonary hypertension, pulmonary hypertension syndrome, and/or ascites. Increasing or decreasing the numbers of particles administered can be used to increase or decrease, respectively, the degree of pulmonary vascular obstruction and thereby the selection pressure applied to the animal population. Researchers also may use this as an experimental technique for triggering pulmonary hypertension in experimental animals. This invention also may trigger a pulmonary vascular inflammatory response, which will be useful in research directed toward understanding the responses of the immune system within the lungs.

This invention has the following advantages: (a) individual animals can be evaluated and/or selected based on simple, inexpensive intravenous injections; (b) relatively unskilled personnel can treat thousands of animals per day; (c) the degree of selection pressure can be varied; (d) before and after the injections, the animals can be maintained in typical production facilities without additional expensive requirements for inducing pulmonary hypertension; and, (e) the invention directly/physically affects the pulmonary vasculature without requiring ongoing pharmacological intervention.

Present genetic selection techniques involve prolonged exposure to cool temperatures or hypobaric hypoxia (low atmospheric pressure and thus low oxygen), coupled with various measurements of symptoms related to the onset of pulmonary hypertension and the progression to pulmonary hypertension syndrome (see Wideman et al., 1998. Poultry Science 77:1565–1573). These Conditions require specialized, expensive facilities that generally can accommodate relatively few individuals, and that generally do not apply sufficient selection pressure to achieve rapid genetic progress.

Alternatively, surgical occlusion of one pulmonary artery has been used to trigger a high incidence of pulmonary hypertension syndrome in broiler chickens. The resistant survivors are known to produce progeny that are highly resistant to pulmonary hypertension syndrome (see Wideman et al., 1997. Poultry Science 76:400–404; Wideman and French, 1999. Poultry Science 78:404–411; Wideman and French, 1999). This research proved the validity of partially obstructing the pulmonary vasculature as a means for selecting genetically resistant individuals. However, sophisticated surgical skills and equipment are required for unilateral pulmonary artery occlusion, only 100 birds can be prepared by a two-person team per day, and the process is quite expensive.

The present invention involves an animal exhibiting pulmonary hypertension syndrome, the animal being produced by the administration of pulmonary vasculature-blocking particles to the pulmonary vasculature.

Also involved is a process for producing a population of animals having increased resistance to pulmonary hypertension, the process comprising eliminating animals most susceptible to pulmonary hypertension induced by intravascular particle administration.

This invention may also be used to achieve genetic improvements and other agriculturally important breeds. This is particularly true for breeds subject to pulmonary hypertension and its sequelae. In another aspect, this invention involves for producing improved genetic breeding stocks. This again involves inducing pulmonary hypertension in animals, the method comprising: a) inducing pulmonary hypertension in animals by occluding the pulmonary vasculature with particulate substances of a size about 8 to about 250 micrometers in diameter injected into veneous blood that carries the particles to the right cardiac ventricle pumping the blood containing the particles to the lungs, wherein the particles directly increase pulmonary vascular resistance by lodging in small blood vessels, the heart being forced to develop and maintain an elevated pressure in the pulmonary arteries to propel the requisite cardiac output through vessels remaining unoccluded, animals that are susceptible to pulmonary hypertension subsequently developing pulmonary hypertension syndrome, and b) separating susceptible animals from the resistant animals, the resistant animals being useful as genetic breeding stock resistant to pulmonary hypertension.

Cattle, chickens, pigs and other domestic stock may be subject to pulmonary hypertension, and thus, be the animals of the present invention. In certain cases, the breeding stock produced by the methods of the present invention may be utilized to characterize any novel DNA allelic markers that appear in animals resistant to pulmonary hypertension. Likewise, animals that are killed or sickened by the particle injection of the present invention may be analyzed for genetic allelic DNA markers that are found in such susceptible stock. Those of skill in the art will understand how to do allelic analyses between resistant and susceptible animals and base stock to find the appropriate allelic DNA markers. Once these genetic markers are found, they may be used to select breeding stock.

In summary, the present invention involves a method for producing a pulmonary hypertension resistant poultry strain in its most preferred embodiment. This method involves a) administering into the pulmonary circulation of immature poultry particles having about 8 to about 250 $\mu$M diameters in an amount sufficient to kill or disable animals susceptible to pulmonary hypertension; and b) selecting and breeding healthy survivors to produce a pulmonary hypertension resistant poultry strain.

BRIEF DESCRIPTION OF THE DRAWINGS

FIG. 11A is a graph showing pulmonary arterial pressure and pulmonary vascular resistance (standard units) in 8 male broilers, illustrating baseline values (closed symbols) and the peak pulmonary arterial pressure responses (open symbols) within 5 minutes after an i.v. bolus injection of 2.5% mannitol (volume control), or repeated i.v. injections of 1.2 N HCl (HCL-1, -2) and the thromboxane mimetic U44069 (thromboxane-1, -2). Asterisks(*) designate differences (P 0.05) compared with the pre-injection baseline value.

FIG. 11B is a graph showing pulmonary arterial pressures of the individual birds before, during, and after the peak response to the respective injections. Lines connecting before, during, and after the peak responses to the respective injections. Lines connecting individual bird values illustrate variability (from Wideman et al., 1999a. *Poultry Sci.*, 78:714–721).

FIG. 12A is a graph showing pulmonary arterial pressure and pulmonary vascular resistance (standard units) in 14 male broilers at 5 minute intervals, including the peak pulmonary arterial pressure response to 1.5 mL i.v. bolus injections of 2.5% mannitol (volume control) or 0.4,0.8, and 1.2 N Hcl. Asterisks (*) designate difference (P 0.05) compared with all three of the samples preceding the 0.8 and 1.2 N HCl injection.

FIG. 14A is a graph showing pulmonary arterial pressure and pulmonary vascular resistance (standard units normalized per kg BW) in 8 male broilers at the start of data collection (Start), at 5 minute intervals during the control period (C5 to C10), within 60 seconds after the volume control injection (Vinj), at 5 minute intervals during the volume control period (V5 to V10), at the peak pulmonary arterial pressure response within 60 seconds after injecting equal doses of the thromboxane mimetic U44069 (Tx Pk, Tx2Pk), at 5 minute intervals after thromboxane injections (Tx5 to Tx10; Tx2 5 to Tx2 final), within 60 sends after the 1 mg LPS injection (Einj), at 5 minute intervals after the 1 mg LPS injection (E5 to E30), and during the maximum pulmonary arterial pressure response to the 1 mg LPS (E Pea&). Different letters (a–d) designate differences between means over time (P 0.05).

FIG. 14B is a graph showing pulmonary arterial pressures of the individual birds over the course of the experiment. Lines connecting individual bird values illustrate variability sideman and Erf, unpublished).

DETAILED DESCRIPTION OF THE INVENTION

Figure 1:
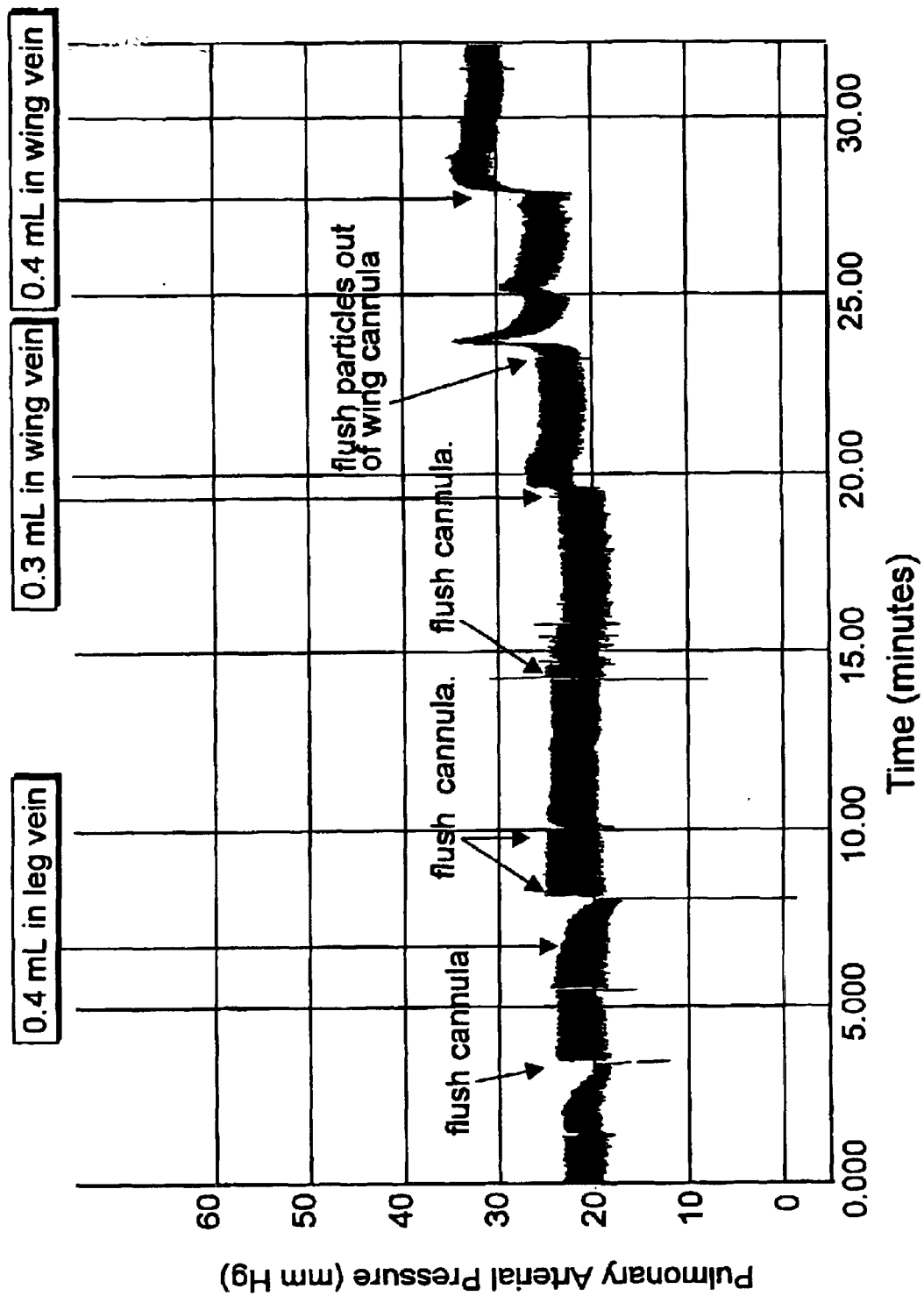
FIG. 1 is a physiograph recording of pulmonary arterial pressure in a male broiler during sequential injections of silica gel (0.1 g/mL heparinized saline) into a leg vein flowing into the renal portal system (0.4 mL in leg vein), or into a wing vein returning to the right ventricle and thus lungs (0.3 and 0.4 mL in wing vein). The "flush cannula" markers denote 1 mL injections of heparinized saline (150 units ammonium heparin/mL 0.9% NaCl) into the pulmonary artery cannula to reduce blood clot formation at the tip of the cannula (note reduced pulse pressure prior to the first three flushes). The "flush particles out of wing vein cannula" marker denotes an injection of 1 mL heparinized saline through the wing vein cannula to rinse retained silica gel particles into the venous blood.

The present invention provides an alternative method to identify and select animals resistant to pulmonary hypertension. Particles sized to block the pulmonary microvasculature are injected into a suitable systemic vein, and are carried by the returning venous blood to the lungs. Physical occlusion of the pulmonary microvasculature, in proportion to the number of particles injected, provides the means for efficiently creating a controllable, sustained increase in pulmonary vascular resistance. Indeed, the capacity of blood-borne microparticulates to physically lodge within the systemic or pulmonary microvasculature serves as the basis for using intravascularly injected microspheres of various sizes (e.g., $15\mu$ to $52\mu$ diameter) and compositions (e.g., cross-linked dextran, polystyrene) to measure the distribution of blood flow to, or within, various organs and tissues (Boelkins et al., 1973; Wolfenson et at., 1978; Scheid and Holle, 1978; Wolfenson, 1983; Brackenbury et al., 1990; Bernard et al., 1996). A pulmonary vascular trapping efficiency of close to 100% has been validated for $15\mu$ to $52\mu$ diameter microspheres in several avian species (Boelkins et al., 1973; Sheid and Holle, 1978; Brackenbury et al., 1990). Only trace quantities of microspheres are injected during blood flow studies, specifically to avoid vascular occlusion and the consequent alteration of microvascular hemodynamics. It also has been recognized that microspheres injected into venous portal blood flowing into the avian liver or kidneys will become trapped within the hepatic and renal portal sinusoids, thereby preventing those intravenously injected microspheres From reaching the lungs (Wolfenson et al., 1978; Wolfenson, 1983). The results reported herein were to evaluate the efficacy of injecting microparticulates intravenously in quantities sufficient to directly trigger an increase in pulmonary vascular resistance leading to pulmonary hypertension Experiments were conducted showing that a sustained increase in pulmonary arterial pressure (pulmonary hypertension) is triggered by intravenous injections of particles sized to block the pulmonary microvasculature and thereby increase the pulmonary vascular resistance. Particles carried to the lungs by the returning venous blood triggered physiological responses resembling those caused by unilateral pulmonary artery occlusion, including pulmonary hypertension, systemic hypoxemia, and systemic hypotension. Acute physiological studies using anesthetized male broilers consistently demonstrated that repeated intravenous injections of organic (cellulose or dextran polymers) or inorganic (silica gel) micro-particles triggered pulmonary hypertension in proportion to the cumulative quantities of particles injected. Subsequent to micro-particle injections, the cardiac output was forced through fewer vascular channels, revealing a diffusion limitation characterized by undersaturation of the systemic arterial blood with oxygen (hypoxemia). Hypoxemic vasodilation of the systemic vasculature (reduced total peripheral resistance) triggered systemic hypotension (reduced systemic arterial pressure). Chronic studies using unanesthetized male broilers demonstrated that intravenously injected organic or inorganic micro-particles triggered pulmonary hypertension syndrome (ascites) in proportion to the quantities of particles injected and the magnitude of the associated sustained increase in pulmonary arterial pressure. The intravenous micro-particulate injection methodology can be used as an efficient and minimally invasive technique for inducing sustained pulmonary hypertension to routinely expose and eliminate ascites-susceptible individuals from commercial broiler lines as well as to identity, select and breed animals resistant to particle induced pulmonary hypertension.

Materials and Methods

Animal Management

All male broilers were donated by a commercial hatchery[1] on the day of hatch (Day 1). They were transported to the Poultry Environmental Research Lab at the University of Arkansas Poultry Research Farm, where they were wing banded and placed on fresh wood shavings litter in environmental chambers (8 $m^2$ floor space). Chicks were brooded at 33 C on Days 1 to 5,29 C on Days 6 to 10, and 21 to 24 C thereafter. They were fed a 23% CP com-soybean meal-based broiler ration formulated to meet or exceed the minimum NRC (1984) standards for all ingredients. Feed and water were provided for ad libitum consumption. Lights were on for 24 h/d through Day 5, and for 23 h/d thereafter.

[1]Hubbard ISA, Hot Springs, Ariz. 71902.

EXAMPLES

The following examples further illustrate the present invention including preferred versions and methods of making the same; however these examples are not to be construed as limitations of this invention.

Example 1

Inorganic Particulate Injections

Physiological Evaluation of Silica Gel in Anesthetized Broilers. At 30 d of age, three broilers (1416±81 g BW) without obvious cyanosis of the comb were prepared for pulmonary arterial pressure recordings. The surgical protocol has been described previously (Wideman and Kirby, 1995b; Wideman et al., 1996, 1998a, 1999). All birds had full access to feed and water until they were anesthetized. A surgical plane of anesthesia was induced with intramuscular injections of allobarbital (5,5-diallyl-barbituric acid;[2] 25 mg kg/BW). The birds were fastened in dorsal recumbency on a surgical board thermostatically regulated to maintain a surface temperature of 30 C. An incision was made to open the thoracic inlet, and the left pulmonary artery was exposed. A 27 GA×1 inch needle, bent to a 90° angle mid-way along its length, was scored and snapped off adjacent to the hub. The resulting blunt end was pressure-fit into a 30 cm length of Silastic® Tubing (0.012 in I.D., 0.037 in O.D.[3])filled with heparinized saline. The point of the needle was inserted into the left pulmonary artery, a 4 cm loop of the Silastic® tubing was coiled inside the thoracic inlet to provide strain relief during respiratory motion, and the thoracic inlet was sealed with stainless steel wound clips. The distal end of the Silastic® tubing was attached to a blood pressure transducer interfaced through a Trans-bridge™ preamplifier[4] to a Biopac MP 100 data acquisition system[5] using AcqKnowledge software.[5] The left cutaneous ulnar vein was cannulated with PE-50 polyethylene tubing for systemic i.v. injections, and the left anterior tibial vein was cannulated with polyethylene tubing for i.v. injections into the renal portal system. Ongoing intravenous infusions were not administered. When surgical preparations were complete and a stabilization period of 20 min had elapsed, control PAP data were recorded. Silica gel (32µ to 63µ size range)[6] was mixed at 0.1 g/mL in heparinized saline (150 units ammonium heparin[2]/mL of 0.9% NaCl), and the mixture was vortexed continuously on a magnetic string plate to keep the particles suspended. The mixture was injected i.v. in volumes of 0.1 to 0.5 mL (0.01 to 0.05 g) while PAP was recorded. After appropriate recordings were obtained, the birds were euthaized with an overdose of anesthetic.

[2]Sigma Chemical Co., St Louis, Mo. 6317-89916.
[3]Konigsberg Instruments, Inc., Pasadena, Calif. 91107-3294.
[4]World Precision Instruments, Sarasota, Fla. 34230.
[5]Biopac Systems, Inc., Santa Barbara, Calif. 93117.

Evaluation of Low-Dose Silica Gel in Unanesthetized Broilers. Unanesthetized birds from the same hatch were injected via the cutaneous ulnar vein at 30 d of age with the same silica gel suspension (0.1 g/mL) at volumes of 1.0 mL (one bird), 0.5 mL (one bird), 0.3 mL (one bird), 0.2 to 0.25 mL (twelve birds), or 0 mL (uninjected controls, eight birds), and then were returned to the environmental chamber. Oximetry values, heart rates and hematocrits were acquired from all surviving birds at 37 d of age. A universal "C" sensor attached to a Vet/Ox™ 4403 pulse oximeter[7] was positioned on the wing to illuminate the tissue between the radius and ulna for measurements of percentage saturation of hemoglobin with oxygen and heart rate (Peacock et al., 1990; Julian and Mirsalimi, 1992; Wideman and Kirby, 1995; Wideman et al., 1998c). Blood was obtained by venipuncture for duplicate hematocrit (HCT) determinations using heparinized capillary tubes and a microhematocrit centrifuge. At 45 d of age, the birds were weighed, injected i.v. with 5 mL of heparied saline to prevent the blood from clotting, euthanized with $CO_2$, and within 5 min were perfused through the right ventricle with 50 mL of 10% phosphate buffered formalin to fix the lungs in situ (Owen et al., 1995b). One hour later, the lungs were removed and immersed in 10% phosphate buffered formalin[6] for histology. The heart was dissected to obtain ventricular weights for calculating the RV:TV ratio as an index of pulmonary hypertension (Burton et al., 1968; Cueva et al., 1974; Huchzermeyer et al., 1988).

[6]Fisher Scientific, St Louis, Mo. 63178-4989.
[7]Sensor Devices, Inc., Waukesha, Wis. 53188.

Results and Discussion of Example 1

Physiological Evaluation of Silica Gel in Anesthetized Broilers. The silica gel rapidly settled out of suspension when aspirated into a syringe for i.v. injections, and tended to clog needles of 23 GA or smaller. Typical responses by an individual male broiler (PAP3, 1492 g BW) to i.v. injections of the silica gel mixture are shown in FIG. 1. The initial pulmonary arterial pressure averaged approximately 22 mm Hg. Injecting 0.4 mL (0.04 g silica gel) into the leg vein had no impact on pulmonary arterial pressure, presumably because the particles became trapped in the renal portal sinusoids before the venous blood returned to the right ventricle and lungs (Wolfenson et al., 1978; Wolfenson, 1983). The subsequent 0.3 mL (0.03 g silica gel) injection into the wing vein increased the pulmonary arterial pressure to a peak of 25 mm Hg, with the pressure subsiding to 23 mm Hg within one min. A portion of the particles remained visible in the wing vein cannula, and flushing the cannula with 1.0 mL of heparinized saline triggered a secondary peak in the pulmonary arterial pressure. A final injection of 0.4 mL (0.04 g silica gel) into the wing vein cannula caused the pulmonary arterial pressure to increase to 31.5 mm Hg (FIG. 1). This increase in PAP then was sustained for over one hour (not shown), when the experiment was terminated. For all three birds, cumulative wing vein injections of ≧0.4 mL (0.04 g of silica gel) caused sustained increases in pulmonary arterial pressure (not shown).

Evaluation of Low-Dose Silica Gel in Unanesthetized Broilers. Unanesthetized birds injected via the wing vein with 0.3 to 1.0 mL (0.03 to 0.10 g) of the silica gel mixture turned cyanotic, exhibited respiratory distress, and died. Of the twelve birds injected with 0.02 to 0.025 g silica gel, four died within five min, and the remaining eight exhibited varying degrees of respiratory distress. A 0.2 to 0.25 mL (0.02 to 0.025 g) dose had consistently been tolerated with only a small increase in pulmonary arterial pressure in the anesthetized and cannulated birds, suggesting pre-injection with heparinized saline (administered to keep clots from forming in the cannulae) or other anticoagulants (citrate, EDTA, EGTA) may be necessary to prevent particulates from triggering life-threatening blood clot formation in uncannulated, unanesthetized birds. Eight of the injected unanesthetized birds, along with eight uninjected controls, lived to 45 d of age. As shown in Table 1, none of the control birds and one of the injected birds developed ascites. The final body weight, ventricular weight, and physiological variables did not differ (P≧0.05) between the control and particle-injected groups. The lack of group differences for RV:TV ratios, as well as for absolute and BW-normalized right ventricular weights, indicate these low i.v. doses of silica gel were inadequate to occlude pulmonary blood vessels in proportions sufficient to trigger sustained pulmonary hypertension. These observations are consistent with the transient pulmonary hypertensive response to a slightly higher dose of silica gel (0.3 mL; 0.03 g) injected i.v. into anesthetized birds (FIG. 1). Histopathological evaluation of lungs collected at 45 d of age failed to reveal any silica gel particles remaining anywhere in the tissue, suggesting the possibility that macrophages cleared the particles from the lungs.

TABLE 1

Ascites incidence, final body weight, absolute and body weight-normalized ventricular weights, heart rate, saturation of hemoglobin with oxygen, and hematocrit in uninjected control broilers and broilers injected i.v. with 0.02 to 0.025 g silica gel (data are Means ± SEM).

| | Experimental Groups | | |
|---|---|---|---|
| Variable | Control | Particle Injected | P |
| Ascites Incidence, % | 0 (0/8) | 12.5 (1/8) | ns |
| Final body weight (g) | 2691 ± 22 | 2592 ± 126 | 0.464 |
| Right ventricle (g) | 2.17 ± 0.25 | 2.26 ± 0.27 | 0.818 |
| Left ventricle + septum (g) | 7.73 ± 0.33 | 6.73 ± 0.43 | 0.087 |
| Total ventricle (g) | 9.90 ± 0.54 | 8.99 ± 0.33 | 0.173 |
| RV:TV ratio | 0.215 ± 0.045 | 0.254 ± 0.100 | 0.333 |
| Right ventricle/BW | 0.0008 ± 0.0001 | 0.0009 ± 0.0002 | 0.581 |
| Left ventricle + septum/BW | 0.0029 ± 0.0001 | 0.0026 ± 0.0001 | 0.068 |
| Total ventricle/BW | 0.0037 ± 0.0002 | 0.0035 ± 0.0001 | 0.494 |
| Heart rate (beats/min) | 390 ± 4 | 368 ± 10 | 0.063 |
| Hb saturation with $O_2$, % | 88 ± 1 | 88 ± 2 | 0.907 |
| Hematocrit, % | 35 ± 1 | 34 ± 1 | 0.430 |

Example 2

Organic Particulate Injections

Instructions for Particle Injections:

Heparinized Avian Saline (0.9% NaCl @ 200 units heparin/mL)

Weigh out 9.0 grams of sodium chloride (NaCl)
Weigh out 1.2 grams of ammonium heparin (=206,400 units @ 172 units/mg)

Add to 1 Liter of distilled water in a flask, stir until dissolved (store frozen in 200 mL bottles; thaw just prior to use)

Cellulose Injection Solution (0.02 grams cellulose/mL)

Precisely weigh out 1 gram of cellulose into each 50 mL sterile culture tube. Cap each tube immediately and store at room temperature or in a refrigerator (do not freeze).

Caution: keep the cellulose containers closed airtight; do not let the cellulose absorb moisture from the air. This will make it heavier (fewer particles per gram) and can cause it to swell (difficult to inject through the needle).

Immediately prior to injection:

Precisely measure 50 mL of the heparinized avian saline into a graduated cylinder.

Pour a portion of this (approximately 20 mL) into the culture tube containing 1 gram of cellulose. Cap the tube, then mix thoroughly on a vortex mixer (about 1 min). Uncap, add the remainder of the measured 50 mL heparinized avian saline, recap and re-vortex (about 15 sec). Mix thoroughly with no clumps!

Pour the 50 mL of cellulose-heparinized saline into a small beaker. Use a magnetic stirrer to keep the particles evenly suspended (fast enough to maintain a small vortex, but not fast enough to cause splashing or foaming).

Inject 0.3 to 0.4 mL intravenously within 1 hour after the mixture is prepared (if you wait too long, the cellulose will swell and be difficult to inject).

Physiological Evaluation of Cellulose in Anesthetized Broilers. Male broilers (2691±22 g BW, n=7) were prepared at 46 to 47 d of age using surgical protocols described previously (Wideman and Kirby, 1995b; Wideman et al., 1996, 1998a, 1999). All birds had full access to feed and water until they were anesthetized. A light surgical plane of anesthesia was induced with intramuscular injections of allobarbital (5,5-diallyl-barbituric acid;[2] 25 mg kg/BW). The birds were fastened in dorsal recumbency on a surgical board thermostatically regulated to maintain a surface temperature of 30 C. An incision was made to open the thoracic inlet, a Transonic ultrasonic flowprobe[8] was positioned on the left pulmonary artery, the probe was connected to a Transonic T206 blood flow meter[8] to confirm signal acquisition, then the skin of the thoracic inlet was sealed with surgical wound clips. Silastic® Tubing (0.012 in I.D., 0.037 in O.D.)[3] filled with heparinized saline was inserted through the left cutaneous ulnar vein, and was advanced into the right pulmonary artery. The distal end of the cannula was attached to a blood pressure transducer interfaced through a Transbridge™ preamplifier[4] to a Biopac MP 100 data acquisition system[5] using AcqKnowledge software.[5] The right cutaneous ulnar vein was cannulated with PE-50 polyethylene tubing for systemic i.v. injections. The left brachial artery was cannulated with PE-50 polyethylene tubing filled with heparinized saline, the cannula was advanced to a position near the descending aorta, and was attached to a blood pressure transducer for continuous monitoring of systemic arterial pressure, and for collecting arterial blood samples. Intravenous infusions were not administered.

[2]Sigma Chemical Co., St Louis, Mo. 63178-9916.
[3]Konigsberg Instruments, Inc., Pasadena, Calif. 91107-3294.
[4]World Precision Instruments, Sarasota, Fla. 34230.
[5]Biopac Systems, Inc., Santa Barbara, Calif. 93117.
[8]Transonic Systems Inc, Ithaca, N.Y. 14850.

When surgical preparations were complete and a stabilization period of 10 min had elapsed, control data were collected for 10 min, and an arterial blood sample was collected within 5 min after the start of data recording (blood sample A). One mL of heparinized saline was injected i.v. as a volume control, data were collected for 10 min, and an arterial blood sample was collected within 5 min after the start of the volume control period (blood sample B). Microgranular CM-32 ion exchange cellulose[6] was mixed at 0.02 g/mL in heparinized saline (150 units ammonium heparin/mL of 0.9% NaCl)[2], and the mixture was vortexed continuously on a magnetic stirring plate to keep the particles suspended. The cellulose mixture was injected i.v. in volumes of 0.1, 0.2, and 0.2 mL (0.002, 0.004, and 0.004 g, respectively), data were recorded for 10 min after each injection, and arterial blood samples were collected within 5 min after each injection (blood samples C, D, and E). Each cellulose injection was immediately followed by 0.8 mL of heparinized saline to flush the cellulose through the wing vein cannula. Arterial blood (1 mL) was withdrawn anaerobically and injected within 30 s into a Radiometer ABL 330 Acid-Base Laboratory.[9] Appropriate function of the blood gas analyzer was assessed by periodically injecting Blood Gas Qualicheck® reference standards.[9] The primary arterial blood values for pH, partial pressure of $O_2$, and partial pressure of $CO_2$ were generated by the ABL330 operating at a sample chamber temperature of 37 C, and were recalculated by the ABL330 for a temperature of 41 C to match the normal body temperature of domestic fowl (Fedde, 1986). At the end of the experiment, the birds were killed with a 10 mL i.v. injection of 0.1 MKCl, and were dissected to obtain heart weights for calculating the RV:TV ratio.

[2]Sigma Chemical Co., St Louis, Mo. 63178-9916.
[6]Fisher Scientific, St Louis, Mo. 63178-4989.
[9]Radiometer America Inc., Wesoake, Ohio 44145.

The primary channels recorded by the Biopac MP 100 data acquisition system included systemic arterial pressure in millimeters of mercury (mm Hg), pulmonary arterial pressure (mm Hg), and blood flow through the left pulmonary artery (mL/min). Average values for these parameters were measured electronically during representative intervals at the start of data collection (Start), immediately preceding (sample intervals A1, B1, C1, D1, E1) and following (sample intervals A2, B2, C2, D2, E2) withdrawal of each arterial blood sample, immediately preceding each volume control or cellulose injection (sample intervals VC pre, 0.1 pre, 0.2 pre, and 0.2 pre), and during the maximum (Peak) pulmonary arterial pressure recorded within 60 s following each volume control or cellulose injection (sample intervals VC Peak, 0.1 Peak, 0.2 Peak, and 0.2 Peak). The protocol used for data averaging previously was demonstrated to accurately compensate for the influences of pulse pressure and respiratory cycles on pulmonary and systemic arterial pressures (Wideman et al., 1996a,b). These primary values were used to calculate cardiac output, stroke volume, pulmonary vascular resistance, and total peripheral resistance. Based on the assumption that cardiac output (mL/min) normally is divided approximately equally between the lungs, cardiac output was calculated as 2×blood flow. The cardiac output is the product of heart rate×stroke volume (mL/beat), consequently stroke volume was calculated as cardiac output divided by heart rate. Heart rate (beats/min) was obtained by counting systolic peaks over time in the pulmonary arterial pressure recording coincident with each sample interval. Assuming the pressure gradients across the pulmonary and systemic circulations are essentially equal to pulmonary arterial pressure and systemic arterial pressure, respectively (Wideman el al., 1996a,b, 1998a,b), then the relationships between pressure gradients, flow rates and resistances are summarized by the respective equations: pulmonary arterial pressure=cardiac output×pulmonary vascular resistance, and mean systemic arterial pressure=cardiac output×total peripheral resistance. Thus, pulmonary vascular resistance was calculated in relative resistance units as pulmonary aterial pressure (mm Hg) divided by cardiac output (mL/min), and total peripheral resistance was calculated in relative resistance units as mean systemic arterial pressure (mm Hg) divided by cardiac output (mL/min) (Besch and Kadono, 1978; Sturkie, 1986; Wideman et al., 1996, 1998a). Respiratory rate (breathsl/min) was obtained by counting the wave cycles associated with respiratory movement that comprise an integral part of the pulmonary arterial pressure recordings (Sturkie, 1986).

Physiological Evaluation of Sephadex in Anesthetized Broilers, Four male broilers (1080±64 g BW) were anesthetized at 28 to 32 d of age, and were prepared as described above for recording the pulmonary and systemic arterial pressures. Baseline data were collected for 10 to 20 min then a suspension of dextran polymer (Sephadex[2] G25–40 or G25–80, particle size range 10 to 80$\mu$; 0.02 g/mL in heparinized saline) was injected i.v. at 0.1 to 0.4 mL (0.002 to 0.008 g) per injection, with approximately 10 min allowed to elapse between injections. The Sephadex was mixed with heparinized saline immediately prior to each injection, and was vortexed continuously on a magnetic stirring plate to keep the particles in suspension. At the end of the experiment, the birds were killed with a 10 mL i.v. injection of 0.1 M KCl, and the lungs were fixed by immersion in 10% phosphate buffered formalin.

Evaluation of Low-Dose Cellulose and Sephadex in Unanesthetized Broilers The chronic responses of broilers to intravenous organic particulate injections were assessed in unanesthetized male broilers. They were weighed at 22 d of age, and either remained uninjected controls (n=10), or were injected with 0.5 mL of heparinized saline (volume controls, n=8), 0.1 mL of cellulose suspension (0.02 g/mL in heparinized saline, n=9), 0.2 mL of cellulose suspension (n=9), or 0.2 mL of the Sephadex suspension (0.02 g/mL in heparinized saline, n=10). The birds were returned to their environmental chamber until they reached 40 d of age, when they were weighed and oximetry values and heart rates were acquired from all surviving birds. A universal "C" sensor attached to a Vet/Ox™ 4403 pulse oximeter[7] was positioned on the wing to illuminate the tissue between the radius and ulna for measurements of percentage saturation of hemoglobin with oxygen and heart rate. The birds were euthanized with $CO_2$, the lungs of 14 birds (6 controls, 6 cellulose-injected, 6 Sephadex-injected) were fixed in 10% phosphate buffered formalin for histology, and the hearts of all birds were dissected to obtain ventricle weights for calculating the RV:TV ratio.

Evaluation of Medium-Dose Cellulose and Sephadex in Unanesthetized Broilers. Male broiler chicks hatched on Aug. 23, 1999 (Day 1) were weighed on Day 17, and remained uninjected controls (n=10), were injected with 0.5 mL heparinized saline (volume controls, n=10), or had a cellulose suspension (0.02 g cellulose/mL saline) injected into a wing vein at volumes of 0.2 mL (n=10), 0.25 mL (n=26), 0.3 mL (n=13), and 0.4 mL (n=15). Two of the birds in the 0.3 mL group and seven birds in the 0.4 mL group died within 30 min after the cellulose injections. The left lungs of seven of the birds that died were immersed in 10% phosphate buffered formalin for histology. On Day 19, blood and tissue samples were collected for immunology studies from two birds of each group except the 0.4 mL injection group. Additional birds from the same hatch were weighed on Day 22 (Sep. 13, 1999). A new lot of ammonium heparin[2] was used to prepare fresh heparinized saline (150 units heparin/mL 0.9% NaCl), which in turn was used to prepare suspensions of cellulose (0.02 g/mL) or Sephadex (0.02 g Sephadex G25–80/mL). The 22 d old broilers then were injected via a wing vein with the cellulose suspension at volumes of 0.3 mL (n=11) and 0.4 mL (n=10), or with the Sephadex suspension at 0.3 mL (n=10). One bird in the 0.4 mL cellulose group died 15 min after the injections. All surviving birds were maintained in environmental chambers until they reached 43 d of age. Oximetry values and heart rates were acquired at 40 d of age. A universal "C" sensor attached to a Vet/Ox™ 4403 pulse oximeter[7] was positioned on the wing to illuminate the tissue between the radius and ulna for measurements of percentage saturation of hemoglobin with oxygen and heart rate. At 43 d of age, the birds were weighed, euthanized with $CO_2$, and their hearts were dissected to obtain RV:TV ratios. Seven birds (2 controls, 5 injected with 0.25 or 0.3 mL cellulose) were injected i.v. with 10 mL of heparinized saline, euthanized 10 min later by cervical dislocation, and rapidly perfused through the right ventricle with 50 mL of 10% phosphate buffered formalin to fix the lungs in situ. The lungs were removed 30 min later and stored immersed in 10% phosphate buffered formalin Statistical Analysis Data were analyzed within a group overtime (across sample intervals) using the SigmaStat® Repeated Measures Analysis of Variance procedure, and means were differentiated by the Student-Newman-Keuls method (Jandel Scientific, 1994). Within a single sample interval across groups, the SigmaStat® T test was used to assess significant ($P \leq 0.05$) differences among means. The SigmaStat® linear regression procedure was used to evaluate relationships among cardiopulmonary variables. The SigmaStat® Z test was used to compare the incidence of ascites between groups.

Results and Discussion of Example 2

Figure 2:
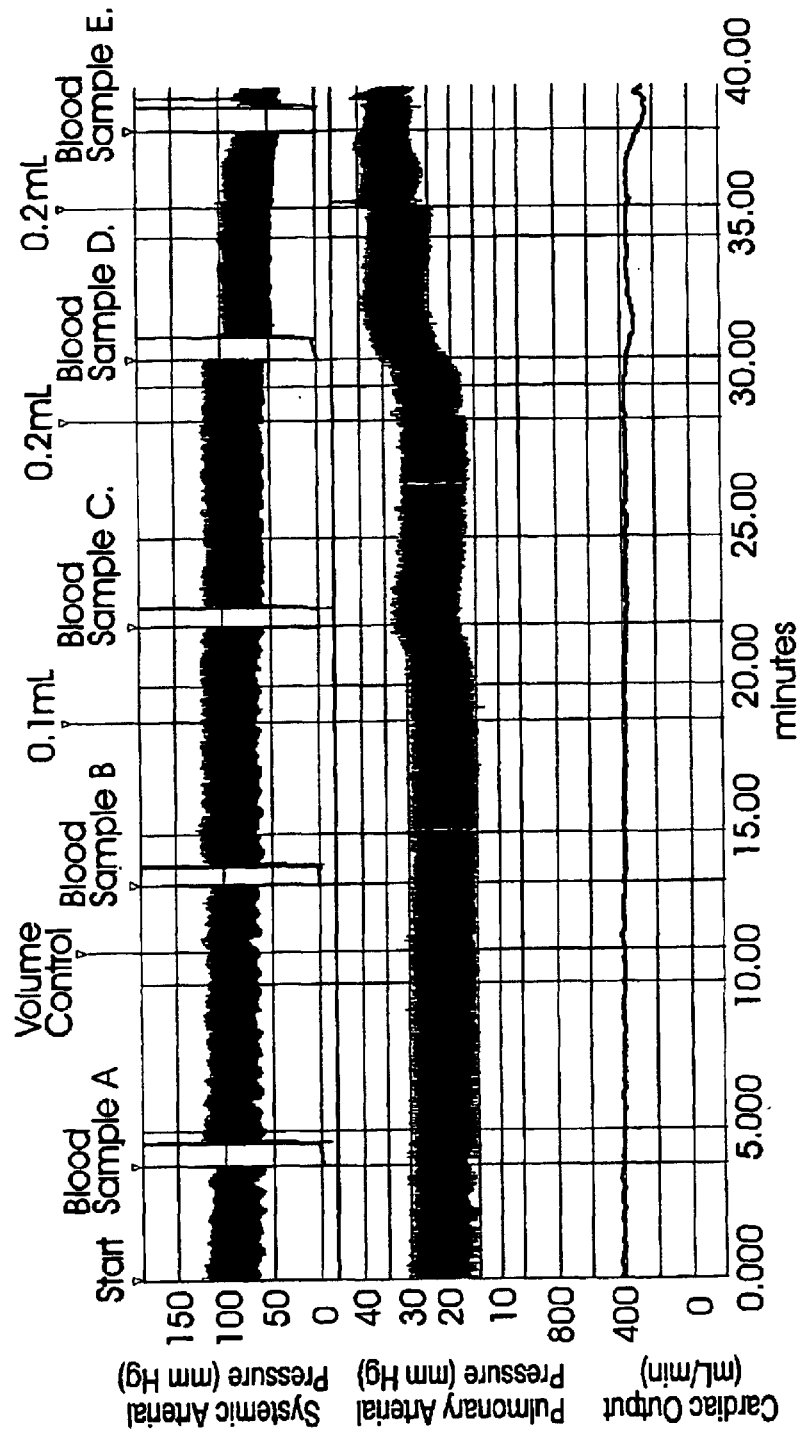
FIG. 2 is a physiograph recording of systemic arterial pressure (upper), pulmonary arterial pressure (middle), and cardiac output (lower) in a male broiler during sequential wing vein injections of 1 mL heparinized saline (volume control), or of microgranular cellulose (0.02 g cellulose/mL of heparinized saline) in volumes of 0.1, 0.2, and 0.2 mL. The gaps in the systemic arterial pressure tracing correspond with blood sample collections (1 mL each) from the brachial artery cannula for blood gas determinations. Arterial samples were collected 5 min after the start to the experiment (sample A), and within 5 min following each of the injections (samples B to E). The cardiac output data represent a direct tracing from a flow probe on the left pulmonary artery, with the Y-axis values doubled in this figure to represent the cardiac output flowing through both pulmonary arteries.
Figure 3:
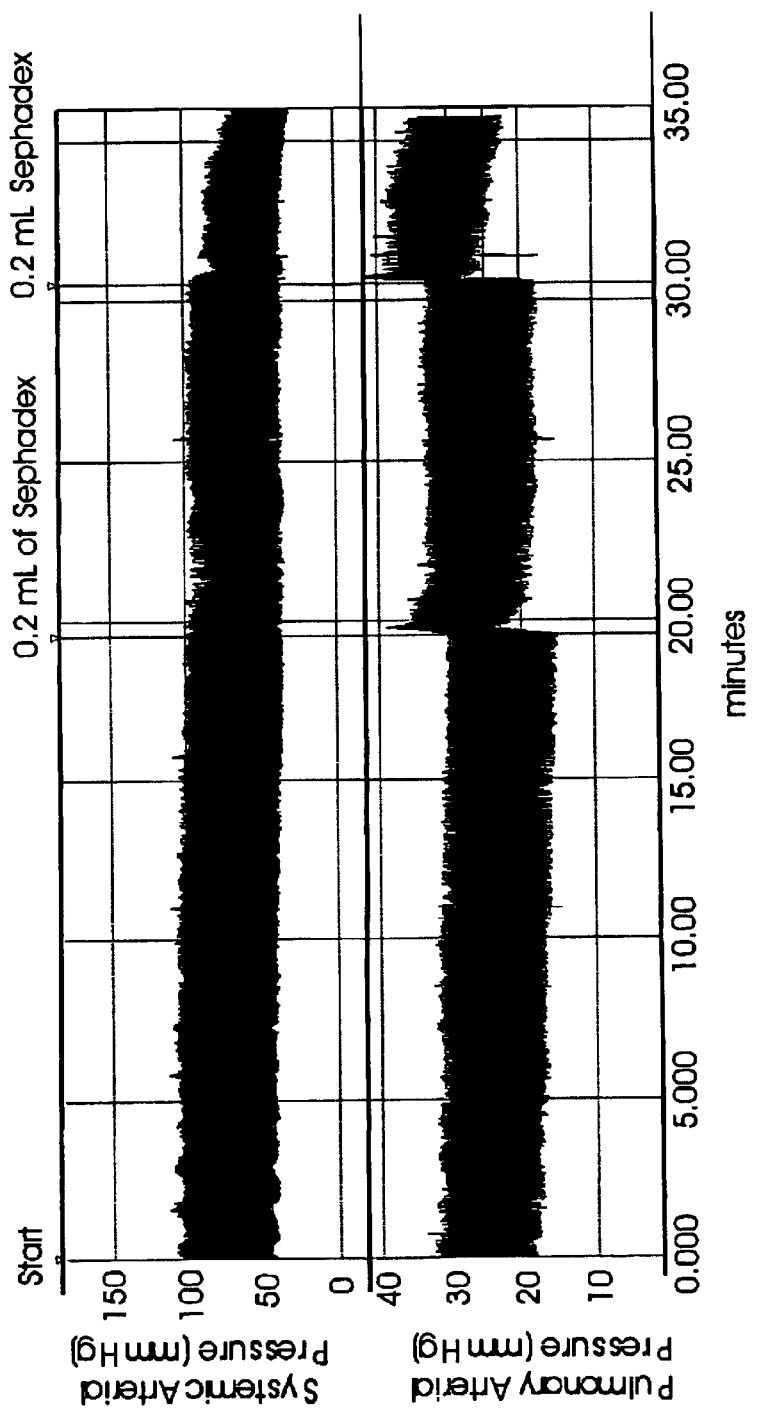
FIG. 3 is a physiograph recording of systemic arterial pressure (upper) and pulmonary arterial pressure (lower) in a male broiler during repeated 0.2 mL wing vein injections of Sephadex (0.02 g/mL of heparinized saline).

Physiological Evaluation of Cellulose and Sephadex in Anesthetized Broilers. As shown for an individual broiler in FIG. 2 (Pilot 4, 2550 g BW), the pulmonary arterial pressure initially averaged a consistent 23 mm Hg. Injecting 1 mL heparinized saline (Volume Control) did not influence any of the physiological variables. The 0.1 mL cellulose injection caused the pulmonary arterial pressure to increase to 25 mm Hg. The pulmonary arterial pressure increased to 28 mm Hg following the first 0.2 mL cellulose injection, and increased to 30 mm Hg after the second 0.2 mL cellulose injection. Both 0.2 mL cellulose injections triggered contemporaneous step-wise reductions in the mean systemic arterial pressure and cardiac output (FIG. 2). Typical responses to consecutive i.v. injections of the Sephadex suspension are shown for an individual broiler in FIG. 3. The pulmonary arterial pressure averaged 25 mm Hg during the 20 min pre-injection control period, increased by an average of 3 mm Hg after the first Sephadex injection, and then increased to 30 mm Hg following the second Sephadex injection. The systemic arterial pressure declined step-wise in response to the consecutive Sephadex injections (FIG. 3). Histopathological evaluations of lungs fixed within 30 min after the Sephadex injections revealed a sparse distribution of particles lodged in arterioles throughout the gas exchange regions, with clear evidence of lymphocytes aggregating on and around the particles.

Figure 4:
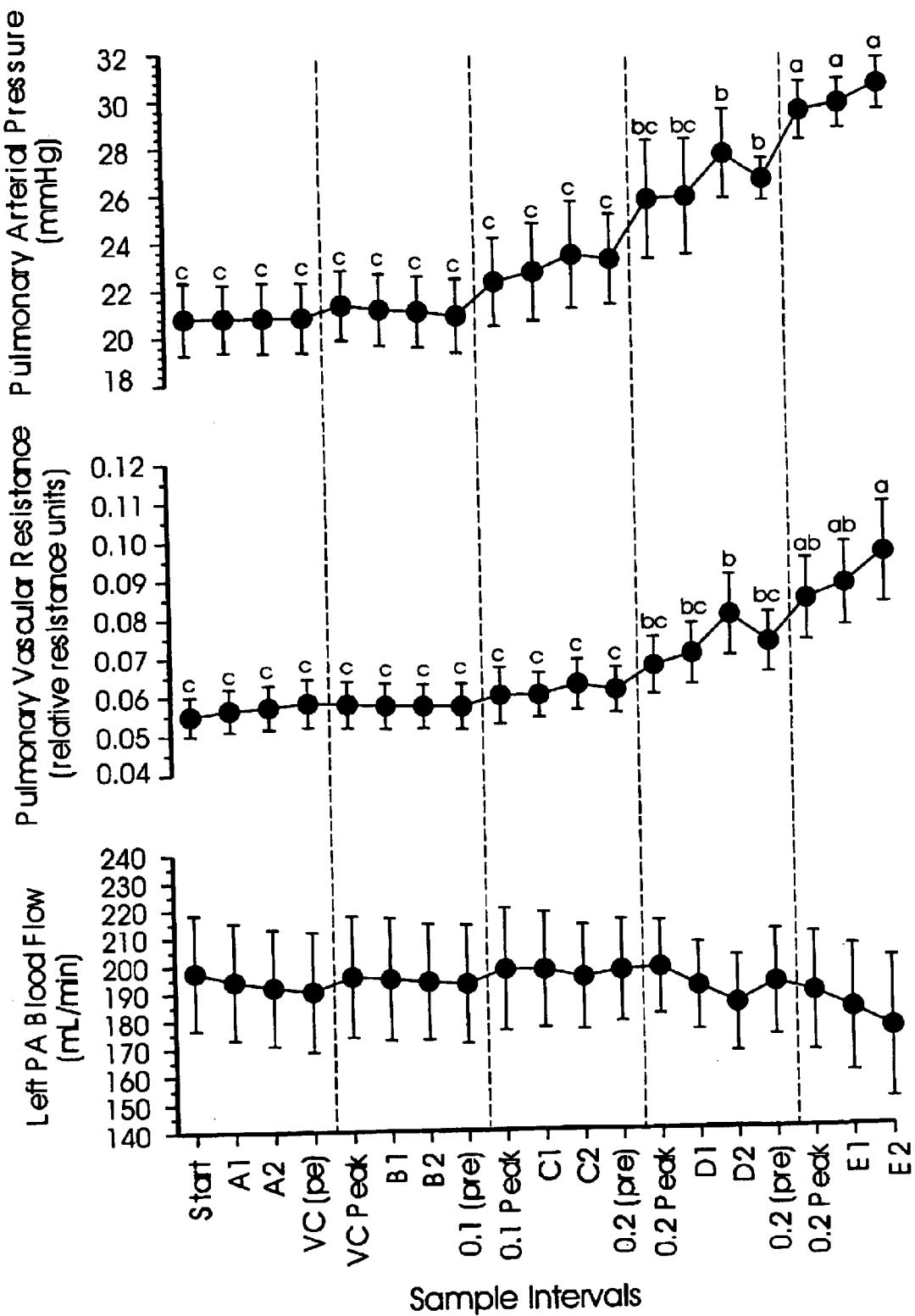
FIG. 4 is a graph showing pulmonary arterial pressure (upper panel), pulmonary vascular resistance (middle panel), and blood flow through the left pulmonary artery (lower panel) for male broilers (mean±SEM, n=7) at the start of data collection (Start), immediately preceding (sample intervals A1, B1, C1, D1, E1) and following (sample intervals A2, B2, C2, D2, E2) withdrawal of each arterial blood sample, immediately preceding each volume control or cellulose injection (sample intervals VC pre, 0.1 pre, 0.2 pre, and 0.2 pre), and during the peak pulmonary arterial pressure response within 60 s following each volume control or cellulose injection (sample intervals VC Peak, 0.1 Peak, 0.2 Peak, and 0.2 Peak). Different letters (a,b,c) designate differences between means over time ($P \leq 0.05$).
Figure 5:
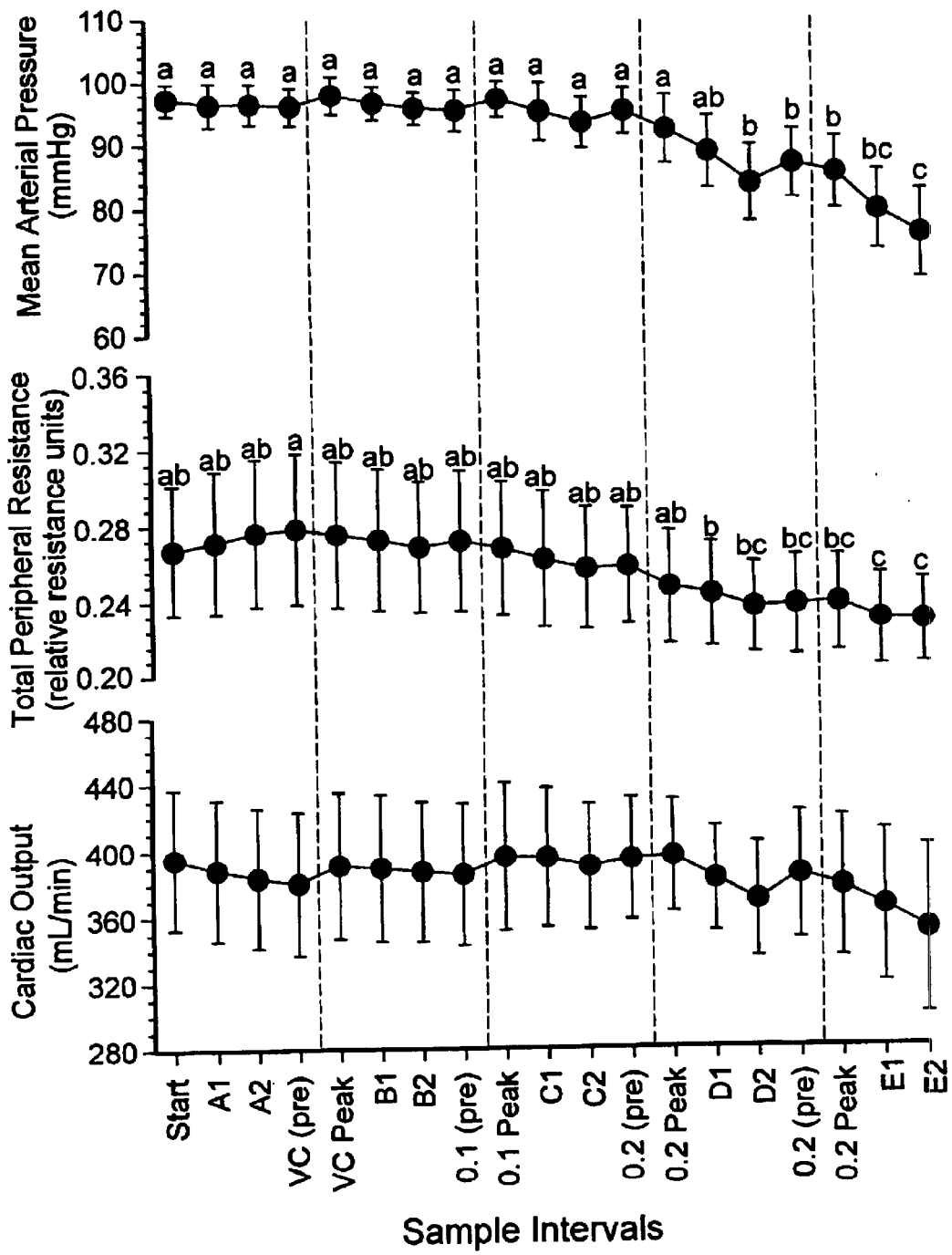
FIG. 5 is a graph showing mean systemic arterial pressure (upper panel), total peripheral resistance (middle panel), and cardiac output (lower panel) for male broilers (mean±SEM, n=7) at the start of data collection (Start), immediately preceding (sample intervals A1, B1, C1, D1, E1) and following (sample intervals A2, B2, C2, D2, E2) withdrawal of each arterial blood sample, immediately preceding each volume control or cellulose injection (sample intervals VC pre, 0.1 pre, 0.2 pre, and 0.2 pre), and during the peak pulmonary arterial pressure response within 60 s following each volume control or cellulose injection (sample intervals VC Peak, 0.1 Peak, 0.2 Peak, and 0.2 Pre). Different letters (a,b,c) designate differences between means over time ($P \leq 0.05$).
Figure 6:
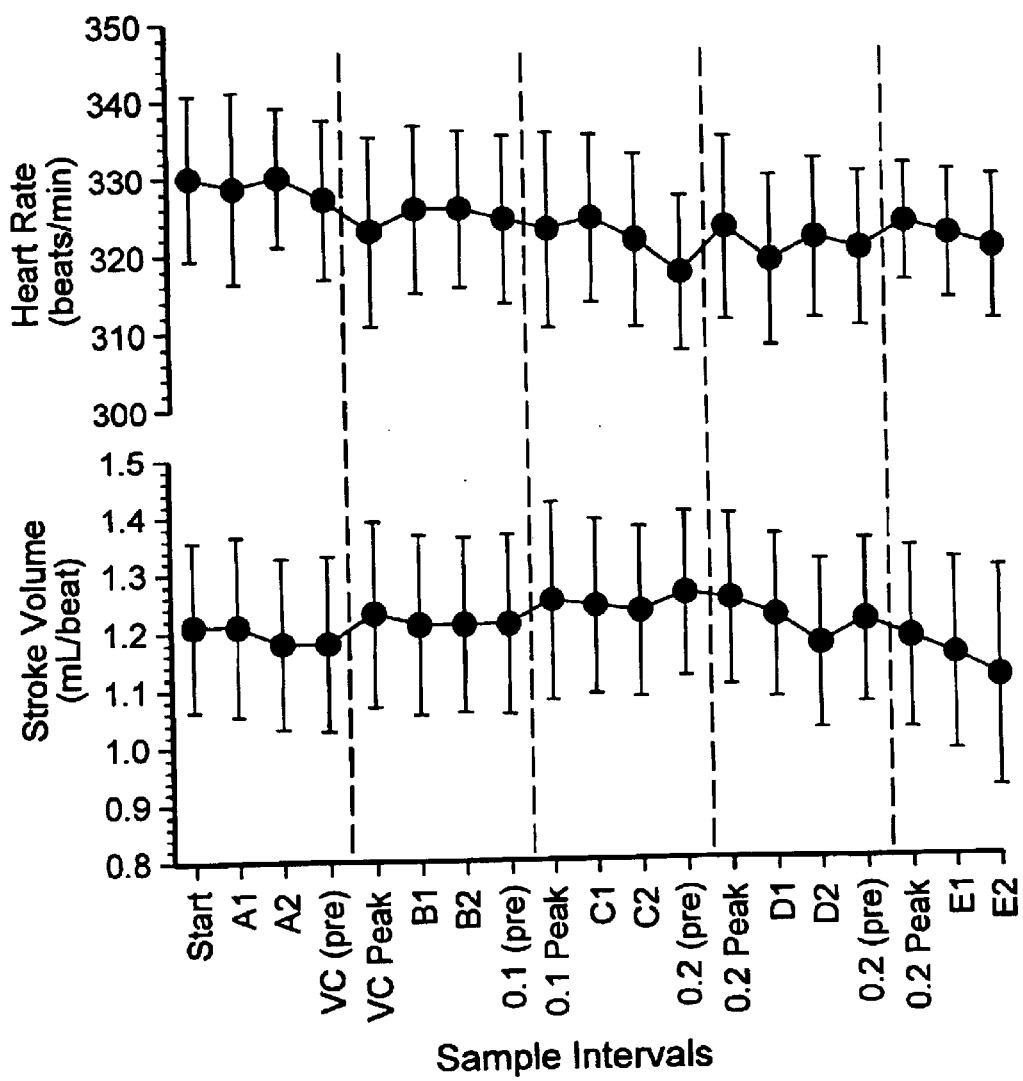
FIG. 6 is a graph showing heart rate (upper panel) and stroke volume (lower panel) for male broilers (mean±SEM, n=7) at the start of data collection (Start), immediately preceding (sample intervals A1, B1, C1, D1, E1) and following (sample intervals A2, B2, C2, D2, E2) withdrawal of each arterial blood sample, immediately preceding each volume control or cellulose injection (sample intervals VC pre, 0.1 pre, 0.2 pre, and 0.2 pre), and during the peak pulmonary arterial pressure response within 60 s following each volume control or cellulose injection (sample intervals VC Peak, 0.1 Peak, 0.2 Peak, and 0.2 Peak).
Figure 7:
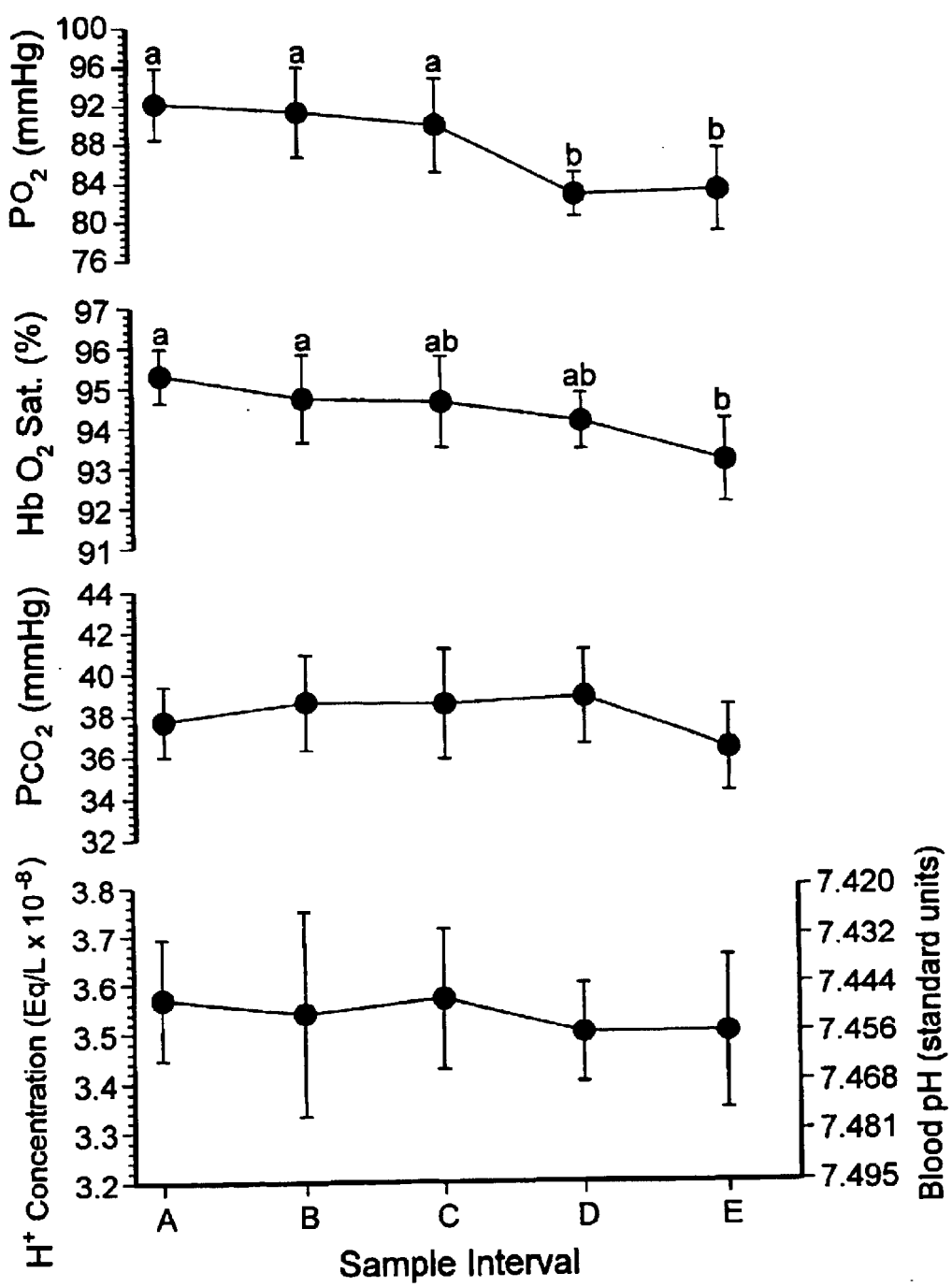
FIG. 7 is a graph showing partial pressure of $O_2$ (upper panel), saturation of hemoglobin with oxygen (second panel), partial pressure of $CO_2$ (third panel), and hydrogen ion concentration (lower panel) in arterial blood from male broilers (mean±SEM, n=7) within 5 min after the start of data collection (sample A), and within 5 min following a volume control injection (sample B) or cellulose injections (samples C, D, E). Different letters (a,b) designate differences between means over time ($P \leq 0.05$).

Group responses to i.v. cellulose injections are summarized in FIGS. 4 to 7. The pulmonary arterial pressure initially averaged 22 mm Hg, was unaffected by the volume control and 0.1 mL cellulose injections, but increased step-wise to values averaging 25 and then 29 mm Hg after the first and second 0.2 mL cellulose injections, respectively (FIG. 4). The increases in pulmonary arterial pressure were caused by vascular obstruction, as reflected by increases in the pulmonary vascular resistance that coincided with numerical (non-significant) reductions in blood flow through the left pulmonary artery (FIG. 4). Reductions in the mean systemic arterial pressure following the 0.2 mL cellulose injections were caused by corresponding reductions in total peripheral resistance, rather than by reductions in cardiac output (FIG. 5). Heart rate and stroke volume remained unchanged throughout the experiment (FIG. 6). The 0.2 mL cellulose injections obstructed a portion of the pulmonary vascular channels (increased pulmonary vascular resistance), and consequently caused the relatively unchanged cardiac output to flow more rapidly through the unobstructed channels. The resulting increase in the flow rate of red blood cells past the gas exchange surfaces revealed a modest diffusion limitation (West, 1993; Wideman and Tackett, 1999a,b) characterized by mild reductions in the arterial partial pressure of oxygen and the saturation of hemoglobin with oxygen (FIG. 7). Presumably it was this hypoxemia that triggered the contemporaneous systemic vasodilation (reduced total peripheral resistance) associated with the corresponding reduction in systemic arterial pressure (FIG. 5). The partial pressure of carbon dioxide and hydrogen ion concentration of arterial blood were unchanged by the cellulose injections, reflecting the much greater rate of diffusion for carbon dioxide crossing gas exchange surfaces (West, 1993). The respiratory rate did not change over the course of the experiment, averaging (mean±SEM) 51±3, 53±4, 53±4, 51±3, and 58±4 breaths/min at blood sample intervals A to E, respectively.

Evaluation of Low-Dose Cellulose and Sephadex in Unanesthetized Broilers. Unanesthetized birds injected via the wing vein with 0.2 mL of the cellulose suspension, or 0.2 mL of the Sephadex suspension, exhibited variable levels of acute respiratory distress and cyanosis. However, no mortality occurred during the wk following the injections. Data from the uninjected and saline-injected control groups did not differ, and were combined into a single control group for statistical analysis. The data for the 0.1 and 0.2 mL cellulose injected groups also were combined into a single cellulose group for statistical analysis. As shown in Table 2, ascites developed in one control and one cellulose-injected broiler. The body weight, ventricular weight, and physiological variables did not differ (P≧0.05) between the groups. The lack of group differences in RV:TV ratios, as well as absolute and BW-normalized right ventricular weight, indicate the doses of organic particulates injected into these unanesthetized birds were inadequate to occlude pulmonary blood vessels in proportions sufficient to trigger sustained pulmonary hypertension. These observations are consistent with the relatively minor and transient pulmonary hypertension responses to similar doses injected i.v. into anesthetized birds (FIGS. 2 and 3).

TABLE 2

Ascites incidence, final body weight, absolute and body weight-normalized ventricular weights, heart rate, and saturation of hemoglobin with oxygen in control broilers, broilers injected i.v. with low-dose suspensions of cellulose or sephadex (data are Means ± SEM for pooled Normal and Ascitic broilers).

| Variable | Experimental Groups | | | P |
|---|---|---|---|---|
| | Control (n = 18) | Cellulose (n = 18) | Sephadex (n = 10) | |
| Ascites Incidence, % | 5.5 (1/18) | 5.5 (1/18) | 0 (0/10) | ns |
| Final body weight (g) | 1918 ± 120 | 2144 ± 134 | 2022 ± 186 | 0.478 |

TABLE 2-continued

Ascites incidence, final body weight, absolute and body weight-normalized ventricular weights, heart rate, and saturation of hemoglobin with oxygen in control broilers, broilers injected i.v. with low-dose suspensions of cellulose or sephadex (data are Means ± SEM for pooled Normal and Ascitic broilers).

| Variable | Experimental Groups | | | P |
|---|---|---|---|---|
| | Control (n = 18) | Cellulose (n = 18) | Sephadex (n = 10) | |
| Right ventricle (g) | 2.34 ± 0.27 | 2.30 ± 0.22 | 2.73 ± 0.27 | 0.521 |
| Left ventricle + septum (g) | 5.92 ± 0.27 | 6.44 ± 0.51 | 6.82 ± 0.54 | 0.395 |
| Total ventricle (g) | 8.26 ± 0.43 | 8.74 ± 0.67 | 9.55 ± 0.68 | 0.384 |
| RV:TV ratio | 0.27 ± 0.02 | 0.26 ± 0.01 | 0.29 ± 0.02 | 0.626 |
| Right ventricle/BW | 0.0012 ± 0.0001 | 0.0012 ± 0.0001 | 0.0014 ± 0.0002 | 0.193 |
| Left ventricle + septum/BW | 0.0032 ± 0.0001 | 0.0032 ± 0.0001 | 0.0036 ± 0.0003 | 0.261 |
| Total ventricle/BW | 0.0044 ± 0.0001 | 0.0044 ± 0.0001 | 0.0050 ± 0.0004 | 0.089 |
| Heart rate (beats/min) | 391 ± 11 | 386 ± 10 | 405 ± 7 | 0.416 |
| Hb saturation with $O_2$, % | 82 ± 3 | 81 ± 2 | 81 ± 2 | 0.970 |

Histopathological evaluations revealed sparse intrapulmonary distributions of cellulose and Sephadex particles, with the particle density appearing to be roughly proportional to the volumes of cellulose or Sephadex injected. As an initial estimate, under 10% of the arterioles in the gas exchange region contained particles at the 0.2 mL injection dose. The Sephadex particles appeared to have been largely digested by macrophages, and had triggered intense foci of lymphocytic infiltration. The cellulose particles remained reasonably distinct in outline, but clearly were engulfed by macrophages, and clearly were ringed by intense lymphocytic foci.

Evaluation of Medium-Dose Cellulose and Sephadex in Unanesthetized Broilers. Nine birds were removed from the data set because they died of causes other than ascites, including necrotic enteritis (one control and two each from the 0.25 mL and 0.4 mL cellulose groups), bad legs (one from the 0.3 mL cellulose group), and sudden death syndrome (three from the 0.3 mL cellulose and Sephadex groups). The use of a fresh lot of ammonium heparin for the Day 22 injections eliminated most of the mortality that previously had been caused by injecting 0.3 to 0.4 mL of the 0.02 g/mL cellulose suspension on Day 17. The apparent improvement in short term viability achieved by using improved heparin titers is consistent with previous observations that anesthetized and cannulated (well heparinized) broilers were more tolerant of micro-particulate injections than unanesthetized, an uncannulated broilers. Presumably one unintended side effect of micro-particulate injection is to initiate the formation of blood clots that considerably amplify the degree of vascular obstruction. Indeed, histopathological evaluations of the lungs from seven birds that died immediately after 0.3 or 0.4 mL cellulose injections revealed clusters of erythrocytes adhering to the cellulose particles. In addition, individual lymphocytes or small clusters of lymphocytes adhered to the cellulose particles lodged in the pulmonary arterioles.

Figure 8:
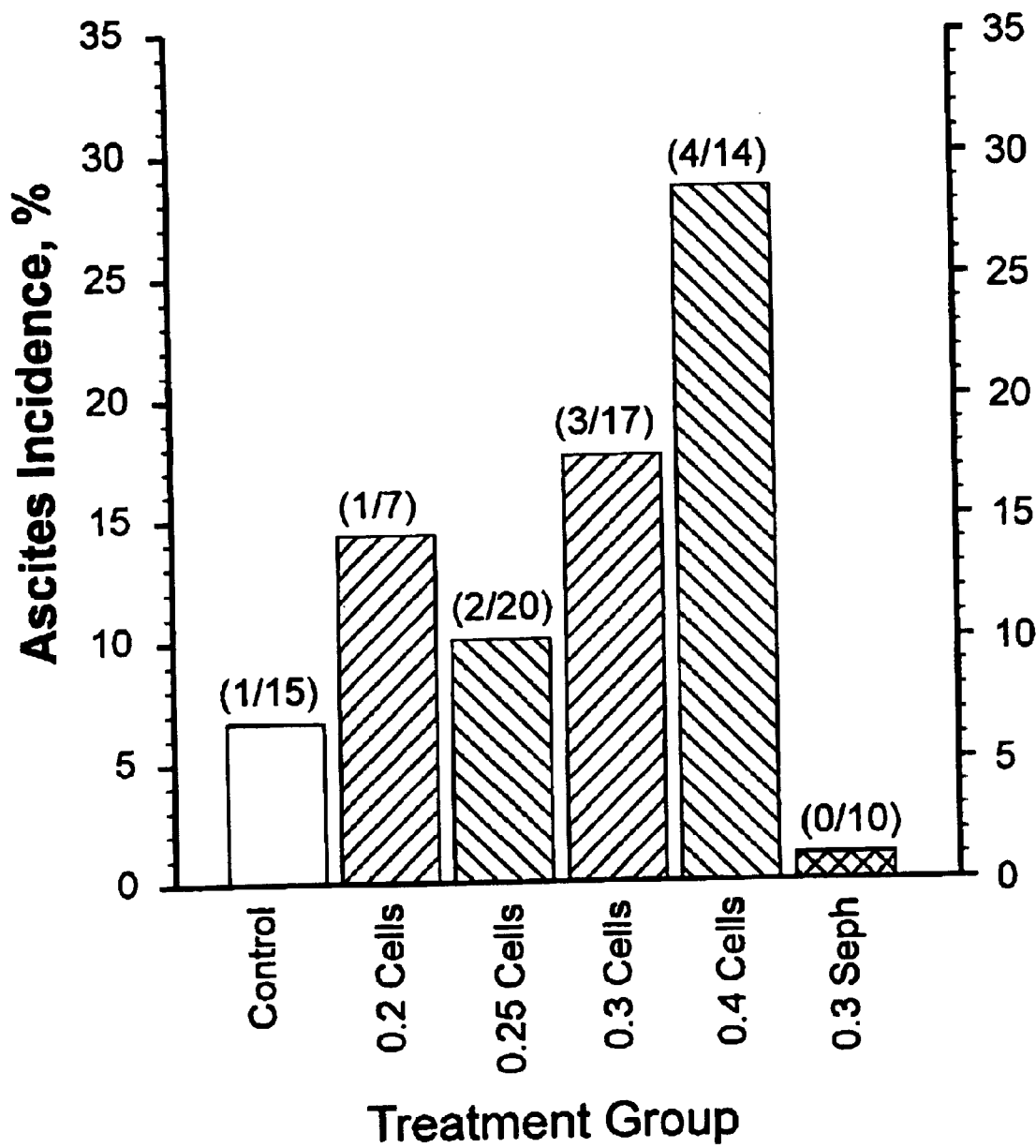
FIG. 8 is a graph showing cumulative incidence of ascites at 43 d of age in Control broilers, broilers injected i.v. with 0.2, 0.25, 0.3, or 0.4 mL of cellulose suspension, or broilers injected i.v. with 0.3 mL of Sephadex suspension at 17 to 22 d of age. Numbers in parentheses reflect the number developing ascites/total number available for evaluation.

The cumulative (Day 17 to 43) incidence of ascites for each treatment group is illustrated in FIG. 8. One uninjected control and none of the saline injected controls developed ascites, consequently these groups were pooled into an overall control category. The ascites incidence did not differ among the groups according to the Z test, however the ascites incidence was numerically proportional to the volume of cellulose particles injected (FIG. 8). For further statistical evaluation, the cellulose groups were pooled into low dose (0.2+0.25 mL) and medium-dose (0.3+0.4 mL) categories, as shown in Table 3. A numerical proportionality again is apparent between the ascites incidence and the volume of cellulose injected. For the broilers diagnosed as normal on Day 43, the Control group had the highest final body weight, but none of the other variables differed among the groups for these normal broilers. Interestingly, the 0.3 mL Sephadex injections did not trigger ascites, but did result in the lowest final body weight and numerically the lowest oximetry value for all the groups (Table 3).

TABLE 3

Ascites incidence, final body weight, absolute and body weight-normalized ventricular weights, heart rate, and saturation of hemoglobin with oxygen in control broilers (pooled uninjected + saline injected), broilers injected i.v. with suspensions of cellulose (pooled 0.2 and 0.25 mL; pooled 0.3 and 0.4 mL), or 0.3 mL sephadex (data are Means ± SEM of broilers that remained Normal to Day 43).

| | Experimental Groups | | | | |
|---|---|---|---|---|---|
| Variable | Control (n = 14) | Cellulose 0.2 + 0.25 mL (n = 24) | Cellulose 0.3 + 0.4 mL (n = 24) | Sephadex 0.3 mL (n = 10) | P |
| Ascites Incidence, % | 6.7 (1/15) | 11.1 (3/27) | 22.5 (7/31) | 0 (0/10) | 0.278 |
| Final body weight (g) | 2658 ± 38 | 2603 ± 34 | 2513 ± 40 | 2496 ± 59 | 0.042 |
| Right ventricle (g) | 2.90 ± 0.24 | 2.65 ± 0.14 | 2.56 ± 0.12 | 2.73 ± 0.48 | 0.544 |
| Left ventricle + septum (g) | 7.24 ± 017 | 7.58 ± 0.13 | 7.31 ± 0.16 | 7.23 ± 0.29 | 0.405 |
| Total ventricle (g) | 10.13 ± 0.28 | 10.22 ± 0.20 | 9.87 ± 0.20 | 9.96 ± 0.38 | 0.664 |
| RV:TV ratio | 0.28 ± 0.02 | 0.26 ± 0.01 | 0.26 ± 0.01 | 0.27 ± 0.01 | 0.383 |
| Right ventricle/BW | 0.0011 ± 0.0001 | 0.0010 ± 0.0001 | 0.0010 ± 0.0001 | 0.0001 ± 0.0002 | 0.705 |
| Left ventricle + septum/BW | 0.0027 ± 0.0001 | 0.0029 ± 0.0001 | 0.0029 ± 0.0001 | 0.0029 ± 0.0003 | 0.183 |
| Total ventricle/BW | 0.0038 ± 0.0001 | 0.0039 ± 0.0001 | 0.0040 ± 0.0001 | 0.0040 ± 0.0003 | 0.652 |
| Heart rate (beats/min) | 386 ± 7 | 386 ± 6 | 383 ± 7 | 384 ± 7 | 0.986 |
| Hb saturation with $O_2$, % | 83.5 ± 2.2 | 81.1 ± 1.2 | 81.9 ± 1.6 | 77.7 ± 3.2 | 0.340 |

Figure 9:
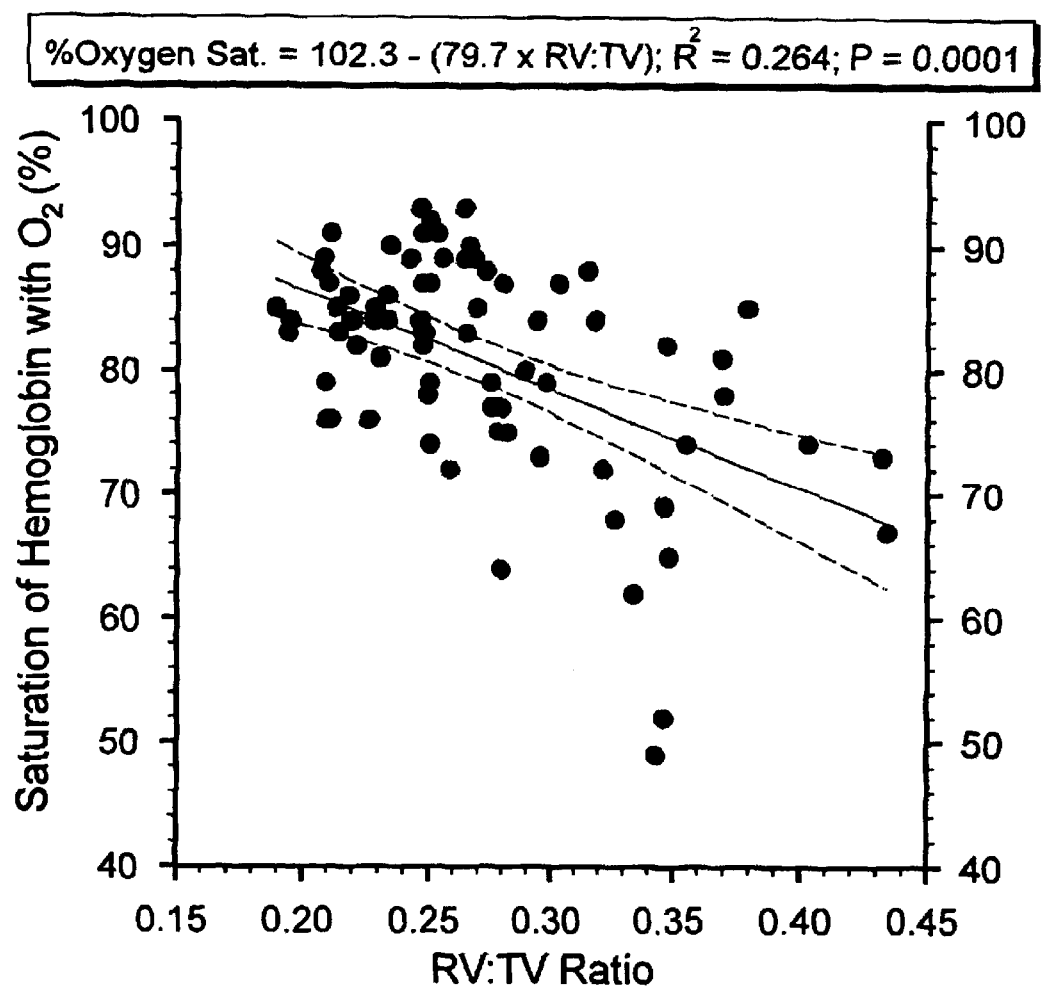
FIG. 9 is a scattergram showing relationship between the saturation of hemoglobin with oxygen on Day 40 vs. the RV:TV ratio on Day 43 for individual broilers (all groups pooled). Solid line shows the linear regression line (equation provided), and the dashed line shows the 95% confidence limits.
Figure 10:
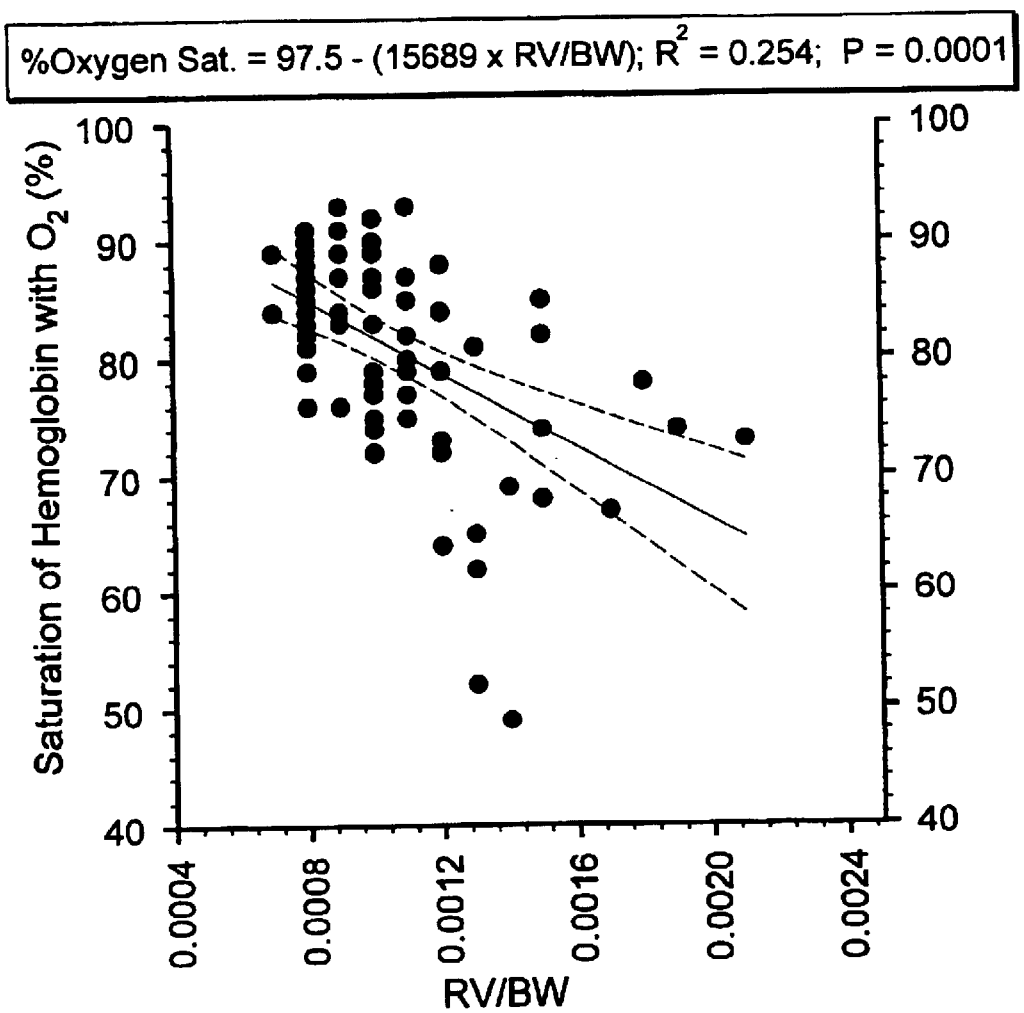
FIG. 10 is a scattergram showing relationship between the saturation of hemoglobin with oxygen on Day 40 vs. the right ventricle weight (g) normalized for final BW (g) on Day 43 for individual broilers (all groups pooled). Solid line shows the line regression line (equation provided), and the dashed line shows the 95% confidence limits.

Linear regression equations comparing oximetry values with final body weight, the RV:TV ratio, and absolute or BW-normalized ventricle weights are shown in Table 4. The oximetry values were consistently negatively correlated with the RV:TV ratio (Table 4, FIG. 9) and the BW-normalized right ventricle weight (Table 4, FIG. 10).

TABLE 4

Linear regression equations, Pearson correlation coefficients (r), coefficients of determination ($r^2$), and probability (P) values for relationships between the pulse oximeter values for the saturation of hemoglobin with oxygen ($HbO_2$ %) versus final BW, RV:TV ratios, and absolute or BW normalized ventricle weights (g/g)

| $HbO_2$ Saturation (%) vs. Variables[2] | Equation | r | $r^2$ | P |
|---|---|---|---|---|
| $HbO_2$ % vs. final body weight (BW) | $HbO_2$ % = +0.0104 BW + 54 | 0.309 | 0.096 | 0.0065 |
| $HbO_2$ % vs. RV:TV ratio | $HbO_2$ % = 31 79.7 RV:TV + 102 | 0.514 | 0.264 | 0.0001 |
| $HbO_2$ % vs. RV weight | $HbO_2$ % = −3.98 RV + 92 | 0.322 | 0.104 | 0.0222 |
| $HbO_2$ % vs. TV weight | $HbO_2$ % = +0.604 TV + 75 | 0.085 | 0.007 | 0.4635 |
| $HbO_2$ % vs. LV + S weight | $HbO_2$ % = +3.00 LVS + 59 | 0.338 | 0.114 | 0.0028 |
| $HbO_2$ % vs. RV weight/final BW ratio | $HbO_2$ % = −15689 RV/BW + 98 | 0.504 | 0.254 | 0.0001 |
| $HbO_2$ % vs. TV weight/final BW ratio | $HbO_2$ % = −5278 TV/BW + 102 | 0.226 | 0.051 | 0.0498 |
| $HbO_2$ % vs. LV + S weight/final BW ratio | $HbO_2$ % = +5301 LVS/BW + 66 | 0.189 | 0.036 | 0.1165 |

These correlations obtained under normal temperature conditions using control and particle-injected broilers con firm the association between right ventricular hypertrophy, pulmonary hypertension, and the diffusion limitation of the lung (inadequate pulmonary vascular capacity).

Example 3

Comparisons of Male Broilers from a Base Population and the 2nd and 3rd Generations of an Ascites Resistant Line: Responses to Cool Temperatures and Intravenous Particle Injections Ascites occurs worldwide in broiler chickens reared under a variety of conditions. An elevated blood pressure within the pulmonary circulation (pulmonary hypertension) initiates a distinctive pathophysiological progression that includes the sequential development of hypoxemia, right-sided congestive heart failure, central venous congestion, cirrhosis of the liver, and transudation of ascitic fluid into the abdominal cavity. Consequently, the terms pulmonary hypertension syndrome (PHS) and ascites syndrome are widely accepted as synonyms. Our research has confirmed the core hypothesis that PHS-susceptible broilers have an inherent potential to "outgrow" their cardio-pulmonary capacity (Wideman and Bottje, 1993). In this context, cardio-pulmonary capacity is defined as the ability of the pulmonary circulation to accept the requisite cardiac output at blood flow rates and pressures that are sufficiently low to avoid triggering pulmonary hypertension and systemic hypoxemia The pulmonary circulation includes the right ventricle of the heart and blood vessels of the lungs (pulmonary vasculature). According to the equation PAP=CO×PVR, right ventricular work and pulmonary arterial pressure must increase to propel a normal cardiac output through the lungs whenever the pulmonary vasculature is anatomically inadequate or inappropriately constricted, or when the viscosity of the blood increases. Right ventricular work and pulmonary arterial pressure also must increase whenever an increase in cardiac output cannot be accommodated through compensatory mechanisms known to reduce the pulmonary vascular resistance in mammals, such as flow-dependent pulmonary vasodilation and the recruitment of previously un- or under-perfused vascular channels. If the existing vascular channels have a low compliance and are fully engorged with blood at a normal cardiac output, then further increases in cardiac output can only be accomplished by increasing the rate at which blood flows through the vasculature. It takes time for $O_2$ to diffuse across the gas exchange barrier and into red blood cells. Therefore, hypoxemia ensues when rapidly flowing red blood cells do not reside at the gas exchange surfaces long enough to achieve full saturation of the hemoglobin with $O_2$ (Wideman and Bottje, 1993).

Occluding one pulmonary artery directly increases the pulmonary vascular resistance and forces the right ventricle to elevate the pulmonary arterial pressure to propel the cardiac output through the unoccluded lung. The acute and chronic responses to unilateral pulmonary artery occlusion mirror the pathophysiological progression observed in broilers spontaneously developing ascites under a variety of environmental and management conditions, providing support for the hypothesis that increases in the cardiac output or pulmonary vascular resistance constitute common mechanisms through which multiple factors can initiate PHS. Chronic unilateral pulmonary artery occlusion triggers a high incidence of ascites. Survivors of chronic unilateral pulmonary artery occlusion apparently possess a cardiopulmonary capacity sufficient to accommodate the combined challenges of a disproportionately high cardiac output and an elevated pulmonary vascular resistance.

Chronic unilateral pulmonary artery occlusion provides a highly effective tool for rigorously eliminating PHS-susceptible individuals, thereby selecting for broad-based ascites resistance. Broiler breeders that thrived in spite of having one pulmonary artery occluded, subsequently produced first generation male and female progeny exhibiting a $\geq 50\%$ reduction in the incidence ascites when grown as rapidly as possible during exposure to cool temperatures. Furthermore, growth performance was minimally affected in attaining this improved ascites resistance, in spite of the fact that the breeder parent line for the chicks of the Base population (controls) had experienced an additional generation of selection for growth that necessarily could not be imposed on the breeder parents for the Resistant chicks (Wideman and French, 1999). A second generation of this ascites-resistant line again was selected survivors of unilateral pulmonary artery occlusion, and additional improvements were achieved in ascites resistance during cool temperature exposure with a minimal impact on growth (Wideman and French, 2000). The dramatic improvement in ascites resistance within two generations of selection confirms that the anatomical or metabolic capacity of the pulmonary vasculature to accommodate an increase in blood flow is crucial to the ability of broilers to resist the onset of pulmonary hypertension leading to ascites. The gene or genes involved in ascites as susceptibility appear to be dominant, indicating that ongoing proactive exposure and elimination of susceptible individuals will be necessary to achieve an overall improvement in ascites resistance.

The unilateral pulmonary artery occlusion technique is impractical for large-scale genetic selection programs, because considerable time and surgical expertise are required to correctly clamp the pulmonary artery. More efficient methodologies for triggering controlled, sustainable increases in pulmonary vascular resistance are needed before dominant genes responsible for ascites susceptibility can be routinely eliminated from commercial broiler populations. Recent pilot studies have confirmed that intravenously injected micro-particles are carried by the returning venous blood to the lungs, where the particles become lodged in the pulmonary micro-vasculature. Physical occlusion of the pulmonary micro-vasculature, in proportion to the number of particles injected, provides a potential means for efficiently creating a controllable, sustained increase in pulmonary vascular resistance leading to the onset of pulmonary hypertension and the elimination of susceptible broilers (Wider, unpublished observations).

Objective 1.

Step-wise improvements in ascites resistance previously were demon sated through two generations of selection using the pulmonary artery clamp technique. One objective of the present example determines that a third generation of selection using the pulmonary artery clamp technique yielded further improvement in ascites resistance.

Objective 2.

If the micro-particle injection technique is to be substituted with confidence for the unilateral pulmonary artery occlusion technique, it is essential to know if similar subsets of broilers are resistant to unilateral pulmonary artery occlusion and micro-particle injections. Accordingly, we tested the hypothesis that, if both micro-particle injections and unilateral pulmonary artery occlusion select for a superior pulmonary vascular capacity, then progeny from the ascites-resistant line should be more resistant to micro-particle injections than progeny from the base population Materials and Methods The derivation of the $1^{st}$ generation ascites-resistant line from the Base population, and the $2^{nd}$ generation Resistant line from the $1^{st}$ generation Resistant line, have been described previously (Wideman and French, 1999, 2000). For the present study, male and female progeny from the $2^{nd}$ generation Resistant line were subjected to selection using the unilateral pulmonary artery occlusion technique, as described previously (Wideman and Kirby, 1995, 1996; Wideman et al., 1997). Survivors that remained clinically healthy at 42 d of age were subjected to partial feed restriction consistent with standard industry practice, and were reared to breeding age to comprise the $3^{rd}$ generation Resistant line. Additional progeny from the original $2^{nd}$ generation Resistant line were reared to maturity without further selection for ascites resistance during the intervening year, and served as the parents for the $2^{nd}$ generation Resistant chicks evaluated in the present study.

Male chicks from the Base and Resistant lines were hatched at the Hubbard ISA Research Hatchery on Jan. 7, 200. The chicks were wing-banded and shipped to the University of Arkansas Poultry Research Farm on the day of hatch (Day 1). They were placed on fresh wood shavings litter in 8 environmental chambers (8 m$^2$ floor space) in the Poultry Environmental Research Lab. They were brooded at 33° C. on Days 1–5, 29° C. on Days 6–10, and 27° C. on days 11–17. Thereafter, the birds in chambers 1–4,7,8, and 10 were challenged with sub-thermoneutraltemperatures (14–15° C.) until the experiment terminated on Day 49. The birds in chamber 9 were maintained at 21° C. until the experiment was terminated. The photoperiod was 24 h of light on Days 1–5, and 23 h light/1 h dark thereafter. Feed and water were provided for ad libitum consumption. Water was provided in Plasson waterers due to prior experience that nipple waterers markedly reduce the incidence of PHS (Wideman et al., 1998). A com-soybean meal-based broiler ration formulated to meet or exceed the minimum NRC (1984) standards for all ingredients, including 22.7% CP, 3,059 kcal ME/kg, 1.5% arginine, and 1.43% lysine, was provided as crumbles during Weeks 1 and 2, then the same ration was provided as pellets thereafter.

Particle Injections. Micro-granular CM-32 ion exchange cellulose was mixed at 0.02 g/mL in heparinized saline (200 units ammonium heparin/mL of 0.9% NaCl). The mixture was vortexed continuously on a magnetic stirring plate to keep the particles suspended. Within 1 hour after mixing, the cellulose was injected into a wing vein using a 1 mL tuberculin syringe and a 22 gauge needle. On Day 20, all birds in chamber 9 (normal temperature chamber) were weighed and injected with 0.4 mL of the cellulose suspension, regardless of body weight. On Day 21, all birds in chamber 4 (cool temperature chamber) were weighed and injected with 0.3 mL of the cellulose suspension, regardless of body weight. On Days 47 to 48, all birds remaining in chambers 8, 1, and 2 (cool temperature chambers) were injected with 0.8 mL of the cellulose suspension, regardless of body weight Individual body weights were recorded on Day 17 (or as described above) and again at the time of necropsy (final BW). Necropsies were conducted on all mortality after day 17, as well as on all birds surviving to the end of the experiment Birds were euthanized with $CO_2$ gas, and the heart was removed, dissected and weighed for calculation of the right:total ventricular weight V:TV) ratio as an index of pulmonary hypertension (Burton et al., 1968; Cueva et al., 1974; Sillau et al., 1980; Huchzermeyer er al., 1988; Peacock et al., 1989). A diagnosis of ascites was recorded only when ascitic fluid accumulation was evident or when a plasma clot adhered to the surface of the liver. Birds were deleted from the data sets when they were culled for poor growth (runts) or leg problems, or when they died from causes other than PHS.

Statistical Analysis. The PHS incidences and incidences of ≦24 hour post-injection mortality were evaluated using a z-test (SigmaState®, Jandel Scientific, 1994). Other parameters were analyzed by ANOVA or ANOVA on ranks using the Student-Newman-Keuls method or Dunn's method. where appropriate, for means separation tests (SigmaStat®, Jandel Scientific, 1994).

Results and Discussion of Example 3

Certain birds were excluded from the experiment. These include pre-Day 21 mortality and culls (57 from the Base Population=Gold wing bands; 30 from the Resistant Population=Yellow wing bands), as well as broilers removed from the data analysis (13 each from the Base and Resistant populations) because they died or were culled for reasons other than ascites (flipover, bad legs, necrotic enteritis, etc.). Bird assignments were by chamber after Day 17. Of particular note was one group, in which substantial necrotic enteritis mortality (treated with Bacitracin in the drinking water) was followed by substantial flipover mortality. The unique pattern of this group gave the impression that an excessive number of Resistant birds developed flipover. Aside from this group, overall non-ascitic mortality appears to be proportionally distributed among the Base and Resistant populations. The flipover incidence in the Resistant line deserves ongoing attention.

Ascites incidences for males in all previous comparisons of Base vs. Resistant populations (Wideman and French, 1999, 2000) as well as the present experiment are summarized. The Base population exhibits a consistent annual trend toward lower ascites susceptibility when exposed to very similar cool temperature challenges in our environmental chambers. Subdividing the yellow wing banded birds into the $2^{nd}$ generation Resistant line (GEN 2R) and $3^{rd}$ generation Resistant line (GEN 3R) revealed no further improvement in ascites resistance within the limited number of $3^{rd}$ generation birds evaluated. Evidently we now have approached the effective limit of the pulmonary artery clamp technique for reducing ascites susceptibility. For subsequent data analysis, these GEN 2R and GEN 3R groups were pooled as a single Resistant group. We compared data for all birds, regardless of chamber, that were exposed to cool temperatures and subsequently developed ascites or remained nonascitic.

Overall comparisons of ascitic and nonascitic broilers from the Base and Resistant populations were determined. The Day 17 BW was not predictive of the males within a line that subsequently developed ascites. Resistant males tended to have a lighter body weight (BW) on Day 17, suggesting a tendency toward slower early growth than the Base males. The final BW and BW gain for nonascitic birds did not differ between the Base and Resistant males (P=0.1 1). The modest numerical difference in final BW cannot account for the very large difference in ascites susceptibility between the Base and Resistant populations. Within both lines, the final BW and BW gain were consistently lower for ascitic than for nonascitic broilers. This observation is consistent with previous observations that the onset of hypoxemia and pulmonary hypertension cause growth to decelerate. The lower RV:TV ratio and relative right ventricular mass (RV/BW) of Resistant nonascitic males when compared with Base nonascitic males indicates the right ventricle of the Resistant population performed less work (right ventricular work∝pulmonary arterial pressure×cardiac output) than the right ventricle of the Base population.

The data for individual birds (maintained at a normal temperature and injected on Day 20 with 0.4 ml of cellulose particles) were evaluated, and the results summarized. The 0.4 mL injection dose previously was shown to cause an acute, sustained increase in pulmonary arterial pressure and pulmonary vascular resistance (Wideman, unpublished). The Base population was highly susceptible to particle injection, as 41.9% of the males did not have sufficient pulmonary vascular capacity to survive this level of particle injection for $\leq24$ hours. Another 23.2% of the injected Base population males subsequently developed ascites by Day 43, when all surviving birds were necropsied. In contrast, only 6.25% of the Resistant population males died within the 24 hours post-injection (P=0.04 compared with Base), and only 6.25% of the Resistant males subsequently developed ascites (P=0.055 compared with Base). The body weight of Base population birds that died $\leq24$ hours post-injection was lower (P$\leq$0.05) on Day 20 than for Base population birds that survived and did not develop ascites (667±25 vs. 738±13). The Day 20 body weight of Resistant line survivors (651±14) was lower than that of Base population survivors, but not lower than that of Base population susceptible individuals. The comparisons within the Base population suggest a body weight×injection dosage interaction may exist (presumably in proportion to pulmonary vascular development). In contrast the Base vs. Resistant line comparisons reveal no compelling need to incorporate the time consuming step of normalizing each particle injection dose for individual differences in body weight.

The data for individual birds maintained at a cool temperature and injected on Day 21 with 0.3 ml of cellulose particles were evaluated, and the results summarized. The lower cellulose injection volume was used to evaluate dose-response characteristics of vascular occlusion. The Base population tended to be more susceptible than the Resistant population to this level of particle injection. Interestingly, the incidence of ascites in this chamber (27.3%) did not exceed that seen overall for all Base population males exposed to cool temperatures (29.9%). It remains to be determined if those birds dying within 24 hours post-injection also would have been susceptible to cold-induced ascites. Selecting appropriate cellulose injection protocols clearly will be important for the optimization of this technique.

The combined data for all birds exposed to cool temperatures and injected on Days 47–48 with 0.8 ml of cellulose particles were evaluated, and the results summarized. The large 0.8 mL injection dose was chosen because broilers at 47 Days of age have substantially larger lungs than at 20 Days of age, and thus presumably they have more pulmonary vascular capacity. In addition, these birds already had survived a substantial cold temperature challenge, and consequently they were functionally resistant to pulmonary hypertension. The Base population again was more susceptible to particle injection, as 49.1% did not have sufficient pulmonary vascular capacity to survive for $\leq24$ hours, whereas only 20.5% of the Resistant population fell within this category (P=0.036). There were sufficient birds in this last experiment to compare data for susceptible (died $\leq24$ hours post-injection) and resistant (survived 48 hours post-injection) individuals between the Base and Resistant populations. The sole difference evident in this comparison related to tendencies in the RV:TV ratios. Evidently those broilers capable of surviving the combined long-tern cool temperature challenge followed by an 0.8 mL i.v. particle injection were performing slightly less right ventricular work. This last experimental protocol suggests an interesting opportunity exists for using the i.v. particle injection after normal selection criteria (growth, conformation, fat pad, etc.) have been evaluated.

Conclusions

1. The Base population exhibits a consistent annual trend toward lower ascites susceptibility when exposed to very similar cool temperature challenges in our environmental chambers.

2. Evidently after two generations of selection we approached the effective limit of the pulmonary artery clamp technique for reducing ascites susceptibility. The pulmonary artery clamp technique continues to serve as the "gold standard" for selecting against PHS resistance. We are fully comfortable with the results of clamping one pulmonary artery.

3. The results of the micro-particle injections were close to perfect. We can adjust the severity of the challenge by adjusting the dosage of particles injected. The subsequent $\leq24$ hour mortality apparently is directly proportional to the pulmonary vascular capacity (anatomical or metabolic) we would anticipate in the Base vs. PHS-Resistant populations. As a caveat, these results do not prove that similar subsets of broilers are resistant to unilateral pulmonary artery occlusion and micro-particle injections.

4. The incidence of ascites following i.v. particle injections may depend on the magnitude of the $\leq24$ hour post-injection mortality (presumably the most susceptible individuals are eliminated immediately), as well as the environmental and management conditions under which the birds are maintained subsequent to particle injection. Due to possible variability in environment and management conditions, the $\leq24$ hour post-injection mortality should be targeted as the key index of pulmonary vascular capacity.

5. The results of micro-particle injections on Days 47–48 indicate injections can be used effectively after normal selection criteria (growth, conformation, fat pad, etc.) have been evaluated. This would require increasing the number of birds reared to the age of selection, but the approach would prevent the inadvertent concentration of slower-growing individuals that may occur with Day 14–20 injections.

6. Assuming the slow growth/restriction feeding conditions under which mature breeding stocks are maintained does not preclude the efficacy of selection for improved pulmonary vascular capacity using i.v. particles, then end-of-cycle pedigree stocks could be evaluated with high-dose i.v. particle injection prior to depopulation. Reserved eggs of $\leq24$ hour survivors then would serve as the immediately nucleus of a resistant line. To provide a genetic assessment of this strategy, we could use the cool temperature model to compare the ascites incidence among the progeny of <24 hour post-injection mortality vs. $\leq24$ hour survivors.

Example 4

Responses of Male Broilers to Intravenous Injections with Polystyrene and Cellulose Particles If the micro-particle injection technique is to be optimized, it is important to evaluate the biological responses of broilers to intravenously injected microparticles of different sizes and compositions. Accordingly, 22- to 24-day old male broilers were injected with microparticles composed of polystyrene ($15\mu$ diameter) or cellulose (about 50 to about $80\mu$ diameter). The birds then were reared to 49 Days of age under fast-growth+thermoneutral conditions, and the incidences of acute post-injection mortality and ascites were recorded.

Materials and Methods

Male broiler chicks were obtained from the Hubbard ISA Hatchery at Hot Springs, AR on Jan. 19, 2000. The chicks were wing-banded and placed on fresh wood shavings litter in 2 environmental chambers (8 m$^2$ floor space) in the Poultry Environmental Research Lab. They were brooded at 33 Con Days 1–5,29 Con Days 6–10, 27 C on Days 11–17, and thereafter at21 C (thermoneutral temperature) until the experiment was terminated. The photoperiod was 24 h of light on Days 1–5, and 23 h light/1 h dark thereafter. Feed and water were provided for ad libitum consumption. Water was provided in Plasson waterers due to prior experience that nipple waterers markedly reduce the incidence of PHS (Wideman et al., 1998). A corn-soybean meal-based broiler ration formulated to meet or exceed the minimum NRC (1984) standards for all ingredients, including 22.7% CP, 3,059 kcal ME/kg, 1.5% arginine, and 1.43% lysine, was provided as crumbles during Weeks 1 and 2, then the same ration was provided as pellets thereafter.

Particle Injections. Micro-granular CM-32 ion exchange cellulose was mixed at 0.02 g/mL in heparinized saline (200 unites ammonium heparin/mL of 0.9% NaCl). The mixture was vortexed continuously on a magnetic stirring plate to keep the particles suspended. Within 1 hour after mixing, the cellulose was injected into a wing vein using a 1 mL tuberculin syringe and a 22 gauge needle. On Days 22 to 23, 58 randomly selected birds were injected with 0.4 to 0.5 mL of the cellulose suspension, regardless of body weight The polystyrene micro-spheres were mixed with in heparinized saline at 0.04 g/mL, and were vortexed continuously as described above. On Days 23 to 24, 81 randomly selected birds were injected i.v. with 1.0 mL of the polystyrene micro-sphere mixture, regardless of body weight. The remaining 26 birds remained as uninjected controls.

Necropsies were conducted on all mortality after day 30, as well as on all birds surviving to the end of the experiment Birds were euthanized with $CO_2$ gas, and the heart was removed, dissected and weighed for calculation of the right:total ventricular weight (RV:TV) ratio as an index of pulmonary hypertension (Burton et al., 1968; Cueva et al., 1974; Sillau et al., 1980; Huchzermeyer et al., 1988; Peacock et al., 1989). A diagnosis of ascites was recorded only when ascitic fluid accumulation was evident or when a plasma clot adhered to the surface of the liver.

Results and Discussion and Example 4

Figure 15:
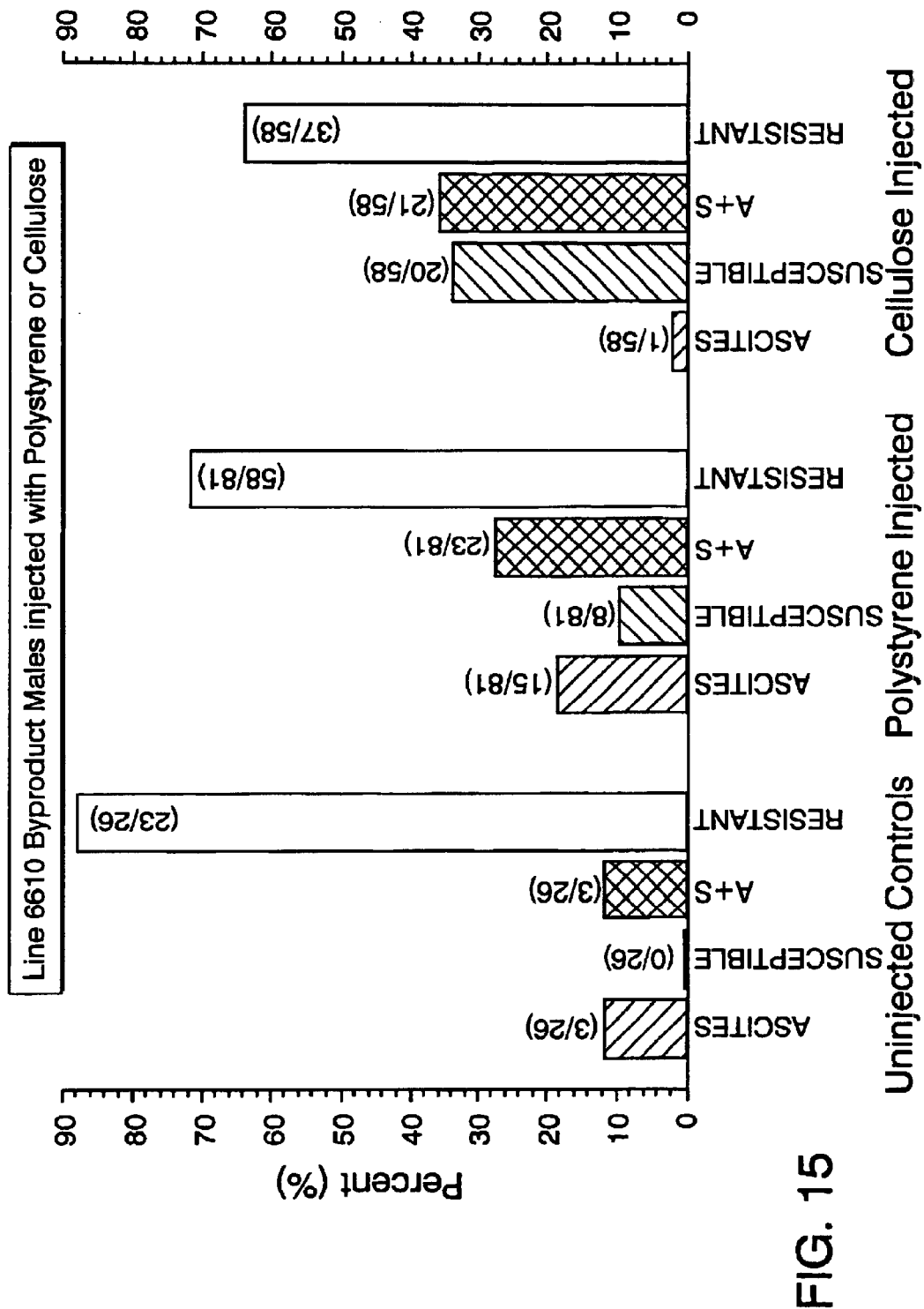
FIG. 15 is a graph showing percentages of birds (byproduct males) falling within four categories. Ascites; Susceptible; Acites+Susceptible; and Resistant, for each of the three treatment groups, Uninjected Controls; Polystyrene Injected; and Cellulose Injected.

Data for the experiment are seen in FIG. 15 showing the percentages of birds falling within four categories (Ascites; Susceptible; Ascites+Susceptible; Resistant) for each of the three treatment groups (Uninjected Controls; Polystyrene Injected; Cellulose Injected). The "Susceptible" category identifies the birds that died within 24 hours after particle injections, whereas the "Resistant" category includes all birds that neither died within 24 hours post-injection nor subsequently developed ascites. In the uninjected control group, 12% developed ascites by Day 49, none died during the Day 22 to 25 time period, and 88% remained resistant/ nonascitic. The polystyrene injections caused 10% mortality within 24 hours and a 19% ascites incidence by Day 49, yielding a total A+S incidence of 28%. Birds receiving the cellulose injections exhibited 34% mortality within 24 hours and a 2% ascites incidence by Day 49, yielding a total A+S incidence of 36%. When compared with the relatively mild acute responses to the polystyrene injections, apparently the stronger challenge exerted by the cellulose injections immediately eliminated most of the ascites-susceptible individuals in the cellulose group. The A+S incidence did not differ between the uninjected control and polystyrene groups (P=0.214; Z-Test), and differed marginally between the uninjected control and cellulose groups (P=0.0817; Z-Test).

Conclusions

1. Particles of different sizes lodge at different levels of the pulmonary micro-vasculature. The larger cellulose particles block inter- and intra-parabronchial arteries and arterioles, therefore each cellulose particle can effectively block blood flow through a multitude of post-arteriole capillaries. The smaller polystyrene micro-spheres are sized to block individual blood capillaries. Therefore, many-fold more of the smaller polystyrene particles are needed to achieve the same magnitude of pulmonary vascular occlusion caused by an individual cellulose particle.

2. Cellulose persists in the pulmonary vasculature for only 10 to 14 days prior to being removed by the immune system. Polystyrene would be expected to remain permanently lodged in the pulmonary vasculature (Wideman, previous observations).

3. In the present study, polystyrene injections triggered less of an acute challenge (less mortality during the 24 hour post-injection period) but more of a long-term induction of ascites when compared with cellulose.

4. When n compared with the uninjected control group, the A+S mortality was numerically 2-fold higher for the polystyrene-injected group and 3-fold higher for the cellulose injected group. The incidence of ascites following i.v. particle injections appears to depend on the magnitude of the 24 hour post-injection mortality (presumably the most susceptible individuals are eliminated immediately) as well as the anticipated long-term persistence of the vascular occlusion (longer for the polystyrene than for cellulose).

Conclusions

Micro-particulates introduced into a suitable systemic vein are carried by the blood to the lungs, where they are trapped by, and partially obstruct, the pulmonary microvasculature (Boelkins et al., 1973; Wolfenson el al., 1978; Scheid and Holle, 1978; Wolfenson, 1983; Brackenbury et al., 1990). The organic and inorganic micro-particulates evaluated in the present study triggered physiological responses typical of those observed after unilateral pulmonary artery occlusion, including pulmonary hypertension, hypoxemia, and systemic hypotension (Wideman and Kirby, 1995a,b; Wideman et al., 1996a,b, 1997, 1998b, 1999b; Forman and Wideman, 1999a,b). Specifically, pulmonary vascular resistance increased in proportion to the cumulative numbers of cellulose particles injected. Each of the micro-particulates injected in this study forced the right ventricle to rapidly develop an elevated pulmonary arterial pressure to propel the cardiac output through the lungs. Forcing tie cardiac output through fewer vascular channels caused concomitantly higher transit speeds for the red blood cells, which apparently did not reside at the pulmonary gas exchange surfaces long enough to permit the hemoglobin to be fully saturated with oxygen. A diffusion limitation was exposed, resulting in undersaturation of the systemic arterial blood with oxygen (hypoxemia) characteristic of broilers that are susceptible to ascites (Henry and Fedde, 1970; Peacock et al., 1989, 1990; Reeves et al., 1991; West, 1993; Wideman and Kirby, 1995a,b; Wideman et al., 1996a,b; Fedde et al., 1998; Wideman and Tackett, 1999a,b). Hypoxemic vasodilation of the systemic resistance vessels serves to increase blood flow and thus oxygen delivery to the tissues. In the present study, reductions in total peripheral resistance were associated with reductions in the mean systemic arterial pressure in proportion to the cumulative numbers of particles injected. Systemic hypotension of a similar origin has been observed in preascitic and ascitic broilers (Peacock et al., 1989; Forman and Wideman, 1999a, Wideman and Tackett, 1999a). Overall, these observations indicate the intravenous micro-particulate injection methodology has potential for replacing unilateral pulmonary artery occlusion as the technique of choice for inducing sustained pulmonary hypertension to routinely eliminate ascites-susceptible individuals from commercial broiler lines. The results shown in FIG. 8 and Table 3 fully support our assumption that physical occlusion of the pulmonary microvasculature, in proportion to the number of particles injected, should provide the means for efficiently creating a controllable, sustained increase in pulmonary vascular resistance leading to pulmonary hypertension syndrome (ascites).

The key issues remaining in the development of this methodology include assessing the relative advantages and disadvantages of various micro-particulates, as well as developing techniques for injecting sufficient numbers of particles to achieve the desired level of sustained pulmonary hypertension. Several characteristics of an ideal micro-particulate would include: (a) a diameter range of $15\mu$ to $80\mu$ suitable for blocking the pulmonary microvasculature without offering substantial resistance to injection through a 23 GA needle; (b) a hydrophilic particle surface permitting easy suspension in aqueous injection media at adequate concentrations for relatively small volume i.v. injections; (c) a specific gravity close to one, similar to saline or plasma, allowing the particles to remain in suspension throughout the process of injection and transport to the lungs in the blood; (d) long-term physical and biochemical stability to prevent the particles from being dislodged from the pulmonary microvasculature by hemodynamics forces (blood pressure, blood flow), and to delay in situ absorption by macrophages or other components of the immune system; and, (e) minimal capacity to trigger blood clot formation, or the capacity to overcome clot formation by co-injection of suitable anticoagulants (heparin, citrate, EDTA, EGTA, etc.). Previously we had demonstrated that microclots can form even in well heparinized broiler blood, and that microclot formation can be prevented by using disodium ethylenediamine tetraacetate (EDTA) as an anticoagulant (Fedde and Wideman, 1996). However, we remain uncertain of the micro-hemodynamic consequences of using anticoagulants that function as calcium chelators (citrate, EDTA, EGTA). It also remains to be determined whether the relative antigenicity of the micro-particulates (degree of immune response triggered) is important for using this methodology to identify the genotypes of birds that are susceptible or resistant to ascites.

1. Occlusive or (partially or completely) obstructive materials introduced into the blood stream for the purpose of causing pulmonary vascular obstruction leading to the onset of pulmonary hypertension (PH) and pulmonary hypertension syndrome (PHS) may vary in size or diameter, depending on the blood vessel destined to be obstructed. For example, the smallest pulmonary blood capillaries are approximately 4 to 8 $\mu$m in diameter, requiring particles of similar or larger size to obstruct at the capillary level. The large pulmonary arteries in older broilers are 5 mm in diameter, requiring a similar or larger size to achieve obstruction.

2. In addition to the materials mentioned previously, obstructive materials could include but are not limited to: macro- or micro-thrombi or thromboemboli (blood clots) or thrombin or clot initiator injections; fat; bone marrow air; glass beads; latex beads or coagulations (e.g., acidified latex); ceramic beads; plastic materials; spores; cells; silastic materials; gelatinous materials; coagulated or congealed protein (e.g. acidified milk protein); clay; ash particles or pumice powder, starch granules; endotoxin; balloons; collagen or fiber suspensions; or any other material capable of directly obstructing or triggering processes that lead to obstruction of the pulmonary vasculature. For example, a blood clot formed outside of the body (preformed autologous blood clot) and then injected intact into a systemic vein, or caused to form within a vein, subsequently would flow to the pulmonary vasculature where obstruction would occur. A blood clot of suitable size could obstruct an entire pulmonary artery (macro-embolism), simulating the surgical pulmonary artery clamp technique Similarly, gelatin cross linking technology (or any similar polymerization or crystallization process) could be used to form a suitable bolus intravascularly or via injection, that then would flow through the veins to the pulmonary vasculature where obstruction would occur (e.g., for intravascular gelatin crosslinking technology and discussion of latex-based vascular casting compounds, see: Wideman, R. F., Braun, E. J., and Anderson, G. L. Microanatomy of the domestic fowl renal cortex. J. Morphology 168: 249–267, 1981).

3. Pulmonary vascular obstruction or occlusion could be accomplished with a single injection, or with a series of two or more injections of the same or of different materials. For example, if it is demonstrated that a particulate material of interest is dissolved or scavenged from the lungs within a period of time that is not long enough to fully elicit the desired result in a sufficient percentage of subject animals, then phased (repeated or supplemental) injections can be administered over a period of time, indeed over the lifespan of the subject animal 4. Injections can occur at ages other than those described in the previously submitted disclosures and documentation. For example, broilers ranging from in ovo to mature adults might be injected, as long as the materials entered or were created or induced within the systemic vasculature and then traveled through the systemic veins to the lungs.

5. The end point identified by the pulmonary vascular occlusion need not be the onset of clinical ascites or death. Indeed, a variety of methods are described in the scientific literature for use as predictive indices that individual birds are susceptible or resistant to the pathogenesis of ascites. For example, following injections, subject birds might be evaluated using these diagnostic indices to identify those individuals exhibiting the most adverse responses (most PHS-susceptible) as well as those exhibiting the least adverse responses (most PHS-resistant). Some of these indices have been validated by Dr. Wideman and colleagues, and were reported in the following literature:

Wideman, R. F., and Kirby, Y. K. Electrocardiographic evaluation of broilers during the onset of pulmonary hypertension initiated by unilateral pulmonary artery occlusion Poultry Science 75:407–416, 1996.

Roush, W. B., Kirby, Y. K, Cravener, T. L., and Wideman, R. F. Artificial Neural Network Prediction of Ascites in Broilers. Poultry Science 75:1479–1487, 1996.

Kirby, Y. K, Kirby, J. D., Mcnew, R. W., and Wideman, R. F. Evaluation of logistic versus linear regression models for predicting pulmonary hypertension syndrome (ascites) using cold stress or pulmonary artery clamp models in broilers. Poultry Science 76:392–399, 1997.

Roush, W. B., T. L. Cravener, Y. Kochera Kirby, and R. F. Wideman. Probabilistic neural network prediction of ascites in broilers based on minimally invasive physiological factors. Poultry Science 76:1513–1516, 1997.

Wideman, R. F., Wing, T., Kirby, Y. K., Forman, M. F., Marson, N., Tackett, C. D., and Ruiz-Feria, C. A. Evaluation of minimally invasive indices for predicting ascites susceptibility in three successive hatches of broilers exposed to cool temperatures. Poultry Science 77:1565–1573, 1998.

Kirby, Y. K., McNew, R. W., Anthony, N. B., Marson, N. E., Hughes, J. D., Kirby, J. D., and Wideman, R. F. Electrocardiographic evaluation of broilers following unilateral occlusion of an extrapulmonary primary bronchus. Poultry Science 78:242–254, 1999.

Wideman, R. F., Maynard, P., and Bottje, W. G. Venous blood pressure in broilers during acute inhalation of five percent carbon dioxide or unilateral pulmonary artery occlusion. Poultry Science 78:1443–1451, 1999.

Ruiz-Feria, C. A., Beers, K. W., Kidd, M. T., and Wideman, R. V. Plasma taurine levels in broilers with pulmonary hypertension syndrome induced by unilateral pulmonary artery occlusion. Poultry Science 78:1627–1633, 1999.

Forman, M. F., and Wideman, R. F. Renal responses of normal and preascitic broilers to systemic hypotension induced by unilateral pulmonary artery occlusion. Poultry Science 78:1773–1785, 1999.

Wideman, R. F., Fedde, M. R., Tackett, C. D., and Weigle, G. E. Cardio-pulmonary function in preascitic (hypoxemic) or normal broilers inhaling ambient air or 100% oxygen. Poultry Science 79: (in press), 2000.

Roush, W. B., and Wideman, R. F. Evaluation of growth velocity and acceleration in relation to pulmonary hypertension syndrome (PHS). Poultry Science 79: (in press), 2000.

Any factor that increases the cardiac output, reduces the pulmonary vascular capacity, or increases the pulmonary vascular resistance theoretically can initiate or accelerate the pathophysiological progression leading to pulmonary hypertension syndrome (PHS) in broilers. An under-appreciated but important function of the pulmonary vasculature is to filter and clear the returning venous blood of particulate matter, such as aged red blood cells, micro- and macro-thromboemboli (blood clots), bacteria, immune complexes, and cellular debris. This blood clearing function of the lungs serves to defend sensitive tissues such as the brain and heart; however, the process can be profoundly deleterious to pulmonary hemodynamics and gas exchange. We hypothesize that the normal pulmonary function of entrapping particulates such as bacteria can initiate or contribute to the pathogenesis of PHS through three interactive mechanisms. First, bacterial endotoxins are known to stimulate endothelin-mediated thromboxane-dependent increases in pulmonary vascular resistance leading to pulmonary hypertension in mammals. Pilot studies have confirmed that intravenous endotoxin (lipopolysaccharide, LPS) injections initiate a biochemical cascade culminating in pulmonary vasoconstriction and pulmonary hypertension in broilers. Second, physical occlusion of vascular channels serves to directly increase the resistance to blood flow by reducing the overall cross-sectional area of the pulmonary vasculature. By forcing the cardiac output to flow through fewer vascular channels at a higher pressure and flow rate, physical occlusion promotes pulmonary edema and also exposes an incipient diffusion limitation that triggers the onset of systemic hypoxemia (under-saturation of arterial blood with oxygen). Third, the response of the immune system to entrapped particulates amplifies the pulmonary hypertensive and hypoxemic responses, due to the local release of vasoactive substances (arachidonic acid derivatives, leukotrienes, serotonin), as well as substances that damage the endothelin and surrounding tissues (histamine, oxygen radicals). Pilot studies have confirmed that intravenously injected particulates are trapped in the pulmonary vasculature, triggering rapid (within 20 minutes) and sustained focal inflammatory responses, pulmonary hypertension, hypoxemia, and an elevated incidence of PHS when compared with saline-injected control broilers. These and previous studies reveal widely varied individual responses within groups of broilers obtained from the same hatch and reared under putatively identical conditions. Research has been proposed to more fully characterize the pulmonary responses to intravenously administered endotoxin and particulates. Key immunological and physiological indices that are correlated with individual variability in the pulmonary hypertensive response must be identified. One long-term objective is to identify desirable response patterns or traits that can be used by geneticists to select for improved pulmonary health, field livability and PHS resistance in commercial broilers.

Overview

Worldwide, approximately 2% of all broilers die from pulmonary hypertension syndrome (PHS, ascites). This level of mortality has been estimated to cost the international broiler industry $1,000,000,000 annually (Maxwell and Robertson, 1997, 1998). Susceptible broilers initially develop an elevated blood pressure within the pulmonary circulation (pulmonary hypertension), accompanied by characteristic work hypertrophy of the right ventricle and an elevation of the right- to-total ventricular weight ratio (RV:TV ratio). A distinctive pathophysiological progression then ensues, including the sequential development of hypoxemia (poorly oxygenated arterial blood), systemic arterial hypotension, right-sided congestive heart failure, central venous congestion, cirrhosis of the liver, and transudation of ascitic fluid into the abdominal cavity. Based on this characteristic progression, the terms pulmonary hypertension syndrome (PHS) and ascites syndrome are widely accepted as synonyms (Huchzermeyer and DeRuyck, 1986; Julian, 1988, 1993; Odom, 1993; Wideman and Bottje, 1993; Wideman, 1999b).

Ongoing efforts to understand the pathogenesis of ascites in commercial broilers are focused on the multiple factors capable of initiating or contributing to the development of pulmonary hypertension, as summarized by the equation: pulmonary arterial pressure=cardiac output×pulmonary vascular resistance. This equation indicates that the right ventricle of the heart must perform additional work to increase the pulmonary arterial pressure whenever the requisite cardiac output (volume of blood pumped/minute by one ventricle) cannot be accommodated by the pulmonary vascular capacity. The pulmonary vascular capacity is defined broadly to encompass anatomical constraints related to the compliance and volume of the blood vessels, as well as metabolic limitations related to the tone (state of contracture) maintained by the resistance vessels. Substantial anatomical and physiological evidence indicates the pulmonary vasculature of broilers has an exceptionally low compliance (is functionally inelastic) and is fully engorged with blood at a normal (resting) cardiac output Consequently, broiler lungs do not adapt to an increasing cardiac output through compensatory mechanisms known to lower the pulmonary vascular resistance in mammals, such as flow-dependent pulmonary vasodilation and the recruitment of previously un- or under-perfused vascular channels. Instead, proportional increases in pulmonary arterial pressure are required to propel increments in cardiac output through broiler lungs having an inadequate vascular capacity. The resulting acceleration of blood flow can prevent the erythrocytes from residing at the gas exchange surfaces long enough to fully equilibrate with oxygen, leading to hypoxemia attributable to a diffusion limitation (Wideman and Bottje, 1993; Wideman and Kirby, 1995a,b; Wideman, 1999a,b; Wideman et al., 1996a,b, 1997,1998b, 1999b; Wideman and Tackett, 1999a,b). Genetic selection experiments have confirmed that resistance to pulmonary hypertension syndrome depends substantially on the capacity of the pulmonary vasculature to accommodate increases in cardiac output. Broiler breeder parents capable of thriving after their pulmonary vascular resistance was doubled by surgically occluding one pulmonary artery, subsequently produced progeny exhibiting a 75% reduction in ascites susceptibility within two generations of selection (PHS-resistant Line, Wideman and French, 1999a,b). The pulmonary vascular limitations observed in broilers apparently are related to the constant-volume (non-inflating) design of avian lungs, which are partially embedded between five ribs adjacent to the vertebral column. Lung volume is limited by frame (skeletal) size, which has remained relatively constant during ongoing genetic selection for ever-increasing rates of muscle accretion and thus metabolic oxygen demand. Overall, any factor that increases the cardiac output (fast growth, cool temperatures, hypoxemia), reduces the pulmonary vascular capacity (respiratory disease, vascular obstruction), or increases the pulmonary vascular resistance (hypoxia, acidosis, endogenous vasoconstrictors) theoretically can initiate or accelerate the pathophysiological progression leading to pulmonary hypertension syndrome (Wideman and Bottje, 1993, Wideman, 1997, 1999b).

Figure 12B:
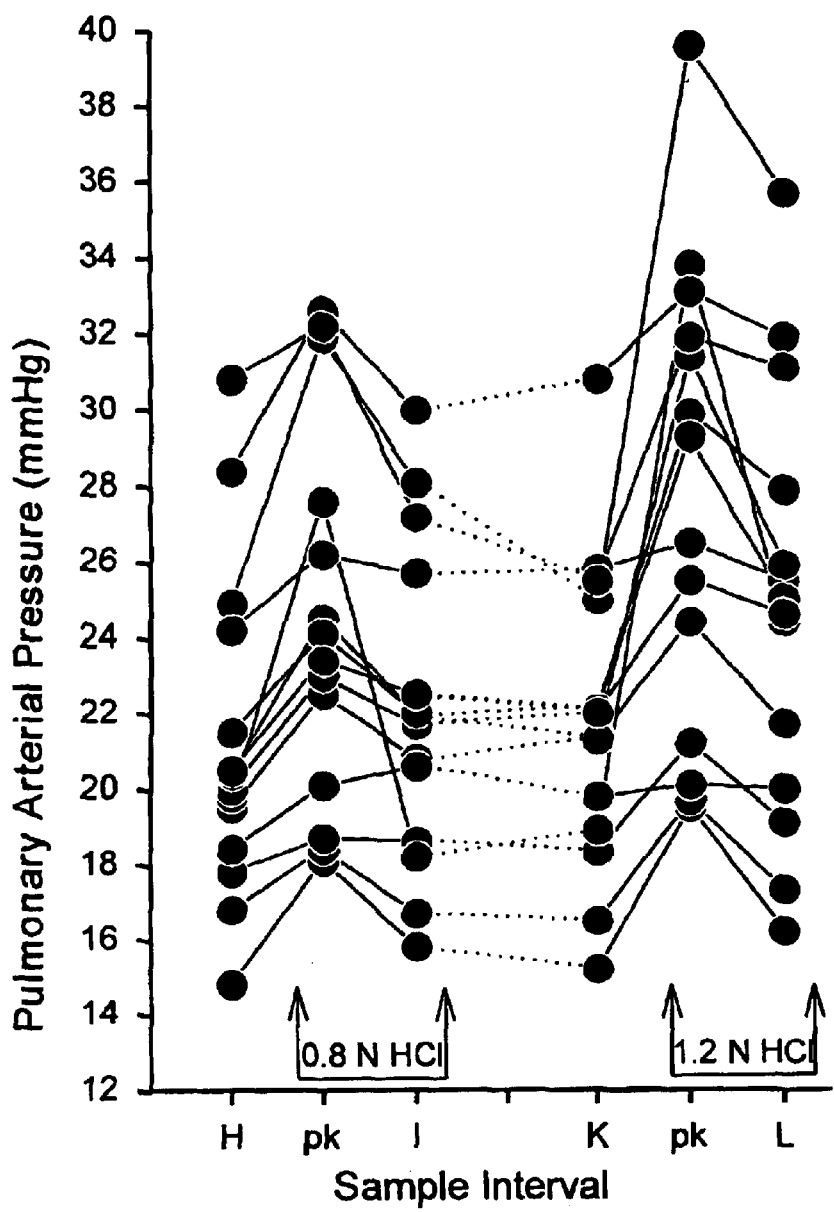
FIG. 12B is a graph showing pulmonary arterial pressures of the individual birds before, during, and after the peak response to the respective injections. Lines connecting individual bird values illustrate variability (from Wideman et al., 1998a. *Poultry Sci.*, 77:309–321).

Thromboxane, a potent vasoconstrictor derived from circulating thrombocytes or lung and vascular tissues, directly increases the pulmonary vascular resistance and the pulmonary arterial pressure in broilers (FIG. 1A, Wideman et al., 1999a). Thromboxane also appears to mediate the pulmonary vasoconstriction triggered by acute acidosis (FIG. 12A, Wideman et al., 1998a). The magnitude of the pulmonary hypertensive response to thromboxane and acute acidosis varies widely among individual broilers, suggesting crucial traits related to PHS susceptibility potentially may be revealed by elucidating the mechanisms involved (FIGS. 11B and 12B). The pulmonary hypertension triggered by thromboxane has a functional significance related to the presumed contribution of poor air quality and respiratory disease to the ascites syndrome. Accordingly, it has been proposed that inhaled dust and pathogens may cause focal damage and pulmonary vasoconstriction by increasing the intrapulmonary production of reactive oxygen species and thromboxane, coupled with reduced synthesis the vasodilator prostacyclin (Bottje and Wideman, 1995; Wideman et al., 1999a). Indeed, various particulates and bacterial endotoxins stimulate endothelin-mediated thromboxane-dependent increases in pulmonary vascular resistance and pulmonary arterial pressure in mammals (Morel et al., 1989; Longworth et al., 1994; Staub, 1994; Faltin et al., 1996). Similar mechanisms may be involved in the pathogenesis of ascites triggered in broilers by intratracheal inoculation with infectious bronchitis virus and E. coli (Tottori et al., 1997b), or by pulmonary aspergillosis (Julian and Goryo, 1990). During endotoxin infusion in mammals, both the vasoconstrictor thromboxane and the vasodilator prostacyclin normally are produced, and can exert dynamically antagonistic influences on pulmonary vascular resistance depending on the experimental protocol (Longworth et al., 1994; Frank et al., 1996). Enhanced prostacyclin synthesis attenuates the pulmonary vasoconstriction induced by hypoxia or metabolic acidosis in mammals (Farrukh et al., 1989; Yamagichi et al., 1989; Frank et al., 1996). The variable efficacy of aspirin on the incidence of ascites in broilers may reflect aspirin's non-specific nullification of both the protective role of prostacyclin as well as the detrimental impact of thromboxane on pulmonary vascular resistance (Shlosberg et al., 1996; Balog et al., 1997; Wideman et al., 1999a).

An under-appreciated but nevertheless important function of the pulmonary vasculature is to filter and clear the returning venous blood of particulate matter, such as aged red blood cells, micro- and macro-thromboemboli, bacteria, immune complexes, and cellular debris (Dantzker, 1997; Brain et al., 1999). Given a cardiac output averaging $\geq 150$ mL/min per kg body weight for broilers (Wideman, 1999a), and a total blood volume averaging $\geq 8\%$ of body weight in young birds (Sturkie, 1986a), it is evident that the lungs can routinely clear the entire blood volume in less than a minute. In addition to particulates entering the blood stream directly, materials drained from the interstitial spaces throughout the body via the lymphatic capillaries, subsequently would flow through major lymph trunks into the vena cavae immediately proximal to the right atrium (Berens and Rautenfeld, 1993). The mural lymph nodes of domestic fowl are not anatomically designed to filter lymph through narrow sinusoidal spaces, consequently the pulmonary vasculature may be challenged by a wide variety of particulates. The blood clearing function of the pulmonary vasculature serves to defend sensitive tissues such as the brain and heart; however, the process of physically trapping and immunologically responding to particulates can be profoundly deleterious to pulmonary hemodynamics and gas exchange. We hypothesize that the normal pulmonary function of entrapping particulates such as bacteria can initiate or contribute to the pathogenesis of PHS through three interactive mechanisms. First, bacterial endotoxins are known to stimulate endothelin-mediated thromboxane-dependent increases in pulmonary vascular resistance leading to pulmonary hypertension in mammals (vide supra). Second, physical occlusion of vascular channels serves to directly increase the resistance to blood flow by reducing the overall cross-sectional area of the pulmonary vasculature. Third, the response of the immune system to entrapped particulates amplifies the pulmonary hypertensive and hypoxemic responses, due to the local release of vasoactive substances, as well as substances that affect the endothelin and surrounding tissues (histamine, oxygen radicals).

Figure 13A:
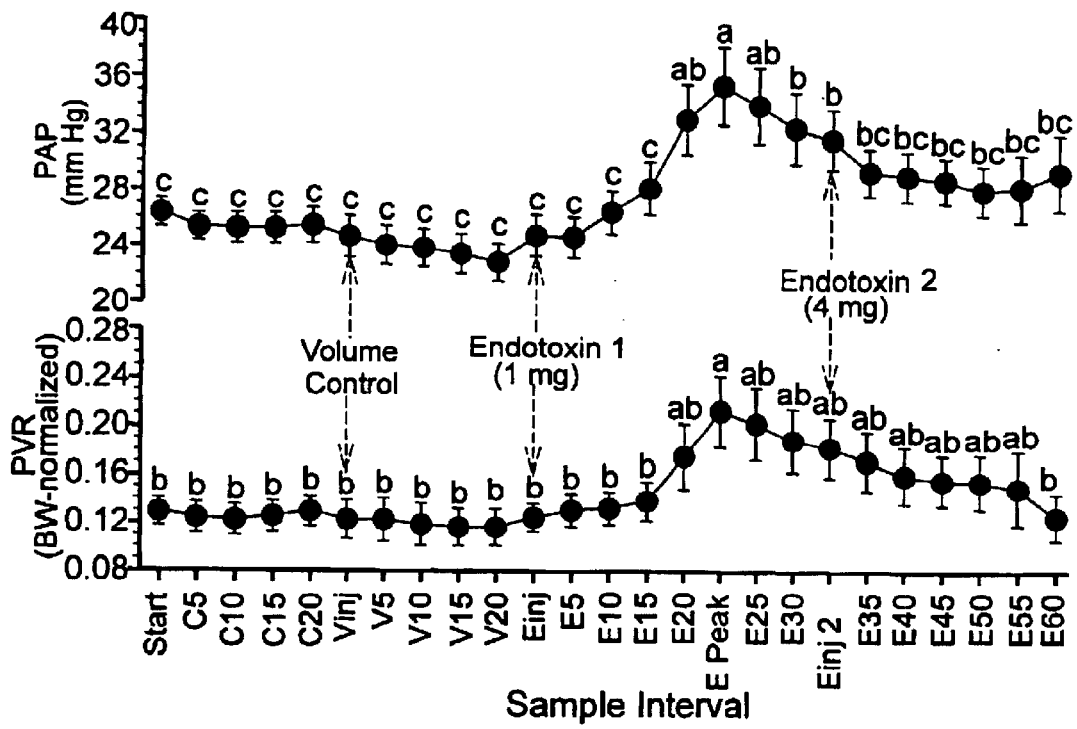
FIG. 13A is a graph showing pulmonary arterial pressure and pulmonary vascular resistance (standard units normalized per kg BW) in 7 male broilers at the start of data collection (Start), at 5 minute intervals during the control period (C5 to C20), within 30 seconds after the volume control injection (Vinj), at 5 minute intervals during the volume control period (V5 to V20), within 30 seconds after the 1 mg LPS injection Einj 1), at 5 minute intervals after the 1 mg LPS injection(E5 to E30) and during the maximum pulmonary arterial pressure response to the 1 mg LPS (E Peak). within 30 seconds after the 4 mg LPS injection (Einj 2), and at 5 minute intervals after the 4 mg LPS injection (E35 to E60). Different letters (a, b, c) designate differences between means over time (P 0.05)
Figure 13B:
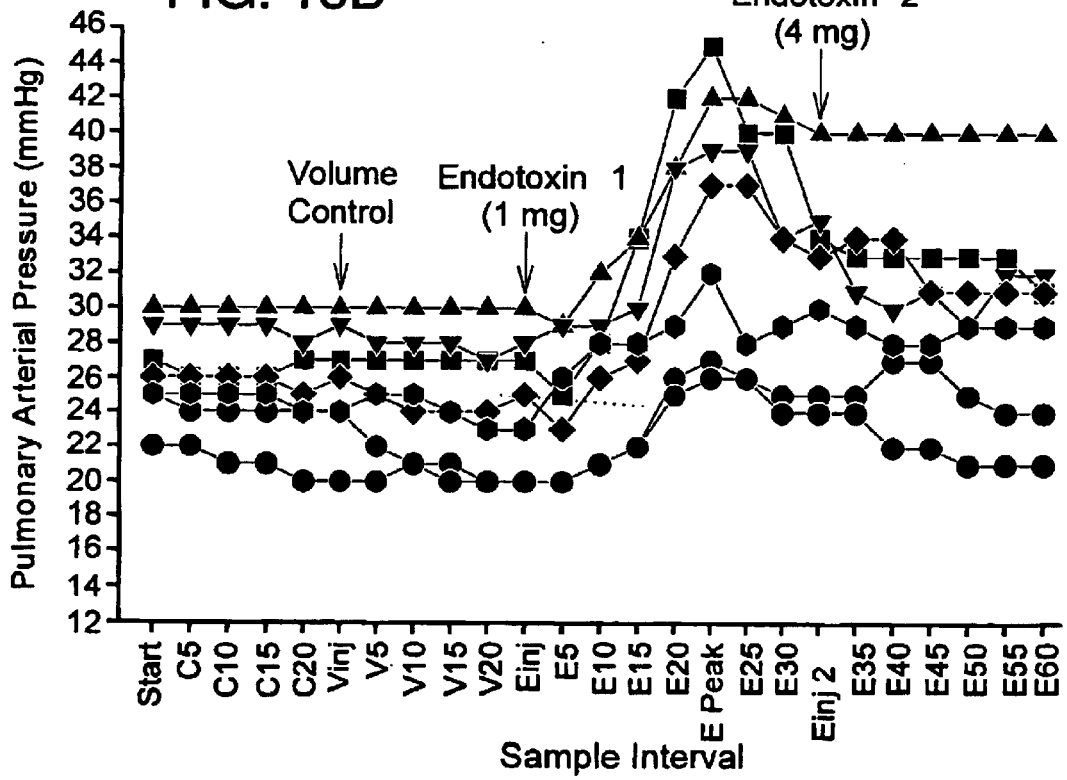
FIG. 13B is a graph showing pulmonary arterial pressures of the individual birds over the course of the experiment. Lines connecting individual bird values illustrate variability (Wideman and Erf, unpublished).

Pilot studies have confirmed that intravenously administered endotoxin (lipopolysaccharide, LPS) can initiate pulmonary vasoconstriction and pulmonary hypertension in broilers (FIG. 13A). Clinically healthy broilers injected i.v. with 1 mg LPS exhibited a delayed onset ($\geq 15$ min) pulmonary vasoconstriction that increased the pulmonary arterial pressure from a baseline value of 24 mm Hg to a peak value of approximately 35 mm Hg within 20 to 25 min, followed by a gradual decline to approximately 29 mm Hg by 60 min post-injection. Supplemental 4 mg injections of LPS failed to initiate a secondary pulmonary hypertensive response. The pulmonary hemodynamic responses to the initial 1 mg LPS injection occurred in spite of a contemporaneous reduction in the mean systemic arterial pressure. These observations are consistent with the hypothesis that the 1 mg LPS injection initiated a biochemical cascade culminating in the delayed onset of pulmonary vasoconstriction. Subsequent to the peak pulmonary hypertensive response, depletion of key components of the cascade, or a dominant role of vasodilatory components, prevented 4-fold higher doses of LPS from reversing the return toward a normal pulmonary vascular tone and pressure (FIG. 13A). The time-course and magnitude of the pulmonary hypertensive responses of individual broilers to endotoxin varied widely, for reasons that are not apparent based on attempts to maintain uniformity across all aspects of the experiment (FIG. 13B). We hypothesize that the observed variability may reflect individual genetic differences related to key components of the vasoactive cascade, or that the prior immune history of individual birds, including the prevalence of pulmonary inflammatory foci, may modify the responsiveness to endotoxin.

Pilot studies also confirm that intravenously injected particles of suitable size and composition are trapped by the pulmonary vasculature, triggering rapid (within 20 minutes) and sustained focal inflammatory responses, pulmonary hypertension, and hypoxemia. Pre-injection vs. 30-minute post-injection differences ($P \leq 0.05$ for each) were, respectively, $21 \pm 1.5$ vs. $30 + 1.0$ mm Hg for pulmonary arterial pressure, $0.06 \pm 0.01$ vs. $0.09 \pm 0.01$ relative resistance units for pulmonary vascular resistance, and $95 \times 1$ vs. $93 \pm 1\%$ for the saturation of arterial hemoglobin with oxygen (Wideman and Erf, unpublished). By forcing the cardiac output to flow through fewer vascular channels at a higher pressure and flow rate, physical occlusion promotes pulmonary edema and also exposes an incipient diffusion limitation that triggers the onset of systemic hypoxemia. Injecting the same particulates i.v. at 17 to 21 days of age also triggered a 22.5% incidence of PHS, which more than doubled the 6.7% PHS incidence occurring in saline-injected control broilers by the termination of the experiment at 43 days of age (Wideman and Erf, unpublished).

Intrapulmonary cell-mediated processes also rapidly clear particulates from avian lungs (Brown et al., 1997; Fedde, 1998).

Experimental Design

Bird Source and Rearing. Broiler chicks derived from bio-secure pedigree lines maintained by a commercial broiler genetics company (Hubbard ISA, see Appendix A) will be used. The same source of chicks previously served as the Base population from which a PHS-resistant line was selected (Wideman and French, 1999a,b). Male chicks from the Base population will be used for the initial series of experiments designed to characterize the key immunological and physiological indices correlated with individual variability in the pulmonary hypertensive response to particulates and endotoxin. Once the time course for key indices has been established, an additional experimental series will be conducted to compare the responses of male chicks from the Base and PHS-resistant lines. All chicks will be brooded and reared in stinless steel cages within the University of Arkansas Poultry Health Laboratory to maintain an essentially dust free environment with minimal exposure to pathogens. These precautions to optimize the pulmonary health and minimize the prior pathogen exposure of the broilers may reduce the individual variation in endotoxin responsiveness.

Indices Correlated with Pulmonary Hypertension. Three independent experiments still be conducted using cage mate broilers that have been injected intravenously either with carrier vehicle alone (unprimed; U) or with the carrier vehicle containing particles sufficient to elevate the overall incidence of PHS (primed; P). The priming injections therefore will create a subpopulation knows to be generating an active pulmonary inflammatory response associated with pulmonary hypertension. The control and particle injections will occur 2 hours (Experiment 1; acute response), 2 days (Experiment 2; intermediate response), or 10 days (Experiment 3, sustained response) prior to evaluating the response to endotoxin. The endotoxin challenge will be similar to that shown in FIG. 3, except separate groups will be used for the volume control (C) and endotoxin (E) injections, and one endotoxin injection will be administered instead of two. Consequently, four groups of 8 birds will be evaluated in each Experiment: unprimed volume control (UC); unprimed endotoxin-injected (UE); particle-primed volume control (PC); and, particle-primed endotoxin-injected (PE). The inclusion of separate volume control groups (UC, PC) within each experiment will appropriately account for any time- or sampling-related changes in measured indices that are not specific to the endotoxin response.

The techniques for recording pulmonary arterial pressure, cardiac output, and systemic arterial pressure have been described previously (Wideman and Kirby, 1995b; Wideman et al., 1996, 1998a, 1999; Wideman, 1999). Briefly, 30 to 42 day old broilers will have ad libitum access to feed and water until they are anesthetized to a surgical plane with allobarbital (5,5-diallyl-barbituric acid; 25 mg kg/BW). They will be fastened in dorsal recumbency on a surgical board thermostatically regulated to maintain a surface temperature of 30 C. An ultrasonic flowprobe connected to a Transonic T206 blood flow meter will be positioned on the right pulmonary artery. The left to pulmonary artery will be cannulated with Silastic® tubing, and the distal end of the cannula will be attached to a blood pressure transducer to record pulmonary arterial pressure. The left cutaneous ulnar vein (wing vein) and brachial artery will be cannulated with PE-50 polyethylene tubing for i.v. injections and infusions (venous cannula), and for blood sample withdrawal and continuous monitoring of systemic arterial pressure (arterial cannula). For data collection, the blood flow meter and blood pressure transducers will be interfaced to a computer through a digital physiograph (Biopac MP 100 data acquisition system using AcqKnowledge software). The primary channels recorded will include blood flow through the right pulmonary artery (BF, mL/min), pulmonary arterial pressure (PAP, mm Hg), and mean systemic arterial pressure (MAP, mm Hg). Average values for these parameters will be measured electronically during representative intervals using previously validated techniques for data averaging (Wideman et al., 1996a,b) and normalization for differences in body weight (Wideman, 1999a). Heart rate (HR beats/min) will be obtained by detecting systolic peaks over time in the pulmonary arterial pressure recording. The primary values will be used to calculate cardiac output (CO=2×BF), stroke volume (SV=CO/HR), pulmonary vascular resistance (PVR=PAP/CO), and total peripheral resistance (TPR=MAP/CO) (Wideman et al., 1996, 1998a, 1999; Wideman, 1999).

After surgical preparations are complete and a 20 min stabilization period has elapsed, control data will be recorded for 20 min., and a 1.5 mL arterial blood sample will be withdrawn halfway through the control period. Broilers then will be injected through the wing vein cannula with 0.2 mL of phosphate buffered saline (PBS) (UC and PC groups), or with a similar volume of PBS containing 1 mg of bacterial endotoxin (lipopolysaccharide, LPS) (UE and PE groups). Data will be recorded for an additional 90 min., and arterial blood samples will be withdrawn at 20 min (peak of the pulmonary hypertensive response, (FIGS. 13A and 13B), and 90 min. (pulmonary hypertension subsides) after the endotoxin injection. Then birds will be humanely euthanized, the lungs will be prepared for histological evaluation, and the heart will be dissected and weighed to determining the RV:TV ratio as an index of pulmonary hypertension (Burton et al., 1968; Cueva et al., 1974; Huchzermeyer et al., 1988).

To assess the influence of general anesthesia and surgical preparation on the pulmonary hypertensive responses to endotoxin, experiment one will include two parallel UE and PE groups in which pulmonary arterial pressures are measured using acutely cannulated unanesthetized broilers. Broilers will be lightly restrained in lateral recumbency, and a 2% lidocaine solution will be infiltrated intracutaneously as a local anesthetic along the left cutaneous ulnar vein, which then will be cannulated with Silastic® tubing. The cannula will be advanced into the pulmonary artery as judged by pressure tracings (Owen et al., 1995c). Arterial and venous cannulae also will be inserted into the brachial artery and wing vein under local anesthesia The birds then will be supported in an upright posture while the pulmonary arterial pressure, systemic arterial pressure and heart rate are recorded. In the absence of a flow probe, cardiac output, pulmonary vascular resistance, and total peripheral resistance cannot be determined on a continuous basis. However, acute changes in pulmonary arterial pressure qualitatively mirror changes in pulmonary vascular resistance (FIGS. 11A–13B, Wideman, 1999a), and virtually identical pulmonary arterial pressure responses to inhalation of 100% oxygen (Wideman et al., 1999c) or 12% oxygen (Ruiz-Feria and Wideman, personal observations) recently were observed when unanesthetized broilers were compared with anesthetized, fully instrumented broilers. We anticipate the pulmonary hypertension induced by endotoxin in unanesthetized broilers will exhibit a range of individual variability similar to the responses of anesthetized and fully instrumented broilers (FIGS. 13A and 13B). If significant qualitative differences are detected, then the unanesthetized preparation can be used for subsequent experiments, and we will forgo direct assessments of cardiac output and vascular resistances. It is the amplitude of pulmonary hypertension, per se, that is most directly predictive of the pathogenesis leading to PHS (Wideman, 1999b).

Data evaluation: 1. Within each experiment, the control/baseline values for the 4 groups can be compared [pool UC&UE control values to compare with pooled PC&PE values] to evaluate changes caused by particle injections; 2. Compare endotoxin PAP peak amplitude/time to peak/time to 50% return to baseline after peak as measures of individual variability ad any changes caused by particle priming; 3. Use correlation analysis to see which changes in blood sample indices (Thromboxane/prostacyclin/biogenic armines/etc.) are best correlated with amplitude & duration of PAP peak.]

Introduction

Pulmonary Hypertension Syndrome (PHS) and Ascites. Worldwide, approximately 2% of all broilers die from pulmonary hypertension syndrome (PHS, ascites). This level of mortality has been estimated to cost the international broiler industry $1,000,000,000 annually (Maxwell and Robertson, 1997, 1998). Susceptible broilers initially develop an elevated blood pressure within the pulmonary circulation (pulmonary hypertension), accompanied by characteristic work hypertrophy of the right ventricle. A distinctive pathogenesis then ensues, including the onset of hypoxemia (poorly oxygenated arterial blood), systemic arterial hypotension, right-sided congestive heart failure, central venous congestion, hepatic cirrhosis, and transudation of ascitic fluid into the abdominal cavity. Based on this pathogenesis, the terms pulmonary hypertension syndrome (PHS) and ascites syndrome are widely accepted as synonyms (Huchzermeyer and DeRuyck, 1986; Julian, 1988, 1993; Peacock et al., 1989, 1990; Odom, 1993; Wideman and Bottje, 1993; Wideman, 2000).

Physiology of PHS. Ongoing efforts to understand the pathogenesis of PHS have focused on the multiple factors capable of initiating or contributing to the development of pulmonary hypertension, as summarized by the equation: pulmonary arterial pressure=cardiac output×pulmonary vascular resistance. This equation indicates that the right ventricle of the heart must perform additional work to increase the pulmonary arterial pressure whenever the requisite cardiac output cannot be accommodated by the pulmonary vascular capacity. The pulmonary vascular capacity is defined broadly to encompass anatomical constraints related to the compliance and volume of the blood vessels, as well as metabolic limitations related to the tone (state of contracture) maintained by the resistance vessels. Substantial anatomical and physiological evidence indicates the pulmonary vasculature of broilers is functionally inelastic (marginally compliant) and is fully engorged with blood at a normal (resting) cardiac output. Consequently, broiler lungs do not adapt to an increasing cardiac output through compensatory mechanisms known to lower the pulmonary vascular resistance in mammals, such as flow-dependent pulmonary vasodilation and the recruitment of previously un-perfused vascular channels. Instead, proportional increases in pulmonary arterial pressure are required to propel an increasing cardiac output through broiler lungs having an inadequate vascular capacity. The resulting acceleration of blood flow prevents the erythrocytes from residing at the gas exchange surfaces long enough to filly equilibrate with oxygen, leading to hypoxemia attributable to a diffusion limitation (Wideman and Bottje, 1993; Wideman and Kirby, 1995a,b; Wideman, 1999, 2000; Wideman et al., 1996a,b, 1997, 1998b, 1999b; Wideman and Tackett, 1999, 2000).

Genetic Component of PHS. The pulmonary vascular limitations observed in broilers apparently are related to the constant-volume (non-inflating) design of avian lungs, which are partially embedded between five ribs. Lung volume is limited by frame (skeletal) size, which has remained relatively constant during ongoing genetic selection for ever-increasing rates of muscle accretion and thus metabolic oxygen demand. Overall, any factor that increases the cardiac output (fast growth, cool temperatures, hypoxemia), reduces the pulmonary vascular capacity (respiratory disease, vascular obstruction), or increases the pulmonary vascular resistance (hypoxia, acidosis, endogenous vasoconstrictors) theoretically can initiate or accelerate the pathophysiological progression leading to pulmonary hypertension syndrome (Wideman and Bottje, 1993, Wideman, 1997, 2000). Genetic selection experiments have confirmed that the susceptibility to PHS depends substantially on the inability of the pulmonary vasculature to accommodate the requisite cardiac output Broiler breeder parents capable of thriving after their pulmonary vascular resistance was doubled by surgically occluding one pulmonary artery, subsequently produced progeny exhibiting a 75% reduction in ascites susceptibility within two generations of selection. The genes involved in ascites susceptibility appear to be dominant, indicating ongoing proactive selection based on key diagnostic indices will be required to improve commercial broiler stock (Wideman and French, 1999, 2000).

Thromboxane and PHS. Thromboxane, a potent vasoconstrictor derived from circulating thrombocytes or lung and vascular tissues, directly increases the pulmonary vascular resistance and the pulmonary arterial pressure in broilers (FIG. 11A). Thromboxane also appears to mediate the pulmonary vasoconstriction triggered by acidosis (FIG. 12A). Dietary acidification increases the incidence of PHS in broilers (Owen et al., 1994). The magnitude of the pulmonary hypertensive response to acidosis varies widely among individual broilers. This variability suggests crucial traits related to PHS susceptibility potentially may be revealed by elucidating the mechanisms involved (FIGS. 11B and 12B). The pulmonary hypertension triggered by thromboxane has a functional significance related to the presumed contribution of poor air quality and respiratory disease to the ascites syndrome. Accordingly, it has been proposed that inhaled dust and pathogens may cause focal damage and pulmonary vasoconstriction by increasing the intrapulmonary production of reactive oxygen species and thromboxane, coupled with reduced synthesis of the vasodilator prostacyclin (Bottje and Wideman, 1995; Bottje et al., 1998; Wideman et al., 1999a). Indeed, various particulates and bacterial endotoxins stimulate endothelin-mediated thromboxane-dependent increases in pulmonary vascular resistance and pulmonary arterial pressure in mammals (Morel et al., 1989; Longworth et al., 1994; Staub, 1994; Faltin et al., 1996). Similar mechanisms may be involved in the pathogenesis of ascites triggered in broilers by intratracheal inoculation with infectious bronchitis virus and *E. coli* (Tottori et al., 1997), or by pulmonary aspergillosis (Julian and Goryo, 1990). During endotoxin infusion in mammals, both the vasoconstrictor thromboxane and the vasodilator prostacyclin normally are produced, and can exert dynamically antagonistic influences on pulmonary vascular resistance (Longworth et al., 1994; Frank et al., 1996). Enhanced prostacyclin synthesis can attenuate the pulmonary vasoconstriction induced by hypoxia or metabolic acidosis in mammals (Farrukh et al., 1989; Yamagichi et al., 1989; Frank et al., 1996). The variable efficacy of aspirin on the incidence of ascites in broilers may reflect aspirin's nonspecific nullification of both the protective role of prostacyclin as well as the detrimental impact of thromboxane on pulmonary vascular resistance (Shlosberg et al., 1996; Balog et al., 1997; Wideman et al., 1999a).

The Inflammatory Response. The lungs of broilers developing ascites contain accumulations of mast cells, macrophages and inflammatory foci, as well as mineralized emboli and cartilagenous nodules (Maxwell et al., 1986, 1989; Owen et al., 1995a). During an inflammatory response, cells of the immune system are known to produce vasoactive substances (e.g. thromboxane, prostaglandins, serotonin) and inflammatory mediators (reactive oxygen species, cytokines, chemotactic factors) involved in pulmonary hypertensive and hypoxemic responses. Studies on the events occurring during the local inflammatory response in chickens have been reviewed by Klasing (1991), and focus primarily on the sequence of events following an inflammatory stimulus in the skin and gut (also a mucosal tissue). Heterophils and monocytes emigrate from the blood through venules within 30 minutes after the introduction of the inflammatory agent Shortly thereafter, emigrating monocytes outnumber heterophils. Once in the tissue, monocytes take on the appearance of macrophages. Heterophils disintegrate early in the response and their remnants are phagocytosed by macrophages. Basophils also arrive early at the site of inflammation, although their numbers may continue to increase substantially for 12 to 24 h depending on the type of stimulus; i.e., injection of endotoxin into the skin of chickens was characterized by substantial proportions of basophils emigrating into the tissues (Carlson, 1972; Stadecker et al., 1977; Dhodapkar et al., 1983; Nair, 1989; Katiyar et al., 1992). Another unusual feature of the early response to a local inflammatory stimulus consistently observed in chickens is the perivascular aggregation and proliferation of lymphocytes. These lymphocyte aggregates, consisting of T and B lymphocytes, form foci that may function as immune response induction sites and may be responsible for attracting basophils to the site of infection (Awadhiya et al., 1981; Nair, 1989; Klasing, 1991). Lastly, an additional distinguishing feature of the inflammatory response in chickens compared to most mammals is that in chickens macrophages present at the inflammatory site will form giant cells within 24 to 48 hours and, together with fibroblasts and fibrin will wall off the site of inflammation. In most mammals, this type of granuloma formation is generally observed in inflammatory responses mediated by inflammatory T helper cells (T helper cell type 1). These differences between chickens and mammals in the kinetics and cellular composition of the inflammatory response have been interpreted as evidence of an increased avian reliance on the inflammatory response (Carlson, 1982; Klasing, 1991).

Pulmonary Immune System. Although the local inflammatory response in the avian lung has not been specifically examined, several components involved in the immunological protection of the avian lung have been described. Airborne pathogens can enter the lungs and airsacs via the conducting airway system, which includes the trachea and primary and secondary bronchi. As in mammals, most airborne pathogens art prevented from entering into the deep lung by the mucociliary escalator present in the conducting airways and at the lung-air sac junction of chickens (McLelland, 1989a,b; Jeurissen et al., 1994; Fedde, 1998). The lymphoid tissues of bronchi primarily consist of demarcated oval lymphoid nodules present directly underneath the bronchiolar epithelial layer (Sminia er al., 1989; Jeurissen et al., 1994). This bronchus associated lymphoid tissue (BALT) can be most frequently observed at the junction of primary and secondary bronchi. The BALT has defined T and B cell areas, germinal centers and accessory cells, required for antigen presentation, suggesting a role of BALT in the initiation of mucosal immune responses. Lung tissues surrounding the non-cartilagenous, non-mucociliary tertiary bronchi (parabronchi) contain dentritic cells that may be important in the uptake and presentation of airborne antigen penetrating the parabronchus (Jeurissen et al., 1994).

Unlike mammalian species tit have alveolar macrophages as a first line of defense at their gas exchange surfaces, birds do not appear to have resident macrophages or other resident leukocytes at their gas exchange surfaces or within the air sacs. However, during respiratory infection or aspiration of particulates, leukocytes (primarily lymphocytes and heterophils) can be found in lavage fluid from the avian respiratory tract, indicating mechanisms do exist that allow these cells to enter the gas filled spaces when necessary (e.g., inflammation) (Ficken et al., 1986; Toth and Siegel, 1986; Toth et al., 1987, 1988; Klika et al., 1996; Kunkle and Rimler, 1996; Pruimboom et al., 1996). Immune cells are also present in the parenchyma of the lung. These include T cells and B cells as well as dentritic cells, macrophages, and mast cells. Among the parenchymal T cell population, various types of T cells have been identified, including those expressing $\alpha\beta1$ T cell receptors (TCR2+), $\alpha\beta2$ TCR (TCR3+) or $\gamma\delta$ TCR (TCR1+), CD4 molecules (CD4+) or CD8 molecules (CD8+)(Jeurissen et al., 1994; Erf and Wideman, unpublished).

Blood-Borne Delivery of Antipen to the Lungs. In addition to antigens entering the lungs through the inspired air, blood-borne antigens also gain access via the venous blood returning to the right ventricle of the heart. In sheep, horses, pigs and calves, blood-borne antigens circulating through the lung's capillaries are removed by pulmonary intravascular macrophages (PIM) (Brain et al., 1999). In normal sheep, PIMs have been shown to be responsible for 40 to 100% of uptake of intravenously injected tracer particles and have been shown to occupy 15% of the intravascular volume of pulmonary capillaries. Collectively they provide an extensive surface area for contact with bloodborne particles and constitute an important part of the mononuclear phagocytic system (Warner et al., 1986). PIMs are large mature macrophages that are bound to the pulmonary capillary endothelin by forming membrane adhesive complexes with the underlying endothelial cells. The complexes resemble adherent or intermediate junctions of endothelia and can be used to distinguish PIMs from adherent monocytes (Winkler, 1988; Brain et al., 1999). In chickens, as in the rat, studies on relative organ uptake of tracer particles and bacteria, revealed that more than 90% of circulating particles are removed from the blood in the liver, rather than the lung (Lund et al., 1921, Brain et al., 1999; Weidner and Lancaster, 1999). However, even in the absence of PIMS, i.v. endotoxin administration greatly enhances the pulmonary mononuclear cell uptake of circulating particles and pathogens in the rat (Warner et al., 1994). Furthermore, pretreatment of chickens with endotoxin apparently activated circulating leukocytes and enabled the microparticulate tracer Monastral blue (MB) to trigger a profound pulmonary hypertension that could not be elicited with injections of MB alone (Weidner and Lancaster, 1999). Similarly, endotoxin injected into chicken skin resulted in uptake of carbon particles by mononuclear cells in venules near the injection site, a process not observed in skin injected with saline alone. Other effects of endotoxin injury in chicken skin included increased vascular permeability, for up to 30 minutes post-injection, and leukocyte emigration (Katiyar er al., 1992). Hence, it is possible that in chickens, as in the rat, i.v. endotoxin administration may cause the release of mediators by pulmonary endothelial cells and circulating leukocytes leading to influx of other inflammatory cells. These changes induced by endotoxin may not only enhance the ability of the chicken pulmonary vasculature and leukocytes to remove blood-borne pathogens (Weidner and Lancaster, 1999), but also may contribute to cascading inflammatory events leading to pulmonary hypertension (Bottje and Wideman, 1995; Wideman et al., 1999a).

Taken together, the avian lung has developed mechanisms that protect against and eliminate air- and blood-borne pathogens. Although these mechanisms appear relatively inactive in the absence of an inflammatory stimulus (e.g., absence of resident respiratory macrophages at the air exchange surface; absence of PIMs in the pulmonary vasculature), they can be rapidly activated when needed (e.g., respiratory infection; endotoxin administration). The resulting local inflammatory response may then lead to conditions (pulmonary vasoconstriction; inflammatory foci) favorable to the development of pulmonary hypertension in susceptible individuals. Preliminary data recently obtained by Wideman and Erf (unpublished) support this conclusion (see below).

Preliminary Studies

Endotoxin. We are aware of only one previous study in which the pulmonary and systemic hemodynamic responses to endotoxin were evaluated in chickens. In that study, endotoxin did not trigger significant pulmonary hypertension because, by design, the dose used (15 $\mu$g endotoxin/kg BW) was sufficient to activate circulating leukocytes but too low to directly trigger hemodynamic responses (Weidner and Lancaster, 1999). Higher doses of endotoxin (5 mg/kg BW) recently were used to induce sustained fever and acute phase responses (elevated blood heterophils, elevated plasma interleukin 6 concentrations) in broilers (Xie et al., 2000). Pilot studies conducted in our laboratory confirm that endotoxin can cause pulmonary vasoconstriction and pulmonary hypertension in broilers (FIGS. 13A, 14A). Clinically healthy broilers (approx. 2 kg BW) injected i.v. with 1 mg of endotoxin exhibited a delayed onset ($\geq$15 min) pulmonary vasoconstriction that increased the pulmonary arterial pressure from a baseline value of 24 mm Hg to a peak value averaging $\geq$30 mm Hg within 20 to 25 min, followed by a gradual decline by 60 min post-injection. The pulmonary hemodynamic responses to the endotoxin injection occurred in spite of a contemporaneous reduction in the mean systemic arterial pressure (not shown). Supplemental 4 mg injections of endotoxin failed to reinitiate an additional pulmonary hypertensive response (FIG. 13A), however the responsiveness of the pulmonary vasculature to thromboxane was not attenuated (e.g., by prostacyclin) by a preceding 1 mg endotoxin injection (FIG. 14A). These observations are consistent with the hypothesis that the initial endotoxin injection initiated a biochemical cascade culminating in the delayed onset of pulmonary vasoconstriction. Subsequent to the peak pulmonary hypertensive response, depletion of key components of the cascade leading up to thromboxane production prevented 4-fold higher doses of endotoxin from reversing the return toward a normal pulmonary vascular tone and pressure. Preliminary histopathology of lung tissues obtained after endotoxin injections revealed vascular congestion, endothelial cell swelling, and notable increases in both large and small mononuclear cells within in the pulmonary microvasculature. The time-course and magnitude of the pulmonary hypertensive responses of individual broilers to endotoxin varied widely, for reasons that are not apparent based on attempts to maintain uniformity across all aspects of the experiment (FIGS. 13B, 14B). We hypothesize that the observed variability may reflect individual genetic differences related to key components of the vasoactive cascade, or that the prior immune history of individual birds, including the prevalence of pulmonary inflammatory foci, may modify the acquired responsiveness to endotoxin.

Blood-borne Particulates. The capacity of blood-borne particulates to physically lodge within the systemic or pulmonary microvasculature serves as the basis for using intravascularly injected microspheres of various sizes and compositions to measure the distribution of blood flow to various organs and tissues. A pulmonary vascular trapping efficiency of close to 100% has been validated for microspheres of $\geq$15 $\mu$m diameter in several avian species (Boelkins et al., 1973; Scheid and Holle, 1978; Brackenbury et al., 1990). Pilot studies conducted in our laboratory confirmed that intravenously injected particles of a suitable size and composition (60 $\mu$m diameter cellulose composites; patent pending) are trapped within the pulmonary vasculature, where they triggered rapid (within 20 minutes) and sustained focal inflammatory responses, pulmonary hypertension, and hypoxemia Pre-injection vs. 30-minute post-injection differences (P$\leq$0.05 for each) were, respectively, 21±1.5 vs. 30±1.0 mm Hg for pulmonary arterial pressure, 0.06±0.01 vs. 0.09±09.01 relative resistance units for pulmonary vascular resistance, and 95±1 vs. 93±1% for the saturation of arterial hemoglobin with oxygen (Wideman and Erf, unpublished). By forcing the cardiac output to flow through fewer vascular channels at higher pressures and flow rates, the trapped particles apparently promoted pulmonary edema and also exposed an incipient diffusion limitation that triggered the onset of systemic hypoxemia. Furthermore, injecting these particles i.v. in 3 week old broiler chicks triggered a 22.5% incidence of PHS, which more than tripled the 6.7% PHS incidence occurring in saline-injected control broilers by the termination of the experiment at 43 days of age (Wideman and Erf, unpublished).

Inflammatory Response. Histopathological examination of lung tissues obtained 20 min, 2, 5, 7, and 18 days after injecting particles into 22-day-old broilers, revealed progressive inflammation-associated changes in the lung parenchyma. Particles lodged in inter- and intra-parabronchial arterioles were surrounded by aggregates of thrombocytes within 20 minutes post-injection. Swelling of endothelial cells and congestion of capillaries with erythrocytes was also evident. Two days post-injection, tissues immediately surrounding occlusive particles were granulomatous, consisting primarily of mononuclear giant cells. Heterophils were only occasional observed, however basophilic cells were frequently seen within the granulomatous area and surrounding parenchyma. Lymphoid aggregates were present around the outer rim of the granuloma, although some lymphocytes were observed within the granulomatous tissue in close association with the occluded vessels. The lymphocyte foci consisted primarily of TCR2+ T cells expressing either CD4 or CD8. Some B cells were also observed within the foci. Staining for MHC class II expression revealed that most cells within and around the granuloma were MHC class II-positive cells, indicating an activated state of infiltrating T cells and macrophages. Five days post-particle injection, the lymphoid aggregates increased in size. Extensive perivascular lymphocyte aggregates were noted around venules located in close proximity to the occlusive particles. Frequently, these perivascular lymphoid aggregates were continuous with the lymphoid foci surrounding the particle and vessel. On Day 7 post-injection, lymphocyte infiltration was greatly reduced and the region around the occluded vessel appeared fibrous. With the exception of some fibrous tissues, little evidence of the inflammatory response remained when lung tissue was examined 18 days post-injection. Additionally, particles could no longer be observed trapped in the pulmonary vasculature. Lungs from saline injected time control broilers consistently exhibited substantially fewer and more poorly defined lymphoid aggregates. Overall, our preliminary observations demonstrate the induction of a marked inflammatory response following blood-borne particle presentation to the lungs of broilers (Erf and Wideman, unpublished).

Rationale and Significance

An important function of the mammalian pulmonary vasculature is to filter and clear the returning venous blood of particulate matter, such as aged red blood cells, micro- and macro-thromboemboli, bacteria, immune complexes, and cellular debris (Malik, 1983; Dantzker, 1997; Brain et al., 1999). Broilers have a cardiac output averaging $\geq 150$ mL/min per kg BW (Wideman, 1999) and a total blood volume averaging $\geq 8\%$ of BW (Sturkie, 1986a). Consequently, broiler lungs routinely process their entire blood volume within approximately 30 seconds. In addition to particulates entering the blood stream directly, materials engulfed by lymphatic capillaries throughout the body subsequently would flow through mural lymph nodes and major lymph trunks to empty into the vena cavae immediately proximal to the right atrium (Berens and Rautenfeld, 1993).

The pulmonary vasculature of broilers therefore can be challenged by a wide variety of particulates. The ability of the pulmonary vasculature to clear the blood of these particulates serves to defend sensitive tissues such as the brain and heart; however, this process of physically trapping and immunologically responding to particulates can be profoundly deleterious to pulmonary hemodynamics and gas exchange (Malik, 1983; Dantzker, 1997; Heffner and Repine, 1997). We hypothesize that the normal pulmonary function of entrapping particulates such as bacteria, thrombi, and cellular debris, can initiate or contribute to the pathogenesis of PHS through three interactive mechanisms. First, bacterial endotoxins are known to stimulate endothelin-mediated thromboxane-dependent increases in pulmonary vascular resistance leading to pulmonary hypertension in mammals (Morel et al., 1989; Faltin et al., 1996). Second, physical occlusion of vascular channels serves to directly increase the resistance to blood flow by reducing the overall cross-sectional area of the pulmonary vasculature. Third, the response of the immune system to endotoxin or entrapped particulates amplifies the pulmonary hypertensive and hypoxemic responses, due to the local release of vasoactive substances (endothelin-1, thromboxane, serotonin), as well as substances that affect the endothelin and surrounding tissues (reactive oxygen species).

Objectives

1. Characterize the immunologic and hemodynamic responses of broiler lungs to intravenously injected particles and endotoxin.

2. Determine whether prior activation of a multi-focal pulmonary inflammatory response, achieved by prior intravenous injections of particles, alters the magnitude, duration or individual variability of the subsequent pulmonary hypertensive response to endotoxin.

3. Determine whether individual variability in the pulmonary hypertensive response to endotoxin can be correlated with key indices of the inflammatory response profiles and the biochemical cascade initiated by endotoxin.

4. Compare these key indices among broilers from a commercial genetic base population and a PHS-resistant line previously selected from this base population.

Research Methods

Experimental Groups and Treatments. The proposed experimental groups and treatments are summarized in Table 5, with the detailed descriptions of each group or treatment being provided in subsections below. Initially, eight groups of broilers will be compared (groups A to H). Four of these groups will receive i.v. injections of particles within 2 hours prior to being evaluated (particle-primed groups: A,C,E,G), whereas the remaining four groups will not be injected with particles (unprimed groups: B,D,F,H). We will compare the responses of surgically anesthetized broilers (groups A to D) with the responses of unanesthetized broilers (groups E to H). Groups C,D,G and H will receive an endotoxin challenge similar to that shown in FIG. 3, whereas groups A, B, E, and F will serve as time controls. Our decision to use anesthetized or unanesthetized broilers for subsequent 3 day (groups I to L) or 10 day (groups M to P) particle pre-injection protocols will be finalized upon analysis of the initial experiments.

TABLE 5

Summary of experimental protocols using anesthetized or unanesthetized male broilers pre-injected with phosphate buffered saline (PBS) alone (unprimed) or with particles (primed) 2 hours, 3 days, or 10 days prior to inclusion in the time control or endotoxin challenge treatments. Endotoxin challenge protocol is shown in FIG. 3. The blood sample intervals are described in the text.

| Group | Pre-injection | Pre-injection Timing | Anesthesia Status (number of birds) | Endotoxin Challenge | Blood (5/bird) | Lungs (2/bird) |
| --- | --- | --- | --- | --- | --- | --- |
| A | Primed (PBS + particles) | 2 hours | Anesthetized (n = 8) | No (time control) | 40 | 16 |
| B | Unprimed (PBS alone) | 2 hours | Anesthetized (n = 8) | No (time control) | 40 | 16 |
| C | Primed (PBS + particles) | 2 hours | Anesthetized (n = 8) | YES (see FIG. 3) | 40 | 16 |
| D | Unprimed (PBS + particles) | 2 hours | Anesthetized (n = 8) | YES (see FIG. 3) | 40 | 16 |
| E | Primed (PBS + particles) | 2 hours | Unanesthetized (n = 8) | No (time control) | 40 | 16 |
| F | Unprimed (PBS alone) | 2 hours | Unanesthetized (n = 8) | No (time control) | 40 | 16 |
| G | Primed (PBS + particles) | 2 hours | Unanesthetized (n = 8) | YES (see FIG. 3) | 40 | 16 |
| H | Unprimed (PBS alone) | 2 hours | Unanesthetized (n = 8) | YES (see FIG. 3) | 40 | 16 |
| I | Primed (PBS + particles) | 3 days | To be determined (n = 8) | No (time control) | 40 | 16 |
| J | Unprimed (PBS alone) | 3 days | To be determined (n = 8) | No (time control) | 40 | 16 |
| K | Primed (PBS + particles) | 3 days | To be determined (n = 8) | YES (see FIG. 3) | 40 | 16 |
| L | Unprimed (PBS alone) | 3 days | To be determined (n = 8) | YES (see FIG. 3) | 40 | 16 |
| M | Primed (PBS + particles) | 10 days | To be determined (n = 8) | No (time control) | 40 | 16 |
| N | Unprimed (PBS alone) | 10 days | To be determined (n = 8) | No (time control) | 40 | 16 |
| O | Primed (PBS + particles) | 10 days | To be determined (n = 8) | YES (see FIG. 3) | 40 | 16 |
| P | Unprimed (PBS alone) | 10 days | To be determined (n = 8) | YES (see FIG. 3) | 40 | 16 |

Bird Source and Rearing. Male broilers derived from bio-secure base population maintained by a commercial broiler genetics company will be used (see attached letter from Dr. Howard French, Senior Geneticist, Hubbard ISA). The same source of chicks previously served as the base population from which a PHS-resistant line was selected (Wideman and French, 1999, 2000). Birds from the base population will be used for the initial series of experiments designed to characterize the key immunological and physiological indices correlated with individual variability in the pulmonary hypertensive response to particulates and endotoxin. Once the time course for key indices has been established additional experiments will be conducted to compare the responses of broilers from the base population and PHS-resistant line. Within the base population, the endotoxin responses of clinically healthy individuals will be compared with those of hatch-mate individuals identified as preascitic using previously established criteria (Wideman et al., 1998c, 2000; Forman and Wideman, 1999).

Chicks will be brooded and reared in stainless steel cages within the Poultry Environmental Research Laboratory on the Poultry Research Farm to maintain an essentially dust free environment with minimal exposure to pathogens. Temperatures will be 32 and 30° C. during weeks 1 and 2, and 24° C. thereafter. The birds will receive 24 hours of light during the first week, and 23 h light: 1 h dark thereafter. All birds will be fed the same corn- soybean meal-based broiler ration (crumbles days 1–14, pellets thereafter) prepared without animal byproducts by the University of Arkansas Poultry Feed Mill, and formulated to meet or exceed the minimum NRC (1994) standards for all ingredients, including 22.7% CP, 3,059 kcal/kg ME, 1.5% arginine, and 1.43% lysine.

Particle-Primed vs. Unprimed Birds. Cage mate broilers will be injected i.v. with heparinized (250 units ammonium heparin/mL) sterile phosphate buffered saline (PBS) carrier vehicle (unprimed) or heparinized PBS containing cellulose composite particles sufficient to elevate the overall incidence of PHS (particle-primed). The particles (60 μm average diameter cellulose composites; patent pending) will be autoclaved and suspended in the heparinized sterile PBS at a concentration previously determined based on the pulmonary vascular architecture (King et al., 1978), age (Duncker, 1978), and body weight (see Preliminary Studies). The particle priming injections therefore will create a sub-population known to be undergoing an active pulmonary inflammatory response associated with pulmonary hypertension. The injections will occur within 2 hours (acute response), 3 days (intermediate responses), or 10 days (prolonged response) prior to conducting the endotoxin challenge (Table 5).

Endotoxin Challenge. The endotoxin challenge will follow the protocol shown in FIG. 13A or 13B. Bacterial endotoxin (lipopolysaccharide, LPS, from *Salmonella typhimurium*, Sigma L7261) will be dissolved at 5 and 20 mg/mL in sterile PBS, and 0.2 mL/2 kg BW (1 and then 4 mg LPS) will be injected i.v. into the cutaneous ulnar vein (wing vein). The need for in vivo dose-response studies has been preempted by our prior determination that 1 mg i.v. endotoxin/2Kg BW evoked the maximum pulmonary hypertensive response attainable in individual broilers. After the peak response to the 1 mg i.v. injection has been observed, an additional 4 mg of endotoxin is injected i.v. to confirm that a maximal pulmonary hypertensive response was attained (FIGS. 13A–14B; see Preliminary Studies).

Fully Instrumented—Suraically Anesthetized Broilers. The techniques for recording pulmonary arterial pressure, cardiac output, and systemic arterial pressure have been described previously (Wideman and Kirby, 1995b; Wideman et al., 1996a,b, 1998a, 1999a,b, 2000; Wideman, 1999), and have been approved as protocol number 98009 by the University of Arkansas IACUC. Briefly, male broilers 35 to 49 days of age and averaging 2 kg BW will have ad libitum access to feed and water until they are anesthetized to a surgical plane with allobarbital (5,5-diallyl-barbituric acid; 25 mg kg/BW). They will be fastened in dorsal recumbency on a surgical board thermostatically regulated to maintain a surface temperature of 30° C. An ultrasonic flow probe connected to a Transonic T206 blood flow meter will be positioned on the right pulmonary artery. The left pulmonary artery will be cannulated with Silastic tubing, and the distal end of the cannula will be attached to a blood pressure transducer to record pulmonary arterial pressure. A wing vein and brachial artery will be cannulated with PE-50 polyethylene tubing for i.v. injections and infusions (venous cannula), and for blood sample withdrawal and continuous monitoring of systemic arterial pressure (arterial cannula). For data collection, the blood flow meter and blood pressure transducers are digitally interfaced to a computer (Biopac MP 100 data acquisition system using AcqKnowledge software). The primary channels recorded will include blood flow through the right pulmonary artery, pulmonary arterial pressure, and mean systemic arterial pressure. Average values for blood flow, pulmonary arterial pressure, mean systemic arterial pressure, heart rate, cardiac output, stroke volume, pulmonary vascular resistance, total peripheral resistance, and respiratory rate will be determined as described previously (Wideman, 1999).

Blood and Tissue Sample Collection. When surgical preparations are complete and a 20 min. stabilization period has elapsed, control data will be recorded for 20 min. Broilers then will be injected through the wing vein cannula with 0.2 mL of PBS alone (unprimed and particle-primed time control groups), or with 1 mg and then 4 mg of LPS/2 kg BW according to the protocol shown in FIG. 3 (unprimed and particle-primed endotoxin groups). Physiological data will be recorded throughout the experiment. Arterial blood samples (1.5 mL) will be withdrawn at the start of the initial control period (sample 1), 5 min after the first LPS injection (sample 2), coincident with the peak pulmonary hypertensive response (sample 3), 5 min after the second LPS injection (sample 4), and at the termination of the experiment (sample 5). Within 15 seconds after anaerobic withdrawal of each arterial blood sample, a 0.3 mL portion will be injected into a Radiometer ABL 330 Acid-Base laboratory for determination of pH, $PO_2$, $PCO_2$ and $HCO_3$, adjusted for an avian body temperature of 41° C. (Wideman et al., 1996a,b; 1998a,b). Be remaining blood will be centrifuged immediately and the plasma stored at −80° C. for subsequent analyses. Blood for biochemical analyses will be collected, and the will be plasma separated and stored, in accordance with precautions necessary to minimize serotonin and thromboxane release or metabolism by cellular components (see below). Each bird will be humanely euthanized, the lungs prepared for histological and immunohistochemical evaluation, and the heart dissected and weighed to determining the RV:TV ratio as an index of sustained pulmonary hypertension (Huchzermeyer et al., 1988).

Unanesthetized Broilers. To evaluate the influence of general anesthesia and surgical preparation on the pulmonary hypertensive responses to endotoxin,pulmonary arterial pressures also will be measured using acutely cannulated unanesthetized broilers (approved as protocol number 98009 by the University of Arkansas IACUC). Broilers will be lightly restrained in lateral recumbency, and a 2% lidocaine solution will be infiltrated intracutaneously as a local anesthetic along the left cutaneous ulnar vein, which then will be cannulated with Silastic® tubing. The cannula will be advanced into the pulmonary artery as judged by pressure tracings (Owen et al., 1995b; Wideman et al., 1999a,b, 2000). Arterial and venous cannulae also will be inserted into the brachial artery and wing vein under local anesthesia The birds then will be supported in an upright posture within a darkened compartment while the pulmonary arterial pressure, systemic arterial pressure and heart rate are recorded. In the absence of a flow probe, cardiac output, pulmonary vascular resistance, and total peripheral resistance cannot be determined on a continuous basis. However, acute changes in pulmonary arterial pressure qualitatively mirror changes in pulmonary vascular resistance (FIGS. 11A–14B), and virtually identical pulmonary arterial pressure responses to inhalation of 100% or 12% $O_2$ recently were observed when unanesthetized broilers were compared with anesthetized, fully instrumented broilers (Wideman et al., 2000; Ruiz-Feria and Wideman, unpublished observations). We anticipate the pulmonary hypertension induced by endotoxin in unanesthetized broilers will exhibit a range of individual variability similar to the responses of anesthetized and fully instrumented broilers (FIGS. 13A–14B). If significant qualitative differences are detected, then the unanesthetized preparation can be used for subsequent experiments, and we will forgo direct assessments of cardiac output and vascular resistances. It is the amplitude of pulmonary hypertension, per se, that is most directly predictive of the pathogenesis leading to PHS (Wideman, 2000). This simplified unanesthetized preparation will be used in accordance with the protocols described above for the fully instrumented surgically anesthetized broilers (unprimed or particle-primed time control groups; unprimed or particle-primed endotoxin groups), and will serve as a source of additional tissues and blood samples.

Processing and Evaluation of Blood and Tissue Samples.

Biochemical Analysis of Plasma Samples: Plasma samples will be analyzed to determine the level of vasoactive and inflammatory factors. The factors chosen to be measured in the proposed study are thromboxane $B_2$ ($M_2$), serotonin, endothelin, and interleukin-6 (IL-6).

i. Thromboxane $B_2$ is a stable metabolite, and a reliable indicator of the formation, of active $TXA_2$, a potent pulmonary vasoconstrictor released by activated platelets and thrombocytes (Machin, 1992). Thromboxane has been shown to increase pulmonary arterial pressure in broilers (FIGS. 11A, 11B, 14A, 14B), and thrombocytes, capable of releasing $TXA_2$, were the first cell type observed to associate with the occluding i.v. injected particle (see preliminary studies). Therefore, examination of thromboxane production will be a focus of the proposed studies. The circulating levels of $TXB_2$ will be determined using the Cayman Chemical Enzyme Immunometric Assay kit following the manufacturer's instructions for sample collection, preparation and assays (Thromboxane $B_2$ EIA Kit # 519031).

ii. Serotonin (5-Hydroxy tamine, 5-HT), also a potent pulmonary vasoconstrictor, is actively accumulated by mammalian platelets and avian thrombocytes and released into the plasma during platelet or thrombocyte aggregation (Meyer and Sturkie, 1974; Cox, 1985; Lacoste-Eleaume et al., 1994). Plasma serotonin levels increased markedly during gram-negative sepsis, and elevated plasma concentrations of serotonin have been implicated in the pulmonary hypertension associated with acute respiratory disease syndrome in humans (Heffner and Repine, 1997). In domesticated avian species, biogenic amines are known to cause pulmonary vasoconstriction (see Wideman, 1999) and to have biological effects on thrombocytes, as shown by thrombocyte aggregation in response to serotonin in vitro (Belamarich el al., 1968). However, neither the in vivo pulmonary vascular response to serotonin nor its biological interaction with thrombocytes has been evaluated in broilers. Plasma levels of serotonin will be determined by the Central Analytical Laboratory of the Poultry Science Center using an electrochemical assay (see attached letter from Dr. Kelly Beers, Director. Central Analytical laboratory). The pulmonary hemodynamic efficacy of serotonin (Sigma H9523) also will be evaluated in broilers using a protocol similar to that shown for thromboxane in FIGS. 14A–14B, as a means of assessing the ongoing responsiveness to this vasoconstrictor during the biochemical cascade triggered by endotoxin.

iii. Endothelin has been described as an extremely potent vasoconstrictor released by activated or injured endothelial cells (Coessens, 1994). Endothelin is known to exert its vasoconstrictive effects via thromboxane, however, this may not be the only pathway by which endothelin initiates vasoconstriction. Mammalian endothelin (human and porcine) constricts pulmonary artery rings from broilers (Martinez-Lemus et al., 1998), and the expression patterns of endothelin-A and B receptors, as well as, of endothelin-1 and −3 have been described for the avian embryo (Nataf et al., 1998a,b). Hence, the measurement of endothelin levels in the circulation, and examination of endothelin production in situ (see Histology below), may yield insight into the role of endothelial cells in endotoxin- and/or particle induced pulmonary vasoconstriction. Plasma endothelin will be measured using the Cayman Chemical Enzyme Immunometric Assay kit (#583151), although species cross reactivity has not been tested at this time. As described below endothelin production will also be examined in situ, independent of our ability to examine endothelin levels in the plasma. The pulmonary hemodynamic efficacy of endothelin-1 (human, porcine, Sigma E7764) also will be evaluated in broilers using a protocol similar to that shown for thromboxane in FIGS. 14A–14B, as a means of assessing the ongoing responsiveness to this vasoconstrictor during the biochemical cascade triggered by endotoxin.

iv. Interleukin-6 is a cytokine released during the acute and chronic inflammatory response. Although, the measurement of cytokines found in plasma during the avian inflammatory response (e.g., IL-1, IL-6, IL-8, IL-12, TNF-$\alpha$, INF$\gamma$) has been hampered by the lack of specific cytokine assays, IL-6 can be measured using the B9 mouse hybridoma proliferation bioassay (Rath et al., 1995). Using this bioassay, IL-6 has been shown to be present in elevated levels in the plasma following endotoxin administration in chickens (Xie et al., 2000) and in ascites fluid from broilers with pulmonary hypertension syndrome (Rath et al., 1995). IL-6 levels in plasma samples will be determined with guidance from Dr. N. C Rath, USDA-ARS, using the B9 hybridoma assay. As more assay systems become available to measure inflammation-associated cytolkines in chickens [e.g., assay systems to measure interleukin 8 (IL-8), IL-15, and INF$\gamma$ are expected to be available in the near future], measurements of these cytokines will be included in the proposed studies.

Peripheral Blood Cell Analyses: During the inflammatory response, leukocytes are attracted to inflamed tissues where they emigrate from the circulatory system to fight off the inflammation-inducing agent Additionally, inflammation will result in elevated production of leukocytes in the bone marrow and/or result in recruitment of leukocytes from storage tissues into the blood (Klasing, 1991; Paul, 1999). As a result, the proportions among, and the concentrations of, blood leukocytes may change throughout the course of inflammation. Examination of blood leukocyte profiles will therefore provide insight into events following i.v. injection of endotoxin and/or particles. Blood leukocyte profiles in whole blood samples will be monitored using a multi-parameter, automated hematology analyzer that has been calibrated for analysis of chicken blood (CELL-DYN 3500SL). Using the CELL-DYN 3500 SL system, the following aspects will be determined: 1) leukocyte, erythrocytes, and thrombocyte concentrations (# of cells/$\mu$L of blood); 2) the concentrations of, and proportions among individual blood leukocyte populations (lymphocytes, heterophils, monocytes, eosinophils and basophils); 3) hematocrit values (%); and; 4) mean corpuscular volume (fL) and mean corpuscular hemoglobin (pg and g/dL). These data will provide insight into both, changes in leukocyte profiles and respiration-associated blood components following inflammatory stimuli. Studies conducted by Erf (unpublished) have shown that broiler data obtained using the CELL -DYN 3500SL system closely match data obtained using conventional methods [Natt-Herrick's solution and a hemacytometer to determine erythrocytes and leukocyte concentrations; Wright stained blood films to determine the proportions among blood leukocyte populations]. However, blood films will also be prepared and stained with Wright stain (Lucas and Jamroz, 1961) for morphological examination of leukocytes and thrombocytes using a bright-field microscope (111x).

To determine changes in the proportions among peripheral blood lymphocyte subpopulations in response to inflammatory stimuli, peripheral mononuclear cell suspensions will be prepared using Ficoll density gradient centrifugation. Cells will then be incubated with a panel of monoclonal antibodies. Included in the panel are antibodies specific for chicken lymphocytes (K55), T cells (CD3), B cells (Bu-1), T helper cells (CD4), cytotoxic T cells (CD8), T cells expressing either a $\gamma\delta$ T cell receptor (TCR1) or one of the two types of $\alpha\beta$ T cell receptors (TCR2, TCR3) (Table 6).

TABLE 6

Chicken Immune Cell Markers

| Antibody to[1] | Cell type(s) identified |
|---|---|
| CD3 | All T cells; complex of molecules associated with T cell receptor, T cells make up about 75–85% of peripheral blood lymphocytes (PBL). |
| CD4 | T helper cell; MHC class II restricted, 35–45% of PBL. |
| CD8 | T cytotoxic/suppressor cell; MHC class I restricted, 10–20% of PBL. |
| TCR1 | T cell expressing a $\gamma\delta$ T cell receptor (TCR); 15–30% of PBL, first type of T cell to appear in ontogeny, may be co-expressed with CD8 in spleen, does not co-express CD4. |
| TCR2 | T cell expressing an $\alpha\beta$1 T cell receptor; express either CD4 or CD8, use the v$\beta$1 variable gene fragment for the TCR $\beta$-chain gene, required for production of IgA. |
| TCR3 | T cell expressing a different $\alpha\beta$2 T cell receptor; used v$\beta$2 variable gene fragment for the TCR $\beta$-chain gene, 10–15% of PBL. |
| Bu-1 | B cells but not plasma cells; 15–25% of PBL. |
| Ig | B cells surface protein; functional analogues of mammalian IgM, IgG, and IgA. |
| K55 | All lymphocytes (Chung et al., 1991, Vet. Immunol. Immunopathol., 28, 259). |
| K1 | Macrophage/monocyte (Kaspers et el., 1993, Vet. Immunol. Immunopathol., 36, 333). |
| IL-2R | Activated T cells (INN-CH-16). |
| MHC class II | Antigen-presenting cells and activated T cells (B-L in chickens). |

[1]Unless indicated otherwise, see Chen et al., 1991 for source.

Antibodies K55 and Bu-1 (mix) are anti-chicken mouse monoclonal hybridoma culture supernates and will be used as primary antibodies in an indirect immunofluorescence staining procedure followed by one-color analysis using a flow cytometer (FACSort, Becton Dickinson). Antibodies to CD3, CD4, CD8, TCR1, TCR2, and TCR3 are directly conjugated anti-chicken mouse monoclonal antibodies (Southern Biotech. Assoc., Inc. Birmingham, Ala.). These antibodies will be used in a direct immunofluorescence staining procedure followed by one-, two-, or three-color flow cytometric analysis. Direct and indirect staining procedures, as well as, flow cytometric cell population analyses will be carried out as described by Erf and co-workers (Erf and Smyth, 1996; Erf, 1997; Erf et al., 1998a,b).

Histology: Both lungs will be collected from each bird to be used for conventional histology and for immunohistochemistry. Immediately following collection, the left lung will be put into 10% buffered formalin and the right lung will be prepared for freezing. Prior to freezing, the right lung will be cut in half by cutting transversely between the second and third rib indentation. Each half will then be placed cut-face down (cranial and caudal portions separately) into a labeled aluminum cup, covered with freezing medium, and snap frozen in liquid nitrogen as described by in Erf et al. (1995, 1997). The left lung will be cut and oriented in the same manner during the preparation of paraffin-embedded tissue blocks. Histopathological effects of inflammatory stimuli on lung tissue will be examined using 5 $\mu$m tissue sections from paraffin-embedded and frozen lung tissues. Examination of these tissues will provide insight into the type, location, amount, and proportions among various leukocyte populations present in lung parenchyma and BALT following i.v. injection of endotoxin and/or particles. We initially will focus specifically on the lungs from broilers exhibiting the most extreme (maximal or minimal) pulmonary hypertensive responses to particle and endotoxin injections.

i. Paraffin sections Paraffin tissue sections will be prepared and stained in the Histology service laboratory located in the Center for Poultry Science. To optimize the ability to identify various types of leukocytes and tissues, several staining methods will be employed. Included are the May-Grünwald Giemsa stain (leukocyte identification), Hematoxilyn and Eosin stain (general architecture), Toludine Blue stain (mast cells), and the Trichrome stain (keratin, muscle fibers and collagen) (Lucas and Jamroz, 1961; Humason, 1972; Dhodapkar et al., 1983; Campbell, 1988; Maxwell and Robertson, 1995). Additionally, paraffin-embedded tissue sections will be stained with a fluorescein stain for heterophils (Rath et al., 1998) and an indirect immunofuorescent stain using species non-specific rabbit anti-endothelin polyclonal antibody (Endothelin Ab-2, Calbiochem-Novabiochem, International # PC266) as the primary antibody. Using a 10 mm ocular grid the number of various types of leukocytes in lung tissue will be quantified and data expressed as number of cells/mm$^2$ (Erf et al., 1995, 1997). Additionally, immunofluorescently stained sections will be quantitatively evaluated by image analysis using Image-Pro software.

ii. Immunohistochemistry using frozen tissue sections: Frozen tissue sections will be prepared and stained by Erf and co-workers. A panel of mouse anti-chicken monoclonal antibodies, and an indirect immunoperoxidase staining procedure described by Erf et al. (1995, 1997) will be used to identify various lymphocyte populations and macrophages. The binding of primary antibody specific for chicken CD3, CD4, CD8, Bu-1, IgM, IgG, IgA, macrophages (K1), MHC class II, TCR1, TCR2, or TCR3 (Table 6) will be detected using a biotin-conjugated horse anti-mouse IgG or IgM (depending on the isotype of the primary antibody) and the reagents supplied in the Vekta Stain Elite kit (enzyme-labeled biotin, avidin, and DAB substrate). Tissues will be counter-stained with Methyl green stain (Lucas and Jamroz, 1961) and microscopically examined for location of various cell types. The amount of each cell type present in the lung and in BALT will be quantified by image analysis using Image-Pro software. Data will be expressed as number of cells/mm$^2$ (e.g., lung parenchyma) and/or the percentage of total area examined (e.g., for BALT, inflammatory foci).

Results Expected.

Pilot studies have demonstrated that the particle-priming injections will create an active pulmonary inflammatory response associated with the rapid onset of pulmonary hypertension, right ventricular hypertrophy, and systemic arterial hypoxemia. We expect these effects will persist in the particle-primed as opposed to the unprimed groups throughout the 2 hour to 3 day post-injection periods, but may subside by 10 days post-injection. Immunological and physiological differences related to particle priming will be revealed by intergroup comparisons between primed and unprimed groups. Pilot studies indicate the acute response (within 2 hours) will include aggregates of thrombocytes surrounding particles lodged in the pulmonary parenchyma. During this acute phase, and at 3 days post-particle injection, endotoxin is likely to evoke consistently higher amplitude pulmonary hypertensive responses in particle-primed than unprimed broilers. Anesthetized and unanesthetized broilers are expected to exhibit qualitatively similar responses.

Individual variability in the pulmonary hypertensive response to endotoxin is likely to be positively correlated with evoked levels of endothelin, thromboxane, or serotonin. In turn, we hypothesize that prior initiation of inflammatory foci within the lungs (by particle-priming) will be identified as an important acquired feature that will permit endotoxin to trigger consistently amplified pulmonary hypertensive responses. Individual and group differences in the blood biochemical indices, as well as blood leukocyte profiles, are expected to reveal readily identifiable response patterns that will be predictive of the magnitude of the pulmonary hypertension induced by particulates and endotoxin The PHS-resistant line has been selected specifically to have a superior pulmonary vascular capacity. Consequently, we hypothesize that equivalent particle or endotoxin injections will trigger a lower increment in pulmonary arterial pressure in the PHS-resistant line (proportionally less impact of vascular obstruction, inflammatory mediators or vasoconstrictors on pulmonary vascular resistance) than in the base population.

Means by Which Experimental Data will be Analyzed or Interpreted. Physiological data will be collected according to the sample intervals shown in FIGS. 13A–13B. Blood samples (5 from each bird) and tissue samples will be collected as described above. To evaluate the differences between particle-primed and unprimed groups, inter-group comparisons will be made for the control sample intervals (FIGS. 13A–13B) within each of the major experiments shown in Table 5, using the Sigma State Analysis of Variance (ANOVA) procedure. To evaluate the time-course of changes induced by endotoxin, intra-group data will be analyzed over time (across sample intervals within the groups shown in Table 5) using the Sigma Stat® Repeated Measures ANOVA procedure, with means differentiated by the Student-Newman-Keuls method. The differences in endotoxin responsiveness between particle-primed and unprimed groups within each experiment will be compared by ANOVA within contemporaneous sample intervals. Coefficients of variation will be used to quantify the individual variability within each group. Linear regression analysis will be used to correlate the pulmonary hypertensive response to endotoxin and key indices of the inflammatory response profiles or the biochemical cascade initiated by endotoxin.

Pitfalls and Limitations that may be Encountered. The proposed experiments are soundly based on evidence available in the literature as well as the highly promising results of the pilot studies. The proposed work clearly falls within the established technical competence, credentials, and experience of the principal investigators. Research of this type initially must be exploratory and descriptive in nature, as necessitated by the current paucity of knowledge regarding interactions between the immunologic and hemodynamic responses of broiler lungs to blood-borne particulates and endotoxin. Such interactions have a direct relevance to the pathogenesis of PHS in broilers. Although not directly addressed in the current proposal, the inflammatory and hemodynamic responses to blood-borne antigens also are relevant to responses triggered by antigens carried to the gas exchange surfaces by inspired air. Whole animal experiments are required for studies of the complex multi-system interactions related to PHS. The initial experimental series has been well defined in the current proposal, and will lead directly toward accomplishing Objectives 1 to 3. However, the protocols of subsequent experiments must remain flexible to permit fine-tuning as deemed appropriate. For example, we have addressed the possibility that valuable hemodynamic data (cardiac output, stroke volume, vascular resistances) will be conceded if substantial differences in key indices require the use of unanesthetized instead of surgically anesthetized and fully-instrumented broilers. We have pointed out that pulmonary arterial pressure will be measured when unanesthetized broilers are used, and it is the amplitude of pulmonary hypertension, per se, that is most directly predictive of the pathogenesis leading to PHS. This flexibility, inherent to exploratory and descriptive research, is essential to optimizing our approach to accomplishing the research objectives. Addressing the first three objectives will not permit a full differentiation between genetic and/or acquired causes for the widely varied individual responses to endotoxin. That differentiation can only be accomplished by addressing Objective 4, which in turn will prove the applied relevance of this work to commercial poultry breeders. One uncertainty with all of these studies lies in the ability to assay chicken plasma endothelin concentrations using a commercial kit for which the species cross-reactivity has not been tested. If this kit proves unreliable in initial evaluations (plasma from broilers with or without i.v. endotoxin injections), we intend to pursue small-scale evaluations of other endothelin assays. As addressed in the Research Methods section, the pulmonary hemodynamic efficacy of intravenously administered endothelin-1 will be evaluated using a protocol similar to that shown for thromboxane in FIGS. 14A–14B, as a means of assessing the ongoing responsiveness to endothelin during the biochemical cascade triggered by endotoxin.

Changes may be made in the construction and the operation of various components, elements and assemblies described herein or in the steps or the sequence of steps of the methods described herein without departing from the spirit and scope of the invention as defined in the following claims.

References

All citations listed above and below are incorporated by reference herein for details supplementing this application:

Balog, J. M., G. R. Bayyari, N. C. Rath, and W. E. Huff, 1997. Effect of dietary aspirin on ascites syndrome in broilers. Poultry Sci 76 (Supplement 1):96.

Barens, D., and V. Rautenfeld, 1993. System lymphaticum et splen. Pages 477–491 in: Handbook of Avian Anatomy: Nomina Anatomica Avium. $2^{nd}$ ed. J. J. Baumel, A. S. King et al., ed. Nuttal Ornithological Club, c/o Museum of Comp. Zool., Harvard Univ., Cambridge, Mass.

Bottje, W. G., and R. F. Wideman, 1995. Potential role of free radicals in the pathogenesis of pulmonary hypertension syndrome. Poultry and Avian Biol. Rev. 6:211–231.

Bottje, W. G., S. Wang, F. J. Kelly, C. Dunster, A. Williams, and I. Mudway, 1998. Antioxidant defenses in lung lining fluid of broilers: impact of poor ventilation conditions. Poultry Sci. 77:516–522.

Brain, J. D., R. M. Molina, M. M. DeCamp, and A. E. Warner, 1999. Pulmonary intravascular macrophages: their contribution to the mononuclear phagocyte system in 13 species. Am. J. Physiol. 276:L146–L154.

Brown, R. E., J. D. Brain, and N. Wang, 1997. The avian respiratory system: a unique model for studies of respiratory toxicosis and for monitoring air quality. Environ. Hlth. Perspect. 105:188–200.

Burton, R. R., E. L. Besch, and A. H. Smith, 1968. Effect of chronic hypoxia on the pulmonary arterial blood pressure of the chicken. Am. J. Physiol. 214:1438–1442.

Cueva, S., H. Sillau, A. Valenzuela, and H. Ploog, 1974. High altitude induced pulmonary hypertension and right ventricular failure in broiler chickens. Res. Vet. Sci. 16:370–374.

Dantzker, D. R., 1997. Pulmonary embolism. Pages 1599–1607 in: The Lung: Scientific Foundations. $2^{nd}$ ed. R G. Crystal, J. B. West, P. J. Barnes, E. R. Weibel, ed. Lippincott-Raven, Philadelphia, Pa.

Faltin, D. L., A. Weber, J. S. Lacroix, M. Jorge-Costa, and D. R Morel, 1996. Lung mechanics and pulmonary but not systemic vascular responses to ET-1 are Tx and infusion rate dependent. J. Appl. Physiol. 80:1716–1723.

Farrukh, I. S., G. H. Gurtner, P. B. Terry, W. Tohidi, J. Yang, N. F. Adkinson, Jr., and J. R. Michael, 1989. Effect of pH on pulmonary vascular tone, reactivity, and arachidonate metabolism. J. Appl. Physiol. 67:445–452.

Fedde, M. R., 1986. Respiration. Chapter 6, pp191–220 In: *Avian Physiology*, 4th edition. P. D. Sturkie, ed. Springer-Verlag, New York, N.Y.

Fedde, M. R., 1998. Relationship of structure and function of the avian respiratory system to disease susceptibility. Poultry Sci. 77:1130–1138.

Fedde, M. R., and R. F. Wideman, 1996. Blood viscosity in broilers: influence on pulmonary hypertension syndrome. Poultry Sci. 75:1261–1267.

Fedde, M. R., G. E. Weigle, and R. F. Wideman, 1998. Influence of feed deprivation on ventilation and gas exchange in broilers: relationship to pulmonary hypertension syndrome. Poultry Sci. 77:1704–1710.

Forman, M. F., and Wideman, R. F., 1999a. Renal responses of normal and preascitic broilers to systemic hypotension induced by unilateral pulmonary artery occlusion. Poultry Sci. (in press).

Frank, D. U., S. M. Lowson, C. M. Roos, and G. F. Rich, 1996. Endotoxin alters hypoxic pulmonary vasoconstriction in isolated rat lungs. J. Appl. Physiol. 81:1316–1322.

Huchzermeyer, F. W., and A. M. C. DeRuyck, 1986. Pulmonary hypertension syndrome associated with ascites in broilers. Vet. Rec. 119:94.

Huchzermeyer, F. W., A. M. C. DeRuyck, and H. Van Ark, 1988. Broiler pulmonary hypertension syndrome. III. Commercial broiler strains differ in their susceptibility. Onderstepoort J. Vet Res. 55:5–9.

Hughes, J. D., Jr., R. F. Wideman, Jr., N. B. Anthony, J. D. Kirby, L. L. Kinder, and L. K. Stamps, 1997. Incidence of ascites induced by unilateral bronchus occlusion in commercial broilers, giant jungle fowl, and their reciprocal crosses. Poultry Sci. 76 (Suppl. 1):114.

Jandel Scientific, 1994. SigmaStat® *Statistical Software User's Manual*. Jandel Scientific Software, San Rafael, Calif.

Julian, R. J., 1988. Pulmonary hypertension as a cause of right ventricular failure and ascites in broilers. Zootecnica International (November, #11):58–62.

Julian, R. J., 1989. Lung volume of meat-type chickens. Avian Dis. 33:174–176.

Julian, R. J., 1993. Ascites in poultry. Avian Pathol. 22:41–454.

Julian, R. J., and M. Goryo, 1990. Pulmonary aspergillosis causing right ventricular failure and ascites in meat-type chickens. Avian Pathol. 19:643–654.

King, A. S., 1966. Structural and functional aspects of the avian lungs and air sacs. Int. Rev. Gen. Exp. Zool. 2:171–267.

King, A. S., 1993. Apparatus respiratorius (systema respiratorium). Chapter 8, pp257–299 In: *Handbook of Avian Anatomy: Nomina Anatomica Avium*, 2nd edition. J. J. Baumel, A. S. King, J. E. Breazile, H. E. Evans, and J. C. Vanden Berge, eds. Nuttal Ornithological Club, c/o Museum of Comp. Zool., Harvard Univ., Cambridge, Mass.

King, A. S., and V. Molony, 1971. The anatomy of respiration, Chapter 5, pp93–169 In: *Physiology and Biochemistry of the Domestic Fowl*. Volume 1. D. J. Bell and B. M. Freeman, eds. Academic Press, New York, N.Y.

King, A. S., and J McLelland, 1984. Respiratory system. Chapter 7, pp110–144 In: *Birds. Their Structure and Function*, 2nd edition. Bailliere Tindall, London.

King, A. S., D. Z. King, and M. A. Abdalla, 1978. The structure of the intrapulmonary vasculature of the domestic fowl. Pages 112–124 in: Respiratory Function in Birds, Adult and Embryonic. J. Piiper, ed. Springer-Verlag, New York, N.Y.

Kirby, Y. K., R. W. Mcnew, J. D. Kirby, and R F. Wideman, Jr., 1997. Evaluation of logistic versus linear regression models for predicting pulmonary hypertension syndrome (ascites) using cold exposure or pulmonary artery clamp models in broilers. Poultry Sci. 76:392–399.

Kochera-Kirby, Y. K, N. B. Anthony, J. D. Hughes, R. W. McNew, J. D. Kirby, and R. F. Wideman, 1999a. Electrocardiographic and genetic evaluation of clinically healthy broilers and giant jungle fowl following unilateral bronchus occlusion. Poultry Sci. 78:125–134.

Kochera-Kirby, Y. K., R. W. McNew, N. B. Anthony, N. E. Marson, J. D. Hughes, J. D. Kirby, and R F. Wideman, 1999b. Electrocardiographic evaluation of broilers following unilateral occlusion of an extrapulmonary primary bronchus. Poultry Sci. 78:242–254.

Longworth, K. E., K. A. Jarvis, W. S. Tyler, E. P. Steffey, and N. C. Staub, 1994. Pulmonary intravascular macrophages in horses and ponies. Am. J. Vet Res. 55:382–388.

Loyd, J. E., and J. H. Newman, 1997. Familial primary pulmonary hypertension. Pages 151–162 In: Primary Pulmonary Hypertension, Volume 99 in Lung Biology in Health and Disease. L. J. Rubin and S. Rich, eds. Marcel Dekker, Inc., New York, N.Y.

Maina, J. N., 1984. Morphometrics of the avian lung. 3. The structural design of the passerine lung. Resp. Physiol. 55:291–307.

Maina, J. N., and A. S. King, 1982. The thickness of the avian blood-gas barrier: qualitative and quantitative observations. J. Anat 134:553–562.

Marshall, B. E., and C. Marshall, 1992. Acidosis and the pulmonary circulation. Pages 99–115 in: Hypoxia, Metabolic Acidosis, and the Circulation. A. I. Arieff, ed. Oxford University Press, New York, N.Y.

Maxwell, M. H., and G. W. Robertson, 1997. World broiler ascites survey 1996. Poultry International, October: 26–32.

Maxwell, M. H., and G. W. Robertson, 1998. UK survey of broiler ascites and sudden death syndromes in 1998. Br. Poultry Sci. 39:203–215.

Morel, D. R., J. S. Lacroix, A. Hemsen, D. A. Steinig, J. -F. Pittet, and J. M. Lundberg, 1989. Increased plasma an pulmonary lymph levels of endothelin during endotoxin shock Euro. J. Pharmacol. 167:427–428.

National Research Council, 1984. Nutrient Requirements of Poultry. 8th rev. ed. National Academy Press, Washington, D.C.

Odom, T. W., 1993. Ascites syndrome: overview and update. Poultry Digest 52: 14–22.

Owen, R. L., R. F. Wideman, Jr., A. L. Hattel, and B. S. Cowen, 1990. Use of a hypobaric chamber as a model system for investigating ascites in broilers. Avian Dis. 34:754–758.

Owen, R. L., R. F. Wideman, R. M. Leach, B. S. Cowen, P. A. Dunn, and B. C. Ford, 1994. Effect of age of exposure and dietary acidification or altalinization on mortality due to broiler pulmonary hypertension syndrome. J. Appl. Poultry Res. 3:244–252.

Owen, R. L., R. F. Wideman, R. M. Leach, B. S. Cowen, ZP. A. Dunn, and B. C. Ford, 1995a. Physiologic and electrocardiographic changes occurring in broilers reared at simulated high altitude. Avian Dis. 39:108–115.

Owen, R. L., R. F. Wideman, G. F. Barbato, B. S. Cowen, B. C. Ford, and A. L. Hattel, 1995b. Morphometric and histologic changes in the pulmonary system of broilers raised at simulated high altitude. Avian pathol. 24:293–302.

Owen, R. L., R. F. Wideman and B. S. Cowen, 1995c. Changes in pulmonary arterial and femoral arterial blood pressure upon acute exposure to hypobaric hypoxia in broiler chickens. Poultry Sci. 74:708–715.

Peacock, A. J., C. Pickett, K Morris, and J. T. Reeves, 1989. The relationship between rapid growth and pulmonary hemodynamics in the fast-growing broiler chicken. Am. Rev. Respir. Dis. 139:1524–1530.

Peacock, A. J., C. Pickett, K Morris, and J. T. Reeves, 1990. Spontaneous hypoxaemia and right ventricular hypertrophy in fast growing broiler chickens reared at sea level. Comp. Biochem. Physiol. 97A:537–541.

Ploog, H. P., 1973. Physiologic changes in broiler chickens (Gallus domesticus) exposed to a simulated altitude of 4267 m (14000 ft). M.S. Thesis, The Pennsylvania State University, University Park, Pa.

Powell, F. L., R. H. Hastings, and R. W. Mazzone, 1985. Pulmonary vascular resistance during unilateral pulmonary artery occlusion in ducks. Am. J. Physiol. 249: R39–R43.

Rautenfeld, D. B. V., 1993. Systema lymphaticum et splen. Chapter 13, pp477–491. In: *Handbook of Avian Anatomy: Nomina Anatomica Avium*, 2nd edition. J. J. Baumel, A. S. King, J. E. Breazile, H. E. Evans, and J. C. Vanden Berge, eds. Nuttal Ornithological Club, c/o Museum of Comp. Zool., Harvard Univ., Cambridge, Mass.

Reeves, J. T., G. Ballam, S. Hofineister, C. Pickett, K Morris, and A. Peacock, 1991. Improved arterial oxygenation with feed restriction in rapidly growing broiler chickens. Comp. Biochem. Physiol. 99A:481–485.

Roush, W. B., and R. F. Wideman, 1998. Examination of growth velocity and acceleration as predictors of pulmonary hypertension syndrome in broilers. Poultry Science 77 (Supplement 1): 59.

Roush, W. B., and R. F. Wideman, 1999. Evaluation of growth velocity and acceleration in relation to pulmonary hypertension syndrome (PHS). Poultry Sci (submitted).

Roush, W. B., Y. Kochera Kirby, T. L. Cravener, and R. F. Wideman, Jr., 1996. Artificial neural network predictions of ascites in broilers. Poultry Sci. 75:1479–1487.

Roush, W. B., T. L. Cravener, Y. Kochera Kirby, and R. F. Wideman, Jr., 1997. Probabilistic neural network prediction of ascites in broilers based on minimally invasive physiological factors. Poultry Sci. 76:1513–1516.

Ruiz-Feria, C. A., K. W. Beem, M. T. Kidd, and R. F. Wideman, 1999. Plasma taurine levels in broilers with pulmonary hypertension syndrome (PHS, ascites) induced by unilateral pulmonary artery occlusion. Poultry Sci. 78:1627–1633.

Shlosberg, A., M. Bellaiche, G. Zeitlin, M. Ya'Acobi, and A. Cahaner, 1996a. Hematocrit values and mortality from ascites in cold-stressed broilers from parents selected by hematocrit. Poultry Sci. 75:1–5.

Shlosberg, A., M. Bellaiche, V. Hanji, A Nyska, A. Lublin, M. Shemesh, L. Shore, S. Perk, and A. Berman, 1996b. The effect of acetylsalicyclic acid treatment of cold-stressed broilers on susceptibility to the ascites syndrome. Avian Pathol. 25:581–590.

Shlosberg, A., M. Beflaiche, E. Berman, S. Perk, N. Deeb, E. Neumark, and A. Cahaner, 1998. Relationship between broiler chicken hematocrit-selected parents and their progeny, with regard to haematocrit, mortality from ascites and bodyweight. Res. Vet. Sci. 64:105–109.

Sillau, A. H., S. Cueva, and P. Morales, 1980. Pulmonary artery hypertension in male and female chickens at 3300 m. Pflugers Arch. 386:269–275.

Staub, N. C., 1994. Pulmonary intravascular macrophages. Annu. Rev. Physiol. 56:47–67.

Sturkie, P. D., 1986a. Body fluids: blood. Pages 102–129 In: Avian Physiology, 4th ed. P. J. Sturkie, ed. Springer-Verlag, New York, N.Y.

Sturkie, P. D., 1986. Heart and circulation: anatomy, hemodynamics, blood pressure, blood flow. Pages 130–166 In: Avian Physiology, 4th ed. P. J. Sturkie, ed. Springer-Verleg, New York, N.Y.

Tottori, J., R. Yamaguchi, Y. Murakawa, M. Sato, K. Uchida, and S. Tateyama, 1997. Experimental production of ascites in broiler chickens using infectious bronchitis virus and *Escherichia coli*. Avian Dis. 41:214–220.

West, J. B., 1993. *Respiratory Physiology—The Essentials*, 5$^{th}$ ed. Williams and Wilkins, Philadelphia, Pa.

Wideman, R. F., 1997. Understanding pulmonary hypertension syndrome (ascites). Hubbard Farms Technical Report, Walpole, N.H., June 1997:1–6.

Wideman, R. F., 1999a. Cardiac Output in four-, five- and six-week-old broilers, and hemodynamic responses to intravenous injections of epinephrine. Poultry Sci. 78:392–403.

Wideman, R. F., 1999b. Cardio-pulmonary hemodynamics and ascites in broiler chickens. In: Poultry and Avian Biology Reviews. Ed. R. R. Dietert and M. A. Ottinger (in press), 1999.

Wideman, R. F., and W. G. Bottje, 1993. Current understanding of the ascites syndrome and future research directions. Pages 1–20 In: Nutrition and Technical Symposium Proceedings. Novus International, Inc., St. Louis, Mo.

Wideman, R. F., and H. French, 1999a. Broiler breeder survivors of chronic unilateral pulmonary artery occlusion produce progeny resistant to pulmonary hypertension syndrome (ascites) induced by cool temperatures. Poultry Sci. 78:404–411.

Wideman, R. F., and H. French, 1999b. Ascites resistance of progeny from broiler breeders selected for two generations using chronic unilateral pulmonary artery occlusion. Poultry Sci. (in press).

Wideman, R. F., and Y. K. Kirby, 1995a. A pulmonary artery clamp model for inducing pulmonary hypertension syndrome (ascites) in broilers. Poultry Sci. 74:805–812.

Wideman, R. F. and Y. K. Kirby, 1995b. Evidence of a ventilation-perfusion mismatch during acute unilateral pulmonary artery occlusion in broilers. Poultry Sci. 74:1209–1217.

Wideman, R. F., and Y. K. Kirby, 1996. Electrocardiographic evaluation of broilers during the onset of pulmonary hypertension initiated by unilateral pulmonary artery occlusion Poultry Sci. 75:407–416.

Wideman, R. F., and C. Tackett, 1999a. Cardio-pulmonary function in clinically healthy and preascitic broilers: inhalation of 100% oxygen does not reduce pulmonary vascular resistance or pulmonary arterial pressure. Poultry Sci. 78, Suppl 1.

Wideman, R. F., and C. Tackett, 1999b. Cardio-pulmonary function in broilers reared at warm or cold temperatures: inhalation of 100% oxygen does not reduce pulmonary arterial pressure. Poultry Sci. 78, Suppl 1.

Wideman, R. F., Jr., M. Ismail, Y. K. Kirby, W. G. Bottje, R. W. Moore, and R. C. Vardeman, 1995a. Furosemide reduces the incidence of pulmonary hypertension syndrome (ascites) in broilers exposed to cool environmental temperatures. Poultry Sci 74:314–322.

Wideman, R. F., Jr., Y. K. Kirby, M. Ismail, W. G. Bottje, R. W. Moore, and R. C. Vardeman, 1995b. Supplemental l-arginine attenuates pulmonary hypertension syndrome (ascites) in broilers. Poultry Sci. 74:323–330.

Wideman, R. F., Y. K. Kirby, C. D. Tackett, N. E. Marson, and R. W. McNew, 1996a. Cardio-pulmonary function during acute unilateral occlusion of the pulmonary artery in broilers fed diets containing normal or high levels of arginine-HCl. Poultry Sci. 75:1587–1602.

Wideman, R. F., Y. K. Kirby, C. D. Tackett, N. E. Marson, C. J. Tressler, and R. W. McNew, 1996b. Independent and simultaneous unilateral occlusion of the pulmonary artery and extra-pulmonary primary bronchus in broilers. Poultry Sci. 75:1417–1427.

Wideman, R. F., Y. K. Kirby, R. L. Owen, and H. French, 1997. Chronic unilateral occlusion of an extra-pulmonary primary bronchus induces pulmonary hypertension syndrome (ascites) in male and female broilers. Poultry Sci. 76:400–404.

Wideman, R. F., Y. K. Kirby, M. F. Forman, N. Marson, R. W. McNew, and R. L. Owen, 1998a. The infusion rate dependent influence of acute metabolic acidosis on pulmonary vascular resistance in broilers. Poultry Sci. 77:309–321.

Wideman, R. F., M. F. Forman, J. D. Hughes, Y. K. Kirby, N. Marson, and N. B. Anthony, 1998b. Flow-dependent pulmonary vasodilation during acute unilateral pulmonary artery occlusion in jungle fowl. Poultry Sci. 77:615–626.

Wideman, R. F., T. Wing, Y. K. Kirby, M. F. Forman, N. Marson, C. D. Tackett, and C. A. Ruiz-Feria, 1998c. Evaluation of minimally invasive indices for predicting ascites susceptibility in three successive hatches of broilers exposed to cool temperatures. Poultry Sci. 77:1565–1573.

Wideman, R. F., P. Maynard, and W. G. Bottje, 1999a. Thromboxane mimics the pulmonary but not systemic vascular responses to bolus HCl injections in broiler chickens. Poultry Sci. 78:714–721.

Wideman, R. F., P. Maynard, and W. G. Bottje, 1999b. Venous blood pressure in broilers during acute inhalation of 5% carbon dioxide or unilateral pulmonary artery occlusion. Poultry Sci.78:1443–1451.

Wideman, R. F., M. R. Fedde, C. D. Tackett, and G. E. Weigle, 1999c. Cardio-pulmonary function in preascitic (hypoxemic) or normal broilers inhaling ambient air or 100% oxygen. Poultry Science (in press).

Wideman, R. F., and H. French, 2000. Ascites resistance of progeny from broiler breeders selected for two generations using chronic unilateral pulmonary artery occlusion. Poultry Sci. 79:396–401.

Yamaguchi, T., R. F. O'Brien, W. L. Hanson, W. W. Wagner Jr., and I. F. McMurtry, 1989. Prostacyclin contributes to inhibition of hypoxic pulmonary vasoconstriction by alkalosis. Prostaglandins 38:53–63.

What is claimed is:

1. A method of producing improved genetic breeding stocks in chickens, the method comprising:

a) inducing pulmonary hypertension in chickens by occluding the pulmonary vasculature with particulate substances of a size about 8 to about 250 micrometers in diameter injected into veneous blood that carries the particles to the right cardiac ventricle pumping the blood containing the particles to the lungs, wherein the particles directly increase pulmonary vascular resistance by lodging in small blood vessels, the heart being forced to develop and maintain an elevated pressure in the pulmonary arteries to propel the reguisite cardiac output through vessels remaining unoccluded, chickens that are susceptible to pulmonary hypertension subsequently developing pulmonary hypertension syndrome, and b) separating susceptible chickens from the resistant chickens, the resistant chickens being useful as genetic breeding stock resistant to pulmonary hypertension.

2. A method for producing a pulmonary hypertension resistant poultry strain comprising:

a) administering into the pulmonary circulation of immature poultry, particles having about 8 to about 250 $\mu$M diameter in an amount sufficient to kill or disable poultry susceptible to pulmonary hypertension while resistant poultry remain unaffected; and b) selecting and breeding the resistant poultry to produce a pulmonary hypertension resistant poultry strain.

* * * * *

UNITED STATES PATENT AND TRADEMARK OFFICE
CERTIFICATE OF CORRECTION

PATENT NO. : 6,720,473 B1
DATED : April 13, 2004
INVENTOR(S) : Wideman et al.

It is certified that error appears in the above-identified patent and that said Letters Patent is hereby corrected as shown below:

Title page,
Item [12], please change, "Erf et al." to -- Wideman, Jr. et al. --
Item [75], Inventors, should read as follows:
-- Robert F. Wideman, Jr., Fayetteville, AR (US); Gisela F. Erf, Fayetteville, AR (US); Howard L. French, Stirling, Ontario (CA) --.

Signed and Sealed this

First Day of February, 2005

JON W. DUDAS
*Director of the United States Patent and Trademark Office*